(12) United States Patent
Parker et al.

(10) Patent No.: US 11,655,476 B2
(45) Date of Patent: May 23, 2023

(54) MODULAR DNA ASSEMBLY SYSTEM

(71) Applicant: VICTORIA LINK LIMITED, Wellington (NZ)

(72) Inventors: Emily Jane Parker, Wellington (NZ); Matthew Joseph Nicholson, Canterbury (NZ); Craig John Van Dolleweerd, Prebbleton (NZ)

(73) Assignee: Victoria Link Llimited, Wellington (NZ)

( * ) Notice: Subject to any disclaimer, the term of this patent is extended or adjusted under 35 U.S.C. 154(b) by 278 days.

(21) Appl. No.: 16/651,043

(22) PCT Filed: Sep. 28, 2018

(86) PCT No.: PCT/IB2018/057527
§ 371 (c)(1),
(2) Date: Mar. 26, 2020

(87) PCT Pub. No.: WO2019/064242
PCT Pub. Date: Apr. 4, 2019

(65) Prior Publication Data
US 2021/0032635 A1     Feb. 4, 2021

(30) Foreign Application Priority Data
Sep. 29, 2017 (AU) ............................... 2017903955

(51) Int. Cl.
| C12N 15/64 | (2006.01) |
| C12N 15/52 | (2006.01) |
| C12N 15/66 | (2006.01) |
| C12N 15/70 | (2006.01) |
| C12P 17/18 | (2006.01) |

(52) U.S. Cl.
CPC ............. *C12N 15/64* (2013.01); *C12N 15/52* (2013.01); *C12N 15/66* (2013.01); *C12N 15/70* (2013.01); *C12P 17/188* (2013.01); C12N 2510/02 (2013.01); C12N 2800/204 (2013.01); C12N 2800/40 (2013.01); C12N 2800/50 (2013.01)

(58) Field of Classification Search
CPC ........ C12N 15/64; C12N 15/66; C12N 15/70; C12N 2800/40; C12N 2800/50
See application file for complete search history.

(56) References Cited

U.S. PATENT DOCUMENTS

2016/0002644 A1    1/2016  Tuskan et al.

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
International Search Report and Written Opinion corresponding to International Patent Application No. PCT/IB2018/057527, dated Nov. 19, 2018.
Andreou, A., et al., 'Mobius Assembly: A Versatile Framework For Golden Gate Assembly', bioRxiv, 2017: accessed online Nov. 6, 2017 from http://dx.doi.orgIIO.IIOIII40095.
Engler, C, et al., 'A one pot, one step, precision cloning method with high throughput capability' 2008, PloS one, vol. 3, pp. 1-7, e3647. Accessed online Nov. 6, 2017 from http://journals.plos.org/plosone/article/file?id= 1 0.13 711journal.pone.000364 7 &type=printable.
Sarrion-Perdigones, A, et al., 'GoldenBraid: an iterative cloning system for standardized assembly of reusable genetic modules', 2011, PloS one. vol. 6, pp. 1-11, e21622. Accessed online Nov. 6, 2017 from http://journals.plos.org/plosone/article/file?id= 10.1371 ljournal.pone.0021622&type=printable.
De Paoli, H, et al., 'An innovative platform for quick and flexible joining of assorted DNA fragments' 2016, Scientific Reports, vol. 6, pp. 1-14. Accessed online Nov. 6, 2017 from https:llwww.nature.com/articles/srepl9278.pdf.
Weber, E, et al., 'A modular cloning system for standardized assembly of multi gene constructs', 2011, PloS one, vol. 3, pp. 1-11, e 16765. Accessed online Nov. 6, 2017 from http://journals.plos.org/plosone/article/file?id= 1 0.13711journal.pone.00 16765 &type=printable.
Van Dolleweerd, C, et al., MIDAS: A Modular DNA Assembly System for Synthetic Biology, 2018, ACS Synthetic Biology, vol. 7, pp. 1018-1029. Abstract, Figure 3, Figure 5, Discussion.

* cited by examiner

*Primary Examiner* — Iqbal H Chowdhury
(74) *Attorney, Agent, or Firm* — McAndrews, Held & Malloy, Ltd.

(57) ABSTRACT

A modular and hierarchical DNA assembly platform for synthetic biology is described. This enabling technology, termed MIDAS (for Modular Idempotent DNA Assembly System), can precisely assemble multiple DNA fragments in a single reaction using a standardised assembly design. It can be used to build genes from libraries of sequence-verified, reusable parts and to assemble multiple genes in a single vector. We describe the design and use of MIDAS, and its application in the reconstruction of the metabolic pathway for production of paspaline, a key intermediate in the biosynthesis of a range of indole diterpenes—a class of economically important secondary metabolites produced by several species of filamentous fungi.

19 Claims, 35 Drawing Sheets
Specification includes a Sequence Listing.

(A) Analysis of pSK64 transformants (C) Analysis of pSK37 transformants (B) Analysis of pSK63 transformants

MODULAR DNA ASSEMBLY SYSTEM

The present application is filed pursuant to 35 U.S.C. 371 as a U.S. National Phase application of International Patent Application No. PCT/IB2018/057527, which was filed Sep. 28, 2018, claiming the benefit of priority to Australian Patent Application No. 2017903955 filed on Sep. 29, 2017. The entire text of the aforementioned applications is incorporated herein by reference in its entirety.

FIELD OF THE INVENTION

This invention generally relates to a modular and hierarchical DNA assembly platform for synthetic biology termed MIDAS (for Modular Idempotent DNA Assembly System), methods of using this system to precisely assemble multiple DNA fragments in a single reaction using a standardised assembly design, and method of reconstructing biosynthetic pathways for subsequent production of at least one indole diterpene.

BACKGROUND

A central requirement of synthetic biology is the ability to dissect biological systems into basic, reusable parts or modules, and to reorganise and reassemble those parts, in a standardised way, to produce novel genetic modules, interacting proteins, control circuits, metabolic pathways and high value products. In recent years, numerous enabling technologies have emerged to address these requirements at the genetic level. Most of these technologies fall into four broad categories, each offering powerful features, as well as limitations: (i) techniques which utilise site-specific recombinases to assemble DNA molecules together, (ii) techniques based on the in vitro assembly of DNA molecules containing overlapping sequences, (iii) in vivo techniques that utilise cellular, recombination-based mechanisms to assemble DNA molecules bearing homologous sequences, and (iv) techniques based on restriction enzymes.

Site-specific recombination systems, such as those based on bacteriophages λ (1) or P1 (2, 3), or combinations thereof (4, 5), can be used for efficient, high-throughput construction of multigene assemblies. However, due to the presence of recombination site sequence scars, site-specific recombination-based techniques do not readily lend themselves to modular design for the combinatorial assembly of genes from simpler parts.

Techniques that achieve in vitro assembly using DNA sequence overlaps, such as overlap extension PCR (6), Gibson assembly (7), In-Fusion (8, 9) and other ligation-independent cloning methods (10, 11), can efficiently assemble multiple fragments together in a single reaction and, because they are largely sequence independent (i.e., do not rely on specific sequences such as restriction enzyme recognition sites), produce scarless (seamless) assemblies. However, these techniques do not easily lend themselves to modularity, since new primer sets need to be designed every time a new fragment is introduced or the assembly order is changed.

In vivo assembly methods, which utilise cellular homologous recombination machinery to assemble together multiple DNA fragments bearing overlapping terminal sequences, have been developed for E. coli (12), Bacillus spp. (13, 14) and yeast (15-18). In vivo assembly techniques have the power to construct large biochemical pathways and genome-scale assemblies but, like the overlap-directed in vitro assembly methods, they are inherently bespoke, not easily lending themselves to modular assembly of genes from simpler parts.

Traditional approaches using conventional (Type IIP) restriction enzymes for arranging DNA fragments (e.g., genes) in tandem in one vector suffer from the problem that, as the number of DNA fragments increase, the available restriction enzymes become limiting, and cloning becomes increasingly complex. Approaches using rare-cutting restriction enzymes (19, 20) or isocaudomers (21) have had some success in assembling multiple genes in a single vector, but do not offer a truly flexible or modular assembly system that is also (theoretically) capable of indefinite growth. In an effort to overcome this limitation, and to standardise the assembly process, a set of design rules termed the BioBrick standard was developed (22), wherein the idea of idempotency—where a reaction performed on a component produces a new structure, yet leaves that structure unchanged with respect to its ability to participate in further reactions—was proposed in the context of DNA assembly. Nevertheless, the presence of restriction site scars can be problematic for these techniques, particularly when assembling genes from smaller fragments.

More recently, modular DNA assembly techniques based on Golden Gate cloning (23) have been described. Golden Gate cloning utilises the ability of Type IIS restriction enzymes, which recognise non-palindromic sequences and cleave at one side of the recognition site, to seamlessly join multiple DNA fragments together in a single (one-pot) reaction. Techniques such as GoldenBraid (24, 25), the topologically equivalent TNT-Cloning (26), MoClo (27, 28), and the plasmid assembly system described by Binder et al (29), have used the idea of idempotency to extend the principles of Golden Gate cloning, thereby permitting modular and combinatorial assembly of genes from libraries of smaller fragments, and the subsequent assembly of multiple genes together in a single plasmid. In these systems, the direction of assembly is imposed by the compatibility of Type IIS overhangs on neighbouring fragments and vector ends. Thus, at the level of multigene assembly (i.e., assembly of multiple genes in a single vector), only one direction of assembly is possible, and growth of the multigene plasmid (i.e., addition of further genes) can only take place in one direction (i.e., is unidirectional). Whilst this might not be an issue for some projects, there are, however, circumstances in which these unidirectional modular assembly systems (UMASs) impose limitations on the type of multigene plasmids that can be produced, or the ease with which they can be constructed.

An example where the unidirectional nature of multigene assembly inherent to the previously described UMASs imposes limitations, is when constructing multigene assemblies for testing expression of genes intended to be integrated by homologous recombination into the chromosome of an expression host. In this example, the genes of interest need to be placed between flanking left and right homology arms (which mediate the homologous recombination process). In the previously described UMASs this can only be achieved in two ways, either:

(i) Using an alternative cloning technique to construct a new vector wherein the Type IIS restriction sites and sequence elements that mediate modular assembly (termed the Golden Gate cloning cassette) are placed between the two homology arms. However, this requirement to construct a new vector using a different cloning technique (i.e, not using the Golden Gate-based modular assembly system used for multigene assembly), negates the original benefits of using the modular assembly system in the first place. Moreover, every time different chromosomal integration sites are to be tested, a new vector (containing new homology arms) would need to be constructed, or (ii) Using the UMAS to sequentially load the first homology arm, followed by the genes of interest and, finally, the second homology arm. Whilst this avoids the disadvantage described in (i) of having to use an alternative cloning technique, it means that chromosomal integration can only be achieved once the second homology arm has been added. Thus, in these UMASs, the addition of the second homology arm effectively "seals off" the assembly circuit so that any further genes that are added will always lie outside the homology arms.

Another example of the shortcomings of unidirectional assembly is that the unidirectional nature of multigene assembly inherent to UMASs limits the speed and ease with which many of these positional permutations can be constructed.

Thus, although (unidirectional) Golden Gate-based modular assembly techniques are useful for constructing certain types of multigene assemblies, they do not offer a completely flexible approach to assembly. Consequently, there is a need in the art for alternative DNA assembly systems that will provide the user with flexibility in constructing designer polynucleotides and gene assemblies.

Accordingly it is an object of the invention to go at least some way towards addressing the deficiencies in the prior art in providing a modular DNA assembly system that allows for the construction of multigene assemblies bi-directionally and/or that will at least provide the public with a useful choice.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In one aspect the present invention relates to a vector set comprising at least two shuttle vectors, V1 and V2,
  wherein V1 is selected from the group consisting of
    V1.1(+)=5'-A1 B1 M1 B2 C1 C2 A2-3',
    V1.2(−)=5'-A1 C1 C2 B1 M1 B2 A2-3',
    V1.3(+)=5'-A1 B2 M1 B1 C1 C2 A2-3', and
    V1.4(−)=5'-A1 C1 C2 B2 M1 B1 A2-3',
  and V2 is selected from the group consisting of
    V2.1(+)=5'-C1 B1 M1 B2 A1 M2 A2 C2-3',
    V2.2(−)=5'-C1 A1 M2 A2 B1 M1 B2 C2-3',
    V2.3(+)=5'-C1 B2 M1 B1 A1 M2 A2 C2-3', and
    V2.4(−)=5'-C1 A1 M2 A2 B2 M1 B1 C2-3',
  wherein M1 is a first marker, M2 is a second marker, and A1, A2, B1, B2, C1 and C2 are restriction enzyme recognition sites,
  wherein at least A1, A2, C1, and C2 are recognition sites for Type IIS restriction enzymes,
  wherein A1, B1 and C1 are all different recognition sites, and
  wherein A1=A2, C1=C2, and B1=B2 or B1≠B2.

In another aspect the present invention relates to a vector set comprising at least three shuttle vectors,
  wherein at least two of the three vectors are V1 vectors selected from the group consisting of
    V1.1(+)=5'-A1 B1 M1 B2 C1 C2 A2-3',
    V1.2(−)=5'-A1 C1 C2 B1 M1 B2 A2-3',
    V1.3(+)=5'-A1 B2 M1 B1 C1 C2 A2-3', and
    V1.4(−)=5'-A1 C1 C2 B2 M1 B1 A2-3',
  wherein at least one of the V1 vectors is a (+) vector and another V1 vector is a (−) vector,
    and wherein at least one of the three vectors is a V2 vector selected from the group consisting of
    V2.1(+)=5'-C1 B1 M1 B2 A1 M2 A2 C2-3',
    V2.2(−)=5'-C1 A1 M2 A2 B1 M1 B2 C2-3',
    V2.3(+)=5'-C1 B2 M1 B1 A1 M2 A2 C2-3', and
    V2.4(−)=5'-C1 A1 M2 A2 B2 M1 B1 C2-3',
  wherein M1 is a first marker, M2 is a second marker, and A1, A2, B1, B2, C1 and C2 are restriction enzyme recognition sites,
  wherein at least A1, A2, C1, and C2 are recognition sites for Type IIS restriction enzymes,
  wherein A1, B1 and C1 are all different restriction sites, and
  wherein A1=A2, C1=C2, and B1=B2 or B1≠B2.

In another aspect the present invention relates to a vector set comprising at least two shuttle vectors, wherein
  each shuttle vector comprises a first marker (M1), and at least six restriction sites, wherein at least four of the restriction sites are Type IIS restriction sites,
  wherein in at least one first shuttle vector, a first four restriction sites are located 3' or 5' of M1, at least three of the four being Type IIS restriction sites, and a second two restriction sites are located 3' or 5' of M1, at least one of the two being a Type IIS restriction site, and
  wherein in at least one second shuttle vector, a first four restriction sites are located 3' or 5' of M1, at least three of the four being Type IIS restriction sites, and a second two restriction sites are located 5' or 3' of M1, at least one of the two being a Type IIS restriction site,
  wherein the at least one second shuttle vector comprises at least one second marker (M2) flanked by two Type IIS restriction sites, and
  wherein when the first four restriction sites are located 3' of M1 in the at least one first or second vector, the second two restriction sites are located 5' of M1, and the vector is a (+) vector, and
  when the first four restriction sites are located 5' of M1 in the at least one first or second vector, the second two restriction sites are located 3' of M1 and the vector is a (−) vector.

In another aspect the present invention relates to a set of eight shuttle vectors, each shuttle vector comprising a first marker (M1) and six restriction sites,
  wherein each shuttle vector comprises a first set of four restriction sites positioned on one side of M1 and a second set of two restriction sites positioned on the other side of M1,
  wherein
  two of the restriction sites in the first set are the same as each other,
  the two restriction sites in the second set are different from each other, and
  at least one of the two restriction sites in the second set is the same as one of the four restriction sites in the first set, and
  wherein four of the shuttle vectors comprise a second marker (M2), wherein four of the vectors are (+) vectors comprising the first set of restriction sites 3' of M1, and four of the vectors are (−) vectors comprising the first set of restriction sites 5' of M1.

In another aspect the invention relates to a method of making a vector set comprising at least two shuttle vectors comprising combining at least one V1 shuttle vector or first shuttle vector of the invention with at least one V2 shuttle vector or second shuttle vector of the invention.

In another aspect the invention relates to a method of making a multigene construct comprising at least two transcription units (TU), the method comprising
(a) cloning a first cloning cassette comprising a first transcription unit (TU1), and four restriction sites A1, A2, C1 and C2 arranged in the following order:
5'-A1-TU1-C1-C2-A2-3', or
5'-A1-C1-C2-TU1-A2-3',
into a destination vector (V3) comprising a pair of restriction sites A1 and A2 flanking a second marker (M2) to make:
destination vector V3.1 comprising 5'-TU1-C1-C2-3' or
destination vector V3.2 comprising 5'-C1-C2-TU1-3',
(b) cloning a second cloning cassette comprising a second transcription unit (TU2), the second marker (M2), and four restriction sites A1, A2, C1 and C2 arranged in the following order:
5'-C1-TU2-A1-M2-A2-C2-3', or
5'-C1-A1-M2-A2-TU2-C2-3',
into V3.1 to make destination vector V4.1 comprising 5'-TU1-TU2-A1-M2-A2-3', or destination vector V4.2 comprising 5'-TU1-A1-M2-A2-TU2-3', or
into V3.2 to make destination vector V4.3 comprising 5'-TU2-A1-M2-A2-TU1-3', or destination vector V4.4 comprising 5'-A1-M2-A2-TU2-TU1-3'
wherein A1 and C1 are different restriction sites, and wherein A1=A2 and C1=C2.

In another aspect, the invention relates to a set of vectors comprising
(i) four first shuttle vectors or V1 shuttle vectors of the invention,
(ii) four second shuttle vectors or V2 vectors of the invention, and
(iii) at least one destination vector comprising a pair of restriction sites,
wherein the pair of restriction sites in (iii) have a divergent orientation relative to each other and are the same as a pair of restriction sites in each of the shuttle vectors in (i), and in each of the shuttle vectors in (ii)
wherein the restriction sites in (i) have a convergent orientation relative to each other, and
wherein the restriction sites in (ii) have a divergent orientation relative to each other.

Various embodiments of the different aspects of the invention as discussed above are also set out below in the detailed description of the invention, but the invention is not limited thereto.

Other aspects of the invention may become apparent from the following description which is given by way of example only and with reference to the accompanying drawings.

BRIEF DESCRIPTION OF THE DRAWINGS

The invention will now be described with reference to the figures in the accompanying drawings.

DETAILED DESCRIPTION OF THE INVENTION

Definitions

Figure 1:
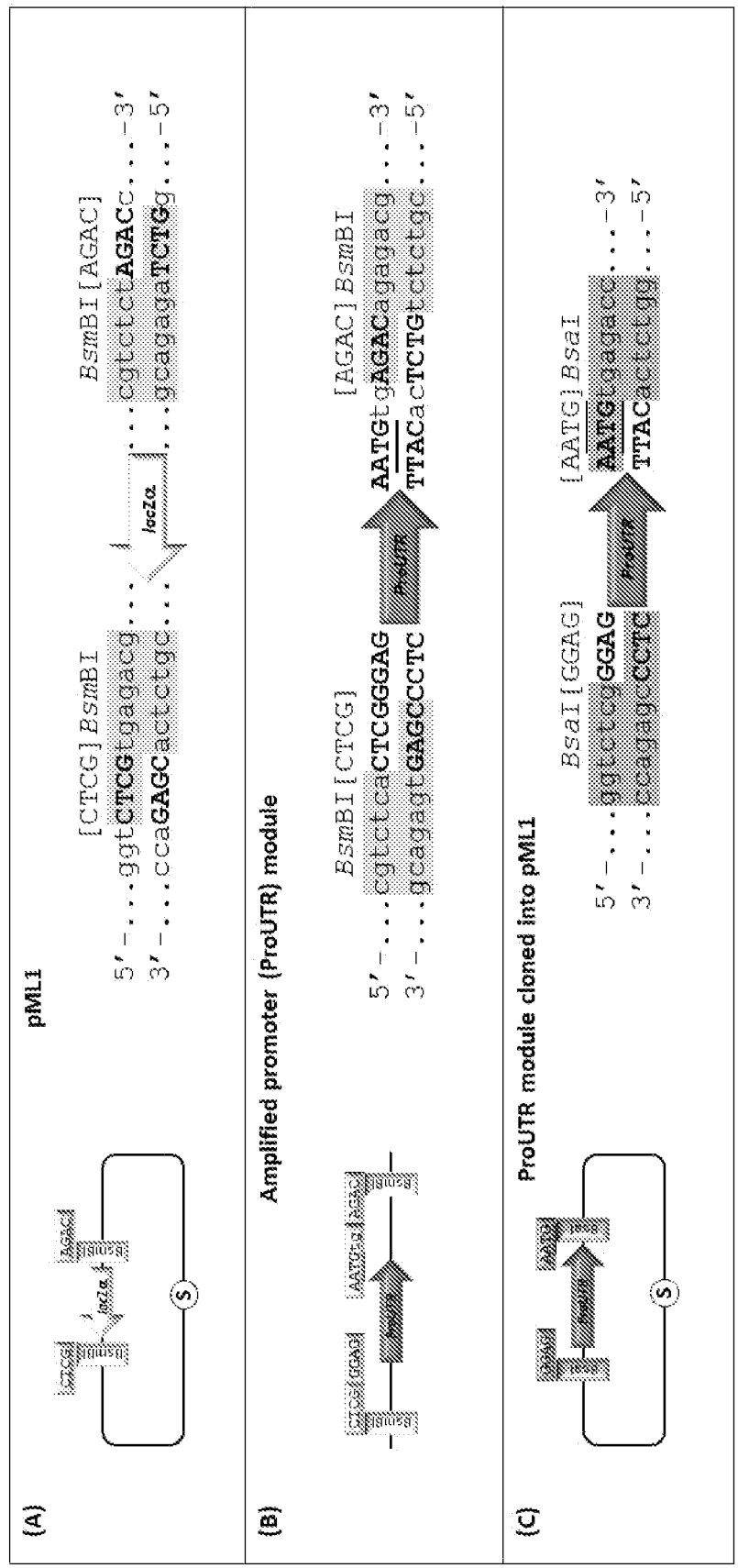
FIG. 1. Overview of MIDAS Level-1 cloning. The figure illustrates the principle of MIDAS Level-1 cloning. In each panel the elements important for MIDAS Level-1 assembly are shown schematically on the left, with sequence-level details shown to the right. (A) The Golden Gate cloning cassette (lacZα flanked by divergent BsmBI sites) of the source vector pML1. Sequence 5'-ggtCTCGtgagacg-3'=SEQ ID NO: 116; sequence 5'-cgtctctAGACc-3'=SEQ ID NO: 117. (B) A PCR product containing a promoter (ProUTR) module flanked by convergent BsmBI sites. Sequence 5'-cgtctcaCTCGGGAG-3'=SEQ ID NO: 118; sequence 5'-AATGtgAGACagagacg-3'=SEQ ID NO: 119. The 4 bp sequences GGAG and AATG represent the module-specific signature unique to ProUTR modules. Following a BsmBI-mediated Golden Gate reaction between pML1 and the amplified ProUTR module, a plasmid consisting of the ProUTR module cloned into pML1 is obtained (C). As per Golden Gate cloning, the BsmBI recognition sites are eliminated in the product plasmid. The complementary design of pML1 and of the primers used to amplify the module results in a cloned module that is flanked by convergent BsaI recognition sites, whose overhangs, following digestion, are the module-specific bases. Sequence 5'-ggtctcgGGAG-3'=SEQ ID NO: 120; sequence 5'-AATGtgagacc-3'=SEQ ID NO: 121.

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "consisting essentially of" as used herein means the specified materials or steps and those that do not materially affect the basic and novel characteristic(s) of the claimed invention.

The term "consisting of" as used herein means the specified materials or steps of the claimed invention, excluding any element, step, or ingredient not specified in the claim.

The terms "recognition site" and "restriction site" are used interchangeably herein and mean the nucleic acid sequence or sequences of a polynucleotide that define the binding site on the polynucleotide for a given restriction enzyme.

The term "a pair of restriction sites" and grammatically equivalent phrases means that the two restriction sites in the pair are the same; i.e., both restriction sites in the pair are restriction sites for the same restriction enzyme.

As used herein, a "divergent orientation" of a pair of restriction sites means that cleavage of the polynucleotide comprising the restriction sites occurs on the outside of the nucleic acid sequences that define the pair of restriction sites, and not between the pair. Conversely, a "convergent orientation" of a pair of restriction sites, and similar grammatical constructions means that cleavage of the polynucleotide comprising the restriction sites occurs to the inside of the nucleic acid sequences that define the pair of restriction sites.

As used herein, when a polynucleotide or nucleic acid sequence is "flanked" by restriction sites, that polynucleotide or nucleic acid sequence comprises a given restriction site to the 5' and a given restriction site to the 3' and no other restriction sites between the given sites.

The phrase "are removed" with reference to a recognition or restriction site that is removed from a cloning cassette or destination vector as described herein means that the ligation of a cloning cassette into another cloning cassette or destination vector results in a cloning cassette or destination vector that does not contain the nucleotide residues of the recognition or restriction site.

The term "genetic construct" refers to a polynucleotide molecule, usually double-stranded DNA, which has been conjugated to another polynucleotide molecule. In one non-limiting example a genetic construct is made by inserting a first polynucleotide molecule into a second polynucleotide molecule, for example by restriction/ligation as known in the art. In some embodiments, a genetic construct comprises a single polynucleotide module, at least two polynucleotide modules, or a series of multiple polynucleotide modules assembled into a single contiguous polynucleotide molecule (also referred to herein as a "multigene construct"), but not limited thereto.

A genetic construct may contain the necessary elements that permit transcription of a polynucleotide molecule, and, optionally, for translating the transcript into a polypeptide. A polynucleotide molecule comprised in and/or by the gene construct may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "transcription unit" (TU) as used herein refers to a polynucleotide comprising a sequence of nucleotides that code for a single RNA molecule including all the nucleotide sequences necessary for transcription of the single RNA molecule, including a promoter, an RNA-coding sequence, and a terminator, but not limited thereto.

The term "transcription unit module" (TUM) as used herein refers to a polynucleotide comprising a sequence of nucleotides that encode a single RNA molecule, or parts thereof; or that encode a protein coding sequence (CDS), or parts thereof; or that encode sequence elements, or parts thereof, that control transcription of that RNA molecule; or that encode sequence elements or parts thereof that control translation of the CDS. Such sequence elements may include, but are not limited to, promoters, untranslated regions (UTRs), terminators, polyadenylation signals, ribosome binding sites, transcriptional enhancers and translational enhancers.

The term "multigene construct" as used herein means a genetic construct that is a polynucleotide comprising at least two transcription units.

The term "marker" as used herein means a nucleic acid sequence in a polynucleotide that encodes a selectable marker or scorable marker.

The term "selectable marker" as used herein refers to a TU, which when introduced into a cell, confers at least one trait on the cell that allows the cell to be selected based on the presence or absence of that trait. In one embodiment the cell is selected based on survival under conditions that kill cells not comprising the at least one selectable marker.

The term "scorable marker" as used herein refers to a TU, which when introduced into a cell, confers at least one trait on the cell that allows the cell to be scored based on the presence or absence of that trait. In one embodiment the cell comprising the TU is scored by identifying the cell phenotypically from a plurality of cells.

The term "genetic element" as used herein refers to any polynucleotide sequence that is not a TU or does not form part of a TU. Such polynucleotide sequences may include, but are not limited to origins of replication for plasmids and viruses, centromeres, telomeres, repeat sequences, sequences used for homologous recombination, site-specific recombination sequences, and sequences controlling DNA transfer between organisms.

The term "source vector" as used herein refers to a vector into which polynucleotide sequences of interest can be cloned. In some embodiments the polynucleotide sequences are TUs, TUMs and/or genetic elements as described herein. In some embodiments a source vector is selected from the group consisting of plasmids, bacterial artificial chromosomes (BACs), phage artificial chromosomes (PACs), yeast artificial chromosomes (YACs), bacteriophage, phagemids, and cosmids. In some embodiments, a source vector comprising a polynucleotide sequence of interest is termed an entry clone. In some embodiments the entry clone can serve as a shuttle or destination vector for receiving further polynucleotide sequences.

The term "shuttle vector" as used herein refers to a vector into which polynucleotide sequences of interest can be cloned and from which they can be manipulated. In some embodiments the polynucleotide sequences are TUs, TUMs and/or genetic elements as described herein. In some embodiments a shuttle vector is selected from the group consisting of plasmids, bacterial artificial chromosomes (BACs), bacteriophage P1-derived artificial chromosomes (PACs), yeast artificial chromosomes (YACs), bacteriophage, phagemids, and cosmids. In some embodiments, a shuttle vector comprising a polynucleotide sequence of interest can serve as a destination vector for receiving further polynucleotide sequences.

The term "destination vector" as used herein refers to a vector into which polynucleotide sequences of interest can be cloned. In some embodiments the polynucleotide sequences are TUs, TUMs and/or genetic elements as described herein. In some embodiments a destination vector is selected from the group consisting of plasmids, bacterial artificial chromosomes (BACs), bacteriophage P1-derived artificial chromosomes (PACs), yeast artificial chromosomes (YACs), bacteriophage, phagemids, and cosmids. In some embodiments, a destination vector comprising a polynucleotide sequence of interest is an entry clone. In some embodiments the entry clone can serve as a destination vector for receiving further polynucleotide sequences.

The term "vector" as used herein refers to any type of polynucleotide molecule that may be used to manipulate genetic material so that it can be amplified, replicated, manipulated, partially replicated, modified and/or expressed, but not limited thereto. In some embodiments a vector may be used to transport a polynucleotide comprised in that vector into a cell or organism.

The term "polynucleotide(s)," as used herein, means a single or double-stranded deoxyribonucleotide or ribonucleotide polymer of any length, and include as non-limiting examples, coding and non-coding sequences of a gene, sense and antisense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, fragments, genetic constructs, vectors and modified polynucleotides. Reference to nucleic acids, nucleic acid molecules, nucleotide sequences and polynucleotide sequences is to be similarly understood.

The term "gene" as used herein refers to gene the biologic unit of heredity, self-reproducing and located at a definite position (locus) on a particular chromosome. In one embodiment the particular chromosome is a eukaryotic or bacterial chromosome. The term bacterial chromosome is used interchangeably herein with the term bacterial genome.

The term "gene cluster" as used herein refers to a group of genes located closely together on the same chromosome whose products play a coordinated role in a specific aspect of cellular primary or secondary metabolism.

The terms "under conditions wherein the . . . enzyme is active" and "under conditions wherein the . . . enzymes are active", and grammatical variations thereof when used in reference to enzyme activity mean that the enzyme will perform it's expected function; e.g., a restriction endonuclease will cleave a nucleic acid at an appropriate restriction site, and a DNA ligase will covalently join two polynucleotides together.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct or an expression cassette, a "coding sequence" is capable of being expressed when it is operably linked to promoter and terminator sequences and/or other regulatory elements.

"Operably-linked" means that the sequence to be expressed is placed under the control of regulatory elements.

"Regulatory elements" as used herein refers to any nucleic acid sequence element that controls or influences the expression of a polynucleotide insert from a vector, genetic construct or expression cassette and includes promoters, transcription control sequences, translation control sequences, origins of replication, tissue-specific regulatory elements, temporal regulatory elements, enhancers, polyadenylation signals, repressors and terminators. Regulatory elements can be "homologous" or "heterologous" to the polynucleotide insert to be expressed from a genetic construct, expression cassette or vector as described herein. When a genetic construct, expression cassette or vector as described herein is present in a cell, a regulatory element can be "endogenous", "exogenous", "naturally occurring" and/or "non-naturally occurring" with respect to cell.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate the transcription of a polynucleotide sequence. Promoters comprise cis-initiator elements which specify the transcription initiation site and conserved boxes. In one non-limiting example, bacterial promoters may comprise a "Pribnow box" (also known as the −10 region), and other motifs that are bound by transcription factors and promote transcription. Promoters can be homologous or heterologous with respect to polynucleotide sequence to be expressed. When the polynucleotide sequence is to be expressed in a cell, a promoter may be an endogenous or exogenous promoter. Promoters can be constitutive promoters, inducible promoters or regulatable promoters as known in the art.

"Homologous" as used herein with reference to polynucleotide regulatory elements, means a polynucleotide regulatory element that is a native and naturally-occurring polynucleotide regulatory element. A homologous polynucleotide regulatory element may be operably linked to a polynucleotide of interest such that the polynucleotide of interest can be expressed from a, vector, genetic construct or expression cassette according to the invention.

"Heterologous" as used herein with reference to polynucleotide regulatory elements, means a polynucleotide regulatory element that is not a native and naturally-occurring polynucleotide regulatory element. A heterologous polynucleotide regulatory element is not normally associated with the coding sequence to which it is operably linked. A heterologous regulatory element may be operably linked to a polynucleotide of interest such that the polynucleotide of interest can be expressed from a, vector, genetic construct or expression cassette according to the invention. Such promoters may include promoters normally associated with other genes, ORFs or coding regions, and/or promoters isolated from any other bacterial, viral, eukaryotic, or mammalian cell.

A "functional fragment" of a polypeptide is a subsequence of the polypeptide that performs a function that is required for the biological activity or binding of that polypeptide and/or provides the three dimensional structure of the polypeptide. The term may refer to a polypeptide, an aggregate of a polypeptide such as a dimer or other multimer, a fusion polypeptide, a polypeptide fragment, a polypeptide variant, or functional polypeptide derivative thereof that is capable of performing the polypeptide activity.

"Isolated" as used herein with reference to polynucleotide or polypeptide sequences describes a sequence that has been removed from its natural cellular environment. An isolated molecule may be obtained by any method or combination of methods as known and used in the art, including biochemical, recombinant, and synthetic techniques. The polynucleotide or polypeptide sequences may be prepared by at least one purification step.

"Isolated" when used herein in reference to a cell or host cell describes to a cell or host cell that has been obtained or removed from an organism or from its natural environment and is subsequently maintained in a laboratory environment as known in the art. The term encompasses single cells, per se, as well as cells or host cells comprised in a cell culture and can include a single cell or single host cell.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the polypeptides useful in the invention have biological activities that are the same or similar to those of a corresponding wild type molecule; i.e., the parent polypeptides or polynucleotides.

In certain embodiments, variants of the polypeptides described herein have biological activities that are similar, or that are substantially similar to their corresponding wild type molecules. In certain embodiments the similarities are similar activity and/or binding specificity.

In certain embodiments, variants of the polypeptides described herein have biological activities that differ from their corresponding wild type molecules. In certain embodiments the differences are altered activity and/or binding specificity.

The term "variant" with reference to polynucleotides and polypeptides encompasses all forms of polynucleotides and polypeptides as defined herein.

The terms "modulate(s) expression", "modulated expression" and "modulating expression" of a polynucleotide or polypeptide, are intended to encompass the situation where genomic DNA corresponding to a polynucleotide to be expressed according to the invention is modified thus leading to modulated expression of a polynucleotide or polypeptide of the invention. Modification of the genomic DNA may be through genetic transformation or other methods known in the art for inducing mutations. The "modulated expression" can be related to an increase or decrease in the amount of messenger RNA and/or polypeptide produced and may also result in an increase or decrease in the activity of a polypeptide due to alterations in the sequence of a polynucleotide and polypeptide produced.

The terms "modulate(s) activity", "modulated activity" and "modulating activity" of a polynucleotide or polypeptide, are intended to encompass the situation where genomic DNA corresponding to a polynucleotide to be expressed according to the invention is modified thus leading to modulated expression of a polynucleotide or modulated expression or activity of polypeptide of the invention. Modification of the genomic DNA may be through genetic transformation or other methods known in the art for inducing mutations. The "modulated activity" can be related to an increase or decrease in the amount of messenger RNA and/or polypeptide produced and may also result in an increase or decrease in the functional activity of a polypeptide due to alterations in the sequence of a polynucleotide and polypeptide produced.

The term "source vector" means a pML1 vector as described herein. Source vectors are also termed level one vectors herein.

The term "shuttle vector" means a pML2 vector as described herein. Source vectors are also termed level two vectors herein.

The term "destination vector" means a pML3 vector as described herein. Source vectors are also termed level three vectors herein.

The term "MIDAS cassette" as used herein means the region of a vector according to the invention that comprises at least six restriction enzyme recognition sites: 5'-1-2-3-4-5-6-3', where sites 1 and 6 are the same as each other, sites 4 and 5 are the same as each other, and sites 1 and 6 are different from sites 4 and 5. In one embodiment sites 2 and 3 are the same as each other. In one embodiment, sites 2 and 3 are different from each other. In some embodiments the MIDAS cassette comprises a marker (M) positioned between 2 and 3 or between 4 and 5, or both.

The term "B" vector as used herein means that in a vector according to the invention the entire MIDAS cassette has flanking convergent restriction sites and nested within is a polynucleotide encoded marker flanked by divergent restriction sites. The term "W" vector as used herein means that in a vector according to the invention, the configuration of restriction sites is inverted relative to the "B" vector, and there is no polynucleotide encoded marker. The restriction sites flanking the MIDAS cassette in the "B" and "W" vectors are different from the restriction sites flanking the polynucleotide encoded marker.

The term "vector set" as used herein means that the vectors in the vector set are designed to be used together in a cloning system to make a multigene construct where a nucleic acid sequence of interest added into the multigene construct can be added to the 5' or the 3' of a nucleic acid sequence of interest already present in a polynucleotide, and in either a forward or a reverse orientation relative to the direction of transcription of the added nucleic acid sequence into the multigene construct.

The term "a biosynthetic pathway" and grammatical variations thereof as used herein mean(s) a group of genes which when expressed together, provide the full complement of gene products required to carry out the biochemical transformations of a substrate molecule to the final product molecule after which the pathway is named.

A naturally occurring biosynthetic pathway is one where the complement of genes is found naturally occurring within an organism. An artificial biosynthetic pathway will also contain the full complement of genes required to carry out the biochemical transformation of the pathway, but the construct from which the genes are expressed may be artificially created, or the genes themselves may be a mosaic of genes from different sources, for example, which do not occur naturally together in a single organism, all providing the full complement of gene products required to produce the biochemical transformation of the named pathway.

By way of example, an indole diterpene biosynthetic pathway may be constructed as described herein using the full complement of genes from a single organism that are required to produce indole diterpene. In some embodiments the entire pathway may be reconstructed in a destination vector for expression in a permissive host as described herein using the methods of the invention as described herein. In some embodiments the permissive host is a fungal host.

Alternatively a part of an indole diterpene biosynthetic pathway may be reconstructed as described herein for expression in a permissive host to produce a destination vector comprising at least one, preferably two, preferably three, preferably four, preferably five, preferably six or more genes to be expressed following the methods of the invention as described herein.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

DETAILED DESCRIPTION

Constructing and modifying metabolic pathways for expression in heterologous systems requires that a skilled worker be able to assemble genes (i.e., transcription units (TUs)) of interest from basic functional and reusable parts (including promoters, coding sequences (CDS), transcriptional terminators, tags, 3' and 5' untranslated regions (UTRs), but not limited thereto). The skilled worker should then be able to take the constructed genes of interest and assemble them together to produce functional multigene constructs that, when introduced into an expression host of choice, will produce desired proteins, pathways and/or products. In the context of heterologous expression, the ability to rapidly trial different combinations of basic gene parts (e.g., promoters, coding sequences (CDS), transcriptional terminators, tags, 3' and 5' untranslated regions (UTRs), but not limited thereto) and different combinations of genes (e.g., TUs) using a simple set of design rules is a highly desirable feature of any enabling technology for synthetic biology.

Accordingly, disclosed herein is a modular DNA cloning system, termed MIDAS (for Modular Idempotent DNA Assembly System) that provides the skilled worker with a new and inventive system and method for assembling genes and for producing multigene expression constructs. MIDAS makes use of restriction ligation cloning (23) (i.e., the efficient and seamless assembly of DNA fragments using Type IIS restriction enzymes) for the ordered and hierarchical assembly of multigene expression constructs from basic standardised parts or modules. Since these basic standardized parts or modules are physically stored (in the pML1 vector), they form readily accessible libraries, from which more complex structures (transcription units and multigene plasmids) can be assembled.

In the work described herein, the inventors have used MIDAS to construct a series of multigene plasmids from basic transcription unit modules (TUMs). The most complex plasmid produced in this work (pSK79) was assembled from 21 different TUMs (seven genes (also termed "transcription units" (TU) herein), each composed of three basic modules). They show that this plasmid, when transformed into a *P. paxilli* strain devoid of the entire PAX cluster, can reconstitute the metabolic pathway for paspaline and paxilline production.

The basic principles described for MIDAS Level-1 (module cloning) and Level-2 (TU assembly) are similar to those described for certain Golden Gate-based modular assembly techniques (24-27, 29). However, it is at the stage of multigene assembly (Level-3 in MIDAS) that the techniques effectively diverge from one another. The inventor's surprising approach to multigene assembly is based on the novel and inventive design of various plasmids used at the earlier levels, conferring distinct advantages to the user over other known modular assembly techniques.

The vector set described herein comprises of a suite of vectors designed to give maximum user control over the construction of transcription units (TUs) from basic modular parts, as well as full user control of TU order and orientation, and control of the direction of assembly of TUs in a multigene construct. This level of control is derived from the modular format, the relative configurations of the Type IIS restriction sites, and the hierarchical nature of assembly, and provides distinct and unexpected advantages over other types of gene assembly protocols.

The modular assembly system described in this specification overcomes the unidirectional limitations of the previously described modular assembly techniques, by providing bi-directional control of the addition of genes into the multigene assembly (i.e., control of the position of each gene with respect to the other genes in the assembly), in addition to full user control of the order of addition of each gene in the multigene assembly and full user control of the relative orientation (direction of transcription) of each gene in the multigene assembly.

MIDAS Design Overview

The inventors have developed the vector set described herein (termed the MIDAS system to take advantage of the ability of Type IIS restriction enzymes to seamlessly join multiple DNA fragments together in a single reaction. Through the appropriate choice of these user-defined overhangs, and the appropriate orientation of the Type IIS sites flanking each of the DNA fragments, multiple fragments can be assembled into a vector in an ordered (directional) fashion using a one-pot restriction-ligation reaction. The vector typically contains a marker (usually the lacZα scorable marker for blue/white screening) flanked by two divergently oriented recognition sites for a Type IIS enzyme; these elements, collectively called the 'cloning cassette', are replaced by the insert during the assembly reaction. In one non-limiting example, MIDAS makes use of three Type IIS restriction enzymes, AarI, BsaI and BsmBI, which generate user-defined 4 bp overhangs upon cleavage.

The assembly of genes and multigene constructs using MIDAS is a hierarchical process. At the first level (MIDAS Level-1), functional modules (such as promoters, CDS, transcriptional terminators, tags, untranslated regions (UTRs), transcriptional enhancers) are cloned into the Level-1 source vector (pML1) using BsmBI-mediated restriction-ligation reactions, where they form libraries of reusable, sequence-verified parts. The complementary design of the modules and source vector ensures that, once cloned into pML1, these modules can be released from the vector by digestion with BsaI.

At the second level (Level-2), compatible sets of the sequence-verified Level-1 modules are released from pML1 and assembled into a Level-2 shuttle vector (pML2) using a BsaI-mediated restriction/ligation reaction, leading to creation of a Level-2 plasmid containing a eukaryotic transcription unit (TU). Once again, the design rules ensure that each assembled TU can be released from the pML2 vector—this time by digestion either with AarI or BsmBI (depending on the pML2 vector in which the TU was assembled).

At Level-3, the TUs that were assembled at Level-2 are released from the pML2 plasmids and are sequentially assembled together in a Level-3 destination vector (pML3), using either AarI- or BsmBI-mediated restriction-ligation reactions, to form functional multigene constructs, which can then be transformed into the desired expression host.

The following description of the MIDAS system in accordance with the invention is provided by way of non-limiting example. The reader will appreciate that modifications, variations and/or improvements of the system as described below may be made in accordance with the inventive concept embodied in the present disclosure. Such modifications, variations and/or improvements are contemplated herein and as is appreciated by the skilled worker, form part of the present invention.

Level-1: Module Cloning

In one embodiment, level-1, functional transcription unit modules (TUMs) are generated as a PCR product. In another embodiment level-1 TUMs are made by direct polynucleotide synthesis. In one embodiment, TUMs are cloned into the Level-1 source vector (pML1) by BsmBI-mediated restriction/ligation. To allow TUMs produced by PCR to be cloned into a pML1 vector, PCR primers are designed so that each amplified TUM is flanked by two convergent BsmBI restriction sites, BsmBI[CTCG] and [AGAC]BsmBI. Upon restriction enzyme cleavage, these convergent restriction sites generate sticky ends that are compatible with those of the BsmBI sites present in the pML1 source vector. TUMs produced by direct synthesis are designed and produced with flanking convergent BsmBI sites, BsmBI[CTCG] and [AGAC]BsmBI, which upon restriction enzyme cleavage, generate sticky ends that are compatible with those of the BsmBI sites present in the pML1 source vector. Thus, the cloning cassette present in pML1 consists of two divergent BsmBI sites flanking a lacZα selectable marker: 5'-[CTCG]BsmBI-lacZα-BsmBI[AGAC]-3' (FIG. 1A).

To enable subsequent (Level-2) assembly of full-length TUs, each TUM is designed to be flanked by four module-specific nucleotides (NNNN) at the 5' end, and four module-specific nucleotides (NNNN) at the 3' end. In certain embodiments the four module specific nucleotides at the 5' and 3' ends included in a TUM that is produced by direct synthesis, whereas in certain embodiments they are included in a TUM that is produced by PCR, by design as part of the PCR primer sequences. The complementary design of the flanking regions of each TUM and the pML1 vector ensures that when each TUM is cloned into pML1 using the BsmBI-mediated restriction/ligation reaction, each TUM becomes flanked by convergent BsaI recognition sites. Thus, when the module is released from pML1 during subsequent (i.e., Level-2) BsaI-mediated assembly of the full-length TU, the module-specific nucleotides (NNNN and NNNN) become the BsaI-specific 4 bp overhangs.

In one embodiment, the overall structure of each module in the PCR product (or synthetic polynucleotide) takes the form: 5'-BsmBI[CTCG]NNNN-TUM-NNNNtg[AGAC]BsmBI-3' (FIG. 1B), which becomes 5'-BsaI[NNNN]-TUM-[NNNN]BsaI-3' in pML1, following BsmBI-mediated cloning (FIG. 1C).

Figure 2:
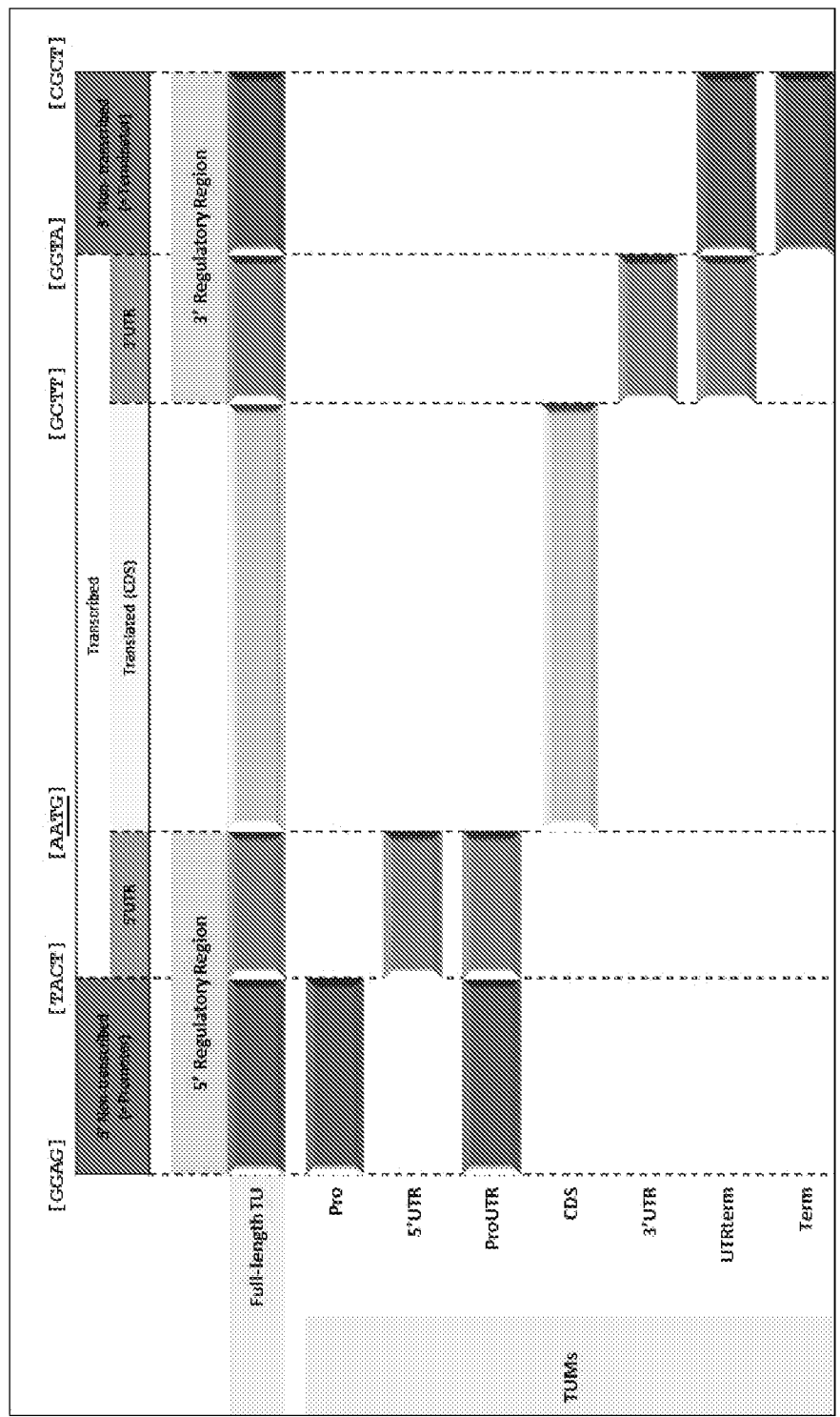
FIG. 2. MIDAS module address system. A eukaryotic transcription unit (TU), comprising a CDS and those surrounding elements that control its expression (the 5' and 3' regulatory regions, shaded grey), is depicted schematically. The 5' regulatory region consists of the non-transcribed promoter (Pro) region and 5' untranslated region (UTR), while the 3' regulatory region consists of a 3'UTR and the non-transcribed terminator (Term), which contains the polyadenylation signal. For the purposes of MIDAS, each of these regions can be produced as separate transcription unit modules (TUMs). However, in many cases, this level of complexity may not be desired and the minimal number of TUMs required to assemble a TU can be reduced to three (ProUTR, CDS and UTRterm). The ordered and directional assembly of TUs from cloned Level-1 TUMs is achieved by ensuring that each type of TUM is flanked by unique sets of nucleotides (the module-specific bases), shown at the top of the figure, which form the overhangs after BsaI cleavage.

As each TUM is defined by its flanking four nucleotides, these module-specific bases effectively form an address system for each TUM and they determine its position and orientation within the assembled TU. The developers of several related polynucleotide assembly techniques, MoClo and GoldenBraid2.0, have already worked in concert to develop a common syntax or set of standard addresses for plant expression (referred to as 'fusion sites' in the MoClo system and 'barcodes' in GoldenBraid2.0) for a wide variety of TUMs to facilitate part exchangeability (30). This standard is also adopted here for MIDAS-based assembly of TUs for expression in filamentous fungi (FIG. 2), but not limited thereto.

Thus, in one non-limiting example, for filamentous fungal expression, a ProUTR module (comprising a promoter, 5' untranslated region (UTR) and ATG initiation codon) comprises GGAG as the module-specific 5' nucleotides, and AATG as the module-specific 3' nucleotides (i.e., 5'-GGAG-ProUTR-AATG-3'), with the translation initiation codon underlined. Similarly, a coding sequence (CDS) module would be flanked by AATG and GCTT (i.e., 5'-AATG-CDS-GCTT-3'), while a UTRterm module (consisting of a 3'UTR and a 3' non-transcribed region, including the polyadenylation signal) would have the form 5'-GCTT-UTRterm-CGCT-3'. Considerations for the design of PCR primers for amplifying these three types of TUM are shown in TABLE 5.

Following the BsmBI-mediated assembly of TUMs in pML1, reactions are transformed into an *E. coli* strain such as DH5α (or equivalent) and spread onto LB plates supplemented with 50 μg/mL spectinomycin, 1 mM IPTG and 50 μg/mL X-Gal. Plasmids harbouring a cloned TUM are identified by screening white colonies and confirmed by sequencing.

At MIDAS Level-1, it is important that all internal recognition sites for AarI, BsaI and BsmBI are masked or eliminated from the TUMs. The process of masking or removal of such sites—referred to as "domestication"—can be achieved by; (i) excluding these sites when ordering the sequences from a gene synthesis company, (ii) directed mutagenesis, or (iii) using masking oligonucleotides that form triplexes with the target DNA, thereby preventing restriction enzyme cleavage (26). In the same way that Type IIS enzymes have previously been utilised for mutagenesis (31) and for Golden Gate domestication purposes (23, 32), domesticated MIDAS modules were prepared by PCR using primers (referred to as domestication primers) that overlap the internal Type IIS restriction site and which contain a single nucleotide mismatch that destroys the site. Because the PCR products are designed to be assembled together in MIDAS using a BsmBI-mediated Golden Gate reaction to form the full-length domesticated TUM in pML1, it is important that the MIDAS domestication primers be designed with BsmBI restriction sites that generate compatible overhangs at their 5' ends.

Level-2: TU Assembly

At Level-2, compatible sets of cloned and sequence-verified Level-1 TUMs are assembled into a pML2 shuttle vector using a BsaI-mediated restriction/ligation reaction, leading to creation of a Level-2 plasmid (pML2 entry clone) containing a complete (i.e., full-length) transcription unit (TU). In one embodiment, the cloned and sequenced Level-1 TUMs are selected from the group consisting of ProUTR, CDS and UTRterm modules and combinations thereof.

The module address standard described herein ensures that the assembly of a TU proceeds in an ordered, directional fashion, with the 3' end of one module being compatible with the 5' end of the next module. The module-specific bases GGAG, located at the 5' end of ProUTR modules, and CGCT, at the 3' end of UTRterm modules, are compatible with the overhangs generated by BsaI digestion of the pML2 shuttle vectors, and these bases therefore define the outermost cloning boundaries of a Level-2 assembly.

In one embodiment of MIDAS, there are eight Level-2 (pML2) shuttle vectors into which a TU can be assembled, the choice of which depends on (i) the desired order of TU assembly, (ii) the desired direction in which TUs are added to the multigene construct and (iii) the desired TU orientation in the multigene construct produced at Level-3.

In one embodiment the eight pML2 vectors are distinguished from one another by the arrangement of specific nucleic acid sequence features that are central to the operation of MIDAS. These nucleic acid sequence features, collectively called the MIDAS cassette (FIG. 3), define the Level-2 assembly of TUs and govern the assembly of multigene constructs produced at Level-3. In some embodiments each pML2 vector comprises a MIDAS cassette that is defined by (i) having a cloning cassette with flanking, divergent Type IIS restriction sites, preferably BsaI recognition sites, (ii) differing arrangements of restriction sites for at least two other Type IIS restriction enzymes, preferably AarI and BsmBI, and (iii) the presence or absence of a lacZα selectable marker.

In one embodiment, the cloning cassettes in all eight pML2 vectors comprise a mutant *E. coli* pheS selectable marker operably linked to the *E. coli* chloramphenicol acetyltransferase promoter which are flanked by divergent BsaI recognition sites. In one embodiment the mutant *E. coli* pheS gene that is the selectable marker is a Thr$^{251}$Ala/Ala$^{294}$Gly double mutant. This double mutant confers high lethality to cells grown on LB media supplemented with the phenylalanine analogue 4-chloro-phenylalanine, 4CP (33). During BsaI-mediated Level-2 assembly of TUs, the mutant pheS gene is eliminated from the pML2 vectors. In one embodiment the mutant pheS is a negative selection marker.

In one embodiment the eight pML2 vectors comprise four "B" vectors and four "W" vectors. The designation of a vector as "B" or "W" depends on the presence or absence, respectively, of a selectable marker, preferably a lacZα selectable marker, in the MIDAS cassette (see FIG. 3).

Described herein are four "B" pML2 vectors (indicated by the "B" in the plasmid name) and four "W" pML2 vectors (indicated by the "W" in the plasmid name). The "B" and "W" vectors also differ in the relative configuration of the AarI and BsmBI restriction sites in their MIDAS cassettes.

"B" vectors comprise a MIDAS cassette flanked by convergent BsmBI sites, further comprising a nested lacZα selectable marker between the BsmBI sites, the lacZα selectable marker being flanked by divergent AarI sites.

"W" vectors comprise a MIDAS cassette flanked by convergent AarI sites, further comprising two nested, divergent BsmBI sites. There is no lacZα selectable marker in the "W" vectors.

The lacZα selectable marker is not used for blue/white screening during the Level-2 assembly of TUs, but is reserved for use at Level-3. However, the choice of "B" or "W" vector determines the order in which a TU is added to a gene construct at Level-3 and so must be made during Level-2 assembly of TUs. Likewise, the Type IIS restriction sites, preferably the AarI and BsmBI sites, are not used for Level-2 assembly of TUs; instead these sites are employed during the Level-3 assembly of the gene constructs. These considerations are discussed further below, under the Level-3 description.

The orientation (direction of transcription) of each TU can be freely defined by assembling each TU in either a pML2 "Forward" vector (indicated by "F" in the plasmid name) or a pML2 "Reverse" vector (indicated by "R" in the plasmid name). The pML2 "Reverse" vectors have their Type IIS restriction sites, preferably BsaI recognition sites switched relative to the BsaI fusion sites in the pML2 "Forward" vectors. Thus, pML2 "Forward" vectors have their pheS-based cloning cassette oriented 5'-[GGAG]BsaI-pheS▶-BsaI[CGCT]-3' (so that the direction of transcription of pheS is the same as the direction of transcription of the $Kan^R$ gene in the pML2 plasmid), while the pML2 "Reverse" vectors have their BsaI recognition sites switched: 5'-[AGCG]BsaI-◀pheS-BsaI[CTCC]-3', (so that the direction of transcription of pheS is opposite to the direction of transcription of the $Kan^R$ gene in the pML2 plasmid), where the arrowhead indicates the direction of transcription of the mutant pheS selectable marker.

In contrast to the cloned Level-1 modules, the pML2 shuttle vectors confer antibiotic kanamycin resistance, allowing efficient counter selection against Level-1 module backbones, while the mutant pheS selectable marker provides powerful negative selection against any parental pML2 shuttle plasmids when E. coli DH5α cells (or equivalent) transformed with the assembly reactions are spread onto LB plates supplemented with 75 µg/mL kanamycin and 1.25 mM 4CP. The skilled person recognizes that any suitable selectable markers that differ from the mutant pheS and $Kan^R$ markers may be used in the pML2 shuttle vectors.

For simplicity, the description of MIDAS provided herein has focussed on the assembly of transcription units (TUs) from basic, functional transcription unit modules (TUMs) such as promoters, CDSs and terminators. However, in some circumstances, for example where one is not interested in testing the effect of different promoter and/or terminator combinations on gene expression, one may not wish to assemble a TU from individual TUMs. For example, some researchers may wish to use a resistance marker cassette (RC) that is already well-characterised for use in their expression host—i.e., has well-characterised promoter, CDS and terminator. In these cases, the full-length TU could be amplified as a complete unit using primers containing the external-most module-specific bases of the MIDAS system, ready for cloning into pML1 (i.e., the PCR product would have the form: 5'-BsmBI[CTCG]GGAG-ProUTR-CDS-UTRterm-CGCTtg[AGAC]BsmBI-3')

(CGCTtgAGAC=SEQ ID NO: 1). Alternatively, the full-length TU could be made by direct synthesis as a complete unit ready for cloning into pML1 (i.e., the direct synthesis product would have the form: 5'-BsmBI[CTCG]GGAG-ProUTR-CDS-UTRterm-CGCTtg[AGAC]BsmBI-3') [SEQ ID NO: 1].

In the same fashion, MIDAS can be applied to the cloning and assembly of genetic elements (GEs) which do not form the basis of TUs. In some embodiments, GEs may include origins of replication (e.g. the yeast 2p replication origin) for propagation of plasmids, T-DNA left and right borders for Agrobacterium-mediated transformation of plant cells, and homology arms for recombination-mediated gene replacement in the desired expression host, but not limited thereto. As in the example of the resistance cassette described above, a GE of interest can be amplified as a complete unit using primers containing the external-most module-specific bases of the MIDAS system or made by direct synthesis, i.e., a PCR or direct synthesis product having the form: 5'-BsmBI[CTCG]GGAG-GE-CGCTtg[AGAC]BsmBI-3' [SEQ ID NO: 1].

In both the cases described above, once a RC or GE is cloned into a pML1 vector, the RC or GE may be moved into a Level-2 vector by BsaI-mediated restriction-ligation assembly as described herein.

Level-3: Assembly of Multigene Constructs

At MIDAS Level-3, TUs and GEs comprised in pML2 plasmids as described herein are sequentially inserted by binary assembly into a Level-3 destination vector (pML3) to form a multigene construct.

Assembly of multigene constructs at Level-3 employs an inventive, relative configuration of the AarI and BsmBI restriction sites in the MIDAS cassettes located in the "B" and "W" pML2 vectors. Without wishing to be bound by theory the inventors believe that the nested and inverted configuration of these restriction sites in the "W" vectors as compared to the "B" vectors defines at least some of the novel and inventive features of the MIDAS multigene assembly process.

In one non-limiting embodiment of the "B" vectors, the entire MIDAS cassette has flanking convergent BsmBI sites and nested within is a lacZα gene flanked by divergent AarI sites. In one non-limiting embodiment of the "W" vectors, the enzyme configuration is inverted (the entire MIDAS cassette has flanking convergent AarI sites and nested within are two divergent BsmBI sites) and there is no lacZα gene.

Figure 4:
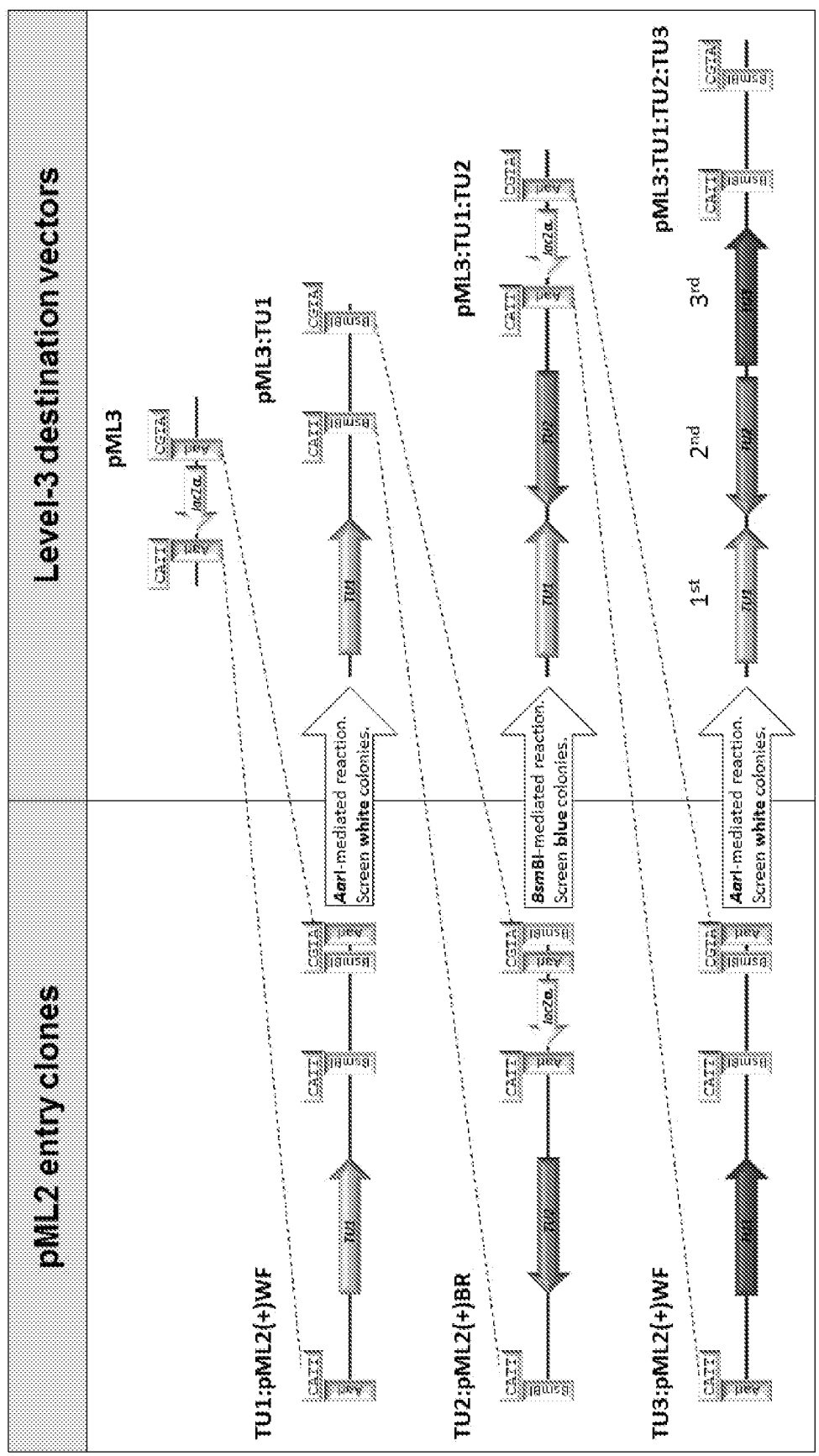
FIG. 4. MIDAS principle of Level-3 (multigene) assembly. MIDAS multigene assembly involves the sequential addition of TUs into the Level-3 destination vector, pML3, to form a multigene construct. The Level-3 assembly proceeds by alternating Golden Gate reactions with TUs assembled in "W" and "B" pML2 vectors. Thus, the plasmid produced after each round of assembly becomes the destination vector for the next round of assembly. Three rounds of MIDAS Level-3 assembly are shown. Shown at the top of the figure is the Golden Gate cassette ([CATT]AarI-lacZa-AarI[CGTA]) in the pML3 destination vector. At left are shown the MIDAS cassettes for three Level-2 entry clones (i.e., TUs assembled in pML2 shuttle vectors). TU1 and TU3 are both shown assembled in forward orientations in pML2(+)WF vectors, while TU2 is shown assembled in the reverse orientation in the pML2(+)BR vector. In the first round of Level-3 assembly, TU1 is moved from TU1:pML2(+)WF into pML3 by an AarI-mediated Golden Gate reaction (compatible sticky ends are shown by dashed lines) and white colonies on X-Gal-containing plates are analysed. The resultant plasmid (pML3:TU1) is shown to the right. In the next round, TU2 is moved from plasmid TU2:pML2(+)BR into pML3:TU1 by a BsmBI-mediated Golden Gate reaction, giving rise to a plasmid containing both TU1 and TU2 (pML3:TU1:TU2) and blue colonies are analysed. In the third round, TU3 is moved from TU3:pML2(+)WR into pML3:TU1:TU2 by AarI-mediated Golden Gate assembly and white colonies are analysed. Since the final multigene plasmid (pML3:TU1:TU2:TU3) contains two divergent BsmBI sites, the assembly circuit remains open for addition of further TUs. The order in which each TU was added to the multigene assembly is indicated by the ordinal numbering above each TU in the final multigene construct.

As illustrated in FIG. 4, the nesting and inversion of the restriction sites in the "B" and "W" vectors means that TUs (or GEs) assembled into "W" MIDAS cassettes can be inserted into "B" MIDAS cassettes using AarI-mediated restriction-ligation reactions and, conversely, TUs (or GEs) assembled into "B" MIDAS cassettes can be cloned into "W" MIDAS cassettes using BsmBI-mediated restriction-ligation reactions. This cycle of cloning (i.e., alternating between "W" and "B" pML2 entry clones) can be repeated indefinitely. A skilled worker appreciates that other Type IIS restriction enzyme recognition sites may be used in accordance with the present invention. The use of such other Type IIS restriction enzyme recognition sites is specifically contemplated herein.

The cloning cassette found in the Level-3 destination vector, pML3, consists of a lacZα gene flanked by divergent AarI sites: [CATT]AarI-lacZa-AarI[CGTA], so the MIDAS Level-3 assembly is initiated (i.e., the first TU or GE is added) using an AarI-mediated restriction-ligation reaction between pML3 and a TU (or GE) that has been assembled into a pML2 "W" shuttle vector (FIG. 4). The plasmid generated is then used in a BsmBI-mediated restriction-ligation reaction with a TU cloned into a pML2 "B" shuttle vector. Further TUs are added by following this approach of alternating between AarI- and BsmBI-mediated restriction-ligation reactions using pML2 "W" and pML2 "B" entry clones, respectively. Thus, each plasmid generated by cloning a TU into the multigene construct becomes the destination vector for the next cycle of TU addition (FIG. 4).

Figure 5:
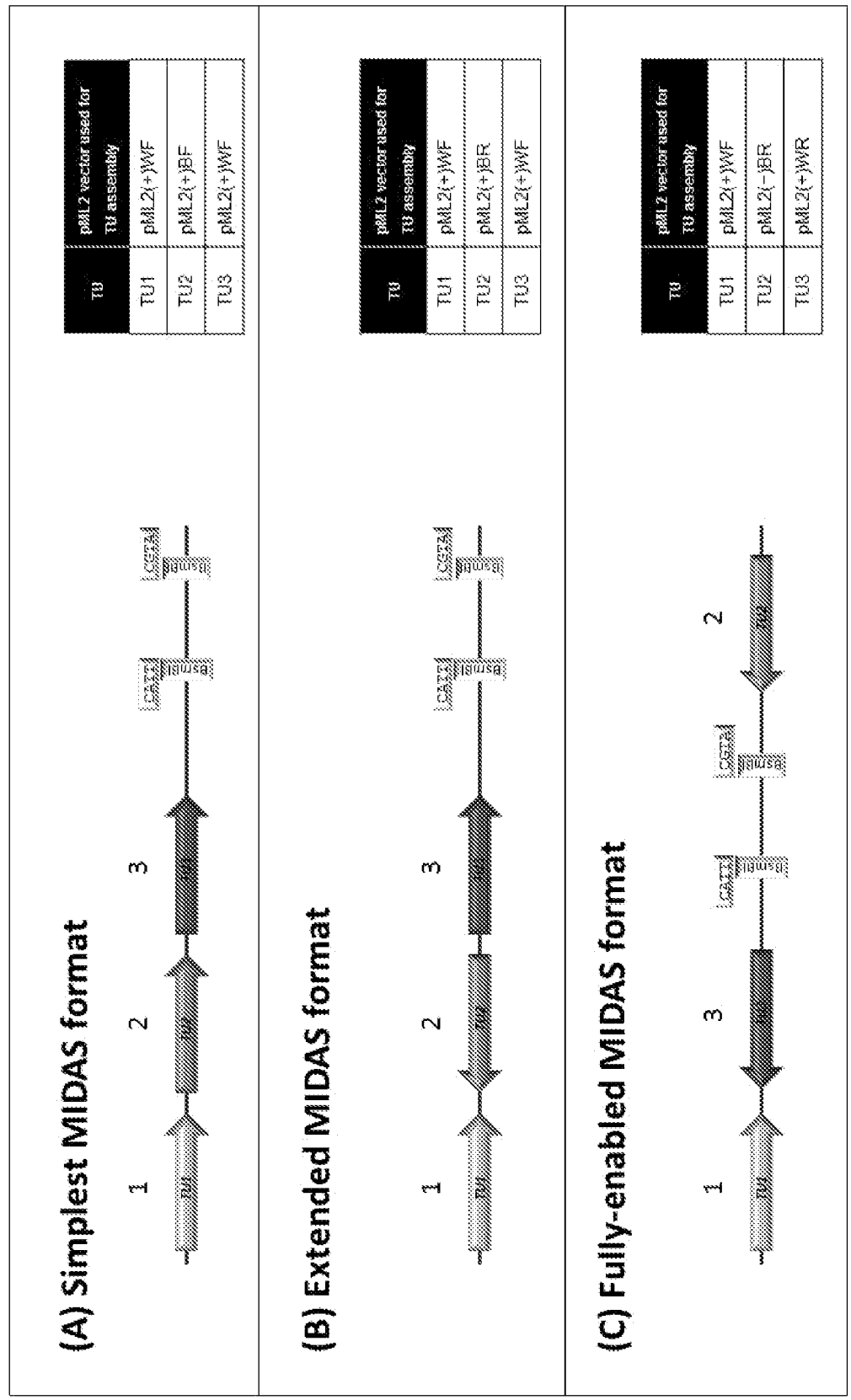
FIG. 5. MIDAS pML2 shuttle vectors allow control over the order, orientation and polarity of assembly of TUs in the multigene plasmid produced at Level-3. The figure schematically shows the configurations of three TUs in hypothetical multigene plasmids produced according to each of the MIDAS formats, with the tables showing the pML2 plasmids used to assemble each TU. (A) The simplest MIDAS format will produce multigene plasmids (at Level-3) using only two pML2 shuttle vectors to assemble TUs at Level-2—one "W" vector (pML2(+)WF) and its "B" counterpart (pML2(+)BF). The TUs are all in the same orientation (Forward) and the multigene plasmids can only be assembled in one direction (i.e., further TUs are added to the right of the last added TU). (B) The extended MIDAS format uses four pML2 shuttle vectors as the basis for producing multigene plasmids—a "W-Forward" vector (pML2(+)WF) and its "B" counterpart (pML2(+)BF), and a "W-Reverse" vector (pML2(+)WR) and its "B" counterpart (pML2(+)BR). TUs can be transcribed in either Forward or Reverse orientation but, as with the simplest MIDAS format described in (A), multigene assemblies can still only be constructed in one direction. (C) The full MIDAS format uses eight pML2 shuttle vectors—the four "Plus" (+) vectors described in (B) and their four "Minus" (−) polarity counterparts—permitting full user control over: the order of multigene assembly (through choice of "W" and "B" vectors), TU orientation (by using Forward or Reverse vectors) and polarity of multigene assembly (by using (+) or (−) vectors).

In its simplest configuration, MIDAS can achieve multi-gene assembly using only two pML2 shuttle vectors: one "W" vector and one "B" vector (FIG. 5A). However, use of the full set of eight pML2 shuttle vectors enables maximum user control over: (i) the order in which each TU is added to the growing multigene construct, (ii) the desired orientation (that is, the direction of transcription) of each TU and (iii) the polarity of assembly, i.e., the direction in which incoming TUs are loaded into the multigene construct.

Firstly, and as described earlier, the order of addition of each TU to the growing multigene construct is governed by the choice of "W" or "B" pML2 shuttle vector into which the TUs are assembled.

Secondly, and as described previously when discussing the Level-2 features, the orientation (direction of transcription) of a TU can be freely defined by the choice of "Forward" or "Reverse" pML2 vector into which the TU is assembled. Extending MIDAS to include the option of assembling TUs in either orientation expands the vector suite to four pML2 plasmids (see FIG. 3 and FIG. 5B).

Figure 3:
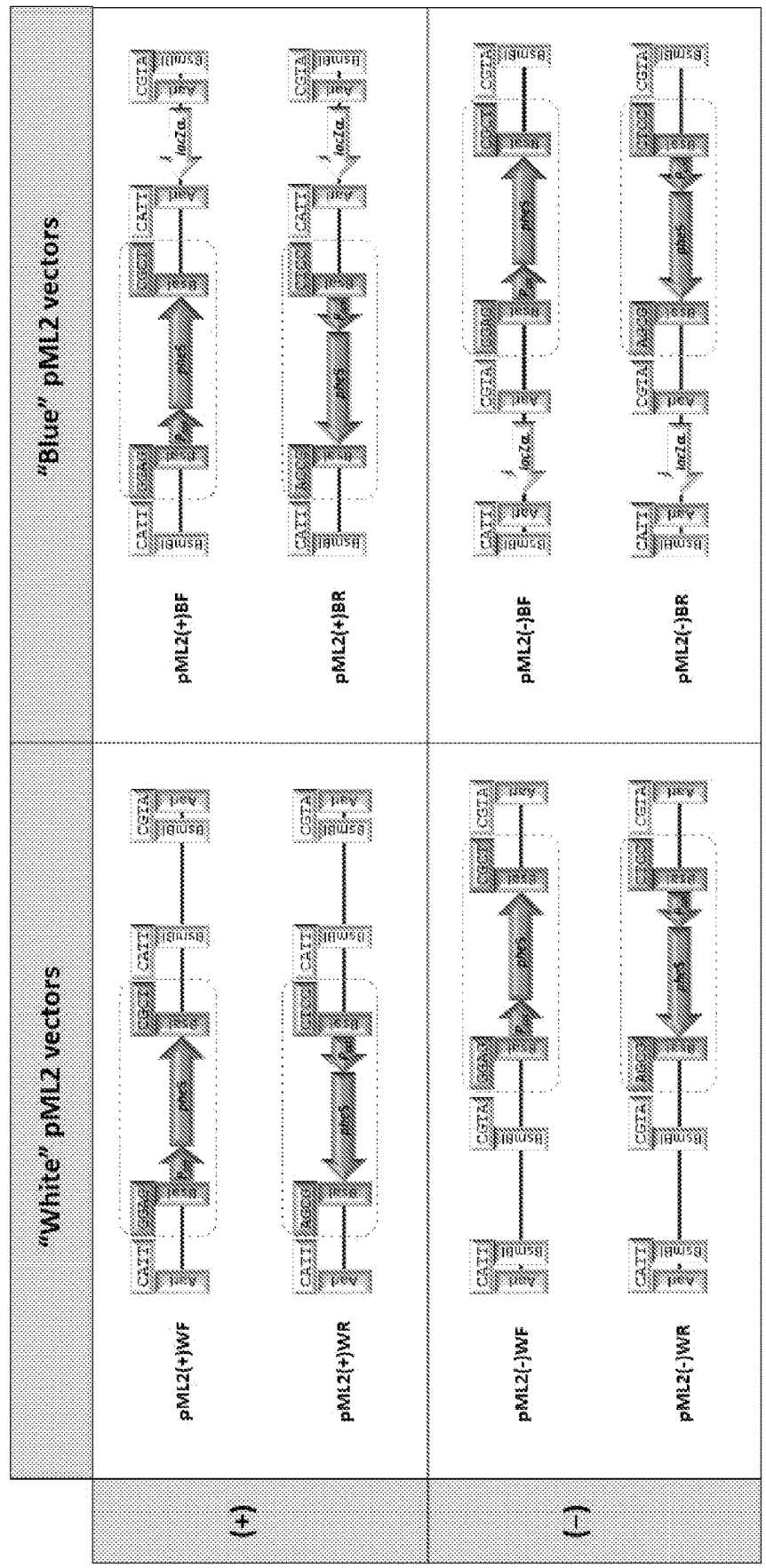
FIG. 3. Overview of MIDAS cassettes. The structure of the MIDAS cassette in each of the eight pML2 shuttle vectors is depicted schematically. Within each MIDAS cassette, the dashed box shows the Golden Gate cloning cassette (comprised of divergent BsaI sites flanking a pheS negative selection marker). The MIDAS cassettes in the pML2 "W" vectors (indicated by "W" in the plasmid name) are shown in the left panels, and those in the "B" vectors (indicated by "B" in the plasmid name) are shown in the right panels. The pML2 "Forward" vectors (indicated by the "F" suffix in the plasmid name) have their BsaI recognition sites (for Golden Gate assembly of TUs) switched relative to the BsaI fusion sites in the pML2 "Reverse" vectors, which are indicated by the "R" suffix in the plasmid name. pML2 (+) vectors are shown in the upper half of the figure, and pML2(−) vectors in the lower panel. The choice of (+) or (−) vector determines the direction in which new TUs (or GEs) are added to the growing multigene assembly produced at Level-3.

Thirdly, the polarity of multigene assembly (i.e., the direction in which new TUs are added to the growing multigene assembly) can also be freely defined—in this case by assembling TUs in pML2 shuttle vectors of either "plus" (+) or "minus" (−) polarity (FIG. 3). The use of a pML2(+) entry clone for Level-3 assembly ensures that the TU (or GE) added next will be added in the same direction as the direction of transcription of the Spec$^R$ gene found in pML3, i.e. the TU (or GE) assembled next in the multigene construct will be added to the right of the TU (or GE) that was added using the pML2(+) entry clone (as illustrated in FIG. 5A and FIG. 5B). In contrast, use of a pML2(−) entry clone for Level-3 assembly forces the next TU (or GE) to be added in the direction opposite to that of the direction of transcription of the Spec$^R$ gene found in pML3, so that the next TU (or GE) loaded into the multigene construct will be added to the left of the TU (or GE) that was added using the pML2(−) entry clone. In both these cases (i.e., sole use of either (+) or (−) entry clones), the assembly of multigene constructs at Level-3 is constrained to unidirectionality.

If, however, entry clones of both polarity (i.e., both pML2(+) and pML2(−)) are used to build the multigene construct, MIDAS has the ability to control the direction in which new TUs (or GEs) are added to the Level-3 assembly (FIG. 5C), and multigene assembly at Level-3 can be bidirectional. Examples where this feature is beneficial include testing expression of TUs intended to be integrated by homologous recombination into the chromosome of an expression host, or assessing TU expression in plants via Agrobacterium-mediated transformation, but not limited thereto. In both cases, the TUs to be expressed need to be placed between flanking GEs—left and right homology arms in the case of homologous recombination, or T-DNA left and right borders in the case of the plant expression example. This can easily be achieved using MIDAS, by ensuring that these GEs are loaded into the multigene construct from pML2 vectors of opposite polarity—one GE added using a pML2(+) entry clone, the other using a pML2(−) entry clone. This effectively turns pML3 into a vector suitable for homologous recombination (or, following prior assembly of an origin of replication to ensure plasmid propagation in Agrobacterium, into a vector suitable for Agrobacterium-mediated plant transformation), at the same time leaving the multigene assembly open for addition of the TUs of interest. All that remains is for each of the TUs of interest to be sequentially loaded into the vector, where they become positioned between the homology arms (or T-DNA borders). This strategy has the added flexibility of permitting the first TU (and all successive TUs) added between the homology arms (or T-DNA borders) to be assayed for expression after each cycle of TU addition into the multigene construct.

Described herein is MIDAS cloning performed using E. coli as the cloning host. However, the MIDAS platform is not so limited. Rather, the MIDAS platform is designed to permit incorporation of genetic elements (GEs) that allow biosynthetic pathway construction in any heterologous host of choice. By way of non-limiting example, incorporation of the yeast 2p origin of replication into pML3 would allow episomal replication of the multigene plasmid in yeast-based expression systems. In another non-limiting example, incorporation of T-DNA left and right borders and an origin of replication to ensure plasmid propagation in Agrobacterium would permit the use of Agrobacterium-mediated transformation of plant tissue, whilst incorporation of an SV40 origin of replication would permit expression in mammalian cell lines harbouring the SV40 large T antigen.

Accordingly in a first aspect the present invention relates to a vector set comprising at least two shuttle vectors, V1 and V2, wherein V1 is selected from the group consisting of
V1.1(+)=5'-A1 B1 M1 B2 C1 C2 A2-3',
V1.2(−)=5'-A1 C1 C2 B1 M1 B2 A2-3',
V1.3(+)=5'-A1 B2 M1 B1 C1 C2 A2-3', and
V1.4(−)=5'-A1 C1 C2 B2 M1 B1 A2-3', and V2 is selected from the group consisting of
V2.1(+)=5'-C1 B1 M1 B2 A1 M2 A2 C2-3',
V2.2(−)=5'-C1 A1 M2 A2 B1 M1 B2 C2-3',
V2.3(+)=5'-C1 B2 M1 B1 A1 M2 A2 C2-3', and
V2.4(−)=5'-C1 A1 M2 A2 B2 M1 B1 C2-3', wherein M1 is a first marker, M2 is a second marker, and A1, A2, B1, B2, C1 and C2 are restriction enzyme recognition sites, wherein at least A1, A2, C1, and C2 are recognition sites for Type IIS restriction enzymes, wherein A1, B1 and C1 are all different recognition sites, and wherein A1=A2, C1=C2, and B1=B2 or B1≠B2.

In one embodiment, when V1 is V1.1(+) or V1.3(+), V2 is V2.2(−) or V2.4(−).

In one embodiment, when V1 is V1.2(−) or V1.4(−), V2 is V2.1(+) or V2.3(+).

In one embodiment the vector set consists essentially of the at least two shuttle vectors.

In one embodiment A1, A2, B1, B2, C1 and C2 comprise at least four, preferably six, Type IIS restriction sites. In one embodiment the Type IIS restriction sites are selected from the group consisting of BsaI, AarI, BsmBI, AcuI, AlwI, BaeI, BbsI, BbvI, BccI, BceAI, BcgI, BciVI, BcoDI, BfuAI, BmrI, BpmI, BpuEI, BsaXI, BseRI, BsgI, BsmAI, BsmFI, BsmI, BspCNI, BspMI, BspQI, BsrDI, BsrI, BtgZI, BtsCI, BtsI, BtsIMutI, CspCI, EarI, EciI, FauI, FokI, HgaI, HphI, HpyAV, MboII, MlyI, MmeI, MnlI, NmeAIII, PleI, SapI, SfaNI sites. In one embodiment A1 and A2 are AarI restriction sites. In one embodiment B1 and B2 are BsaI restriction sites. In one embodiment C1 and C2 are BsmBI restriction sites.

In one embodiment the vector set further comprises a source vector.

In one embodiment the vector set further comprises a destination vector. In one embodiment the destination vector comprises a pair of restriction sites that are the same as A1 and A2 or as C1 and C2. In one embodiment the destination vector comprises a marker (DM) flanked by the pair of restriction sites. Preferably DM is the same as M2 in the V2 shuttle vectors. In one embodiment the destination vector does not comprise a DM.

In one embodiment the vector set comprises at least four, preferably at least five, preferably at least six, preferably at least seven, preferably eight different shuttle vectors.

In one embodiment the vector set consists essentially of at least four, preferably at least five, preferably at least six, preferably at least seven, preferably eight different shuttle vectors.

In one embodiment the vector set comprises at least four shuttle vectors as follows:
 (a) at least two V1 vectors and at least two V2 vectors,
 (b) at least one V1 vector and at least three V2 vectors, or
 (c) at least three V1 vectors and at least one V2 vector,
  wherein each of (a), (b) and (c) comprises at least one (−) vector and at least one (+) vector.

In one embodiment the vector set comprises at least five shuttle vectors as follows:
 (d) at least two V1 vectors and at least three V2 vectors,
 (e) at least three V1 vectors and at least two V2 vectors,
 (f) four V1 vectors and at least one V2 vector, or
 (g) at least one V1 vector and four V2 vectors,
  wherein each of (d), (e), (f) and (g) comprises at least one (−) vector and at least one (+) vector.

In one embodiment the vector set comprises at least six shuttle vectors as follows:
 (h) at least three V1 vectors and at least three V2 vectors,
 (i) four V1 vectors and at least two V2 vectors,
 (j) at least two V1 vectors and four V2 vectors,
  wherein each of (i) and (j) comprises at least one (−) vector and at least one (+) vector.

In one embodiment the vector set comprises at least seven shuttle vectors as follows:
 (k) at least three V1 vectors and four V2 vectors,
 (l) four V1 vectors and at least three V2 vectors.

In one embodiment the vector set comprises V1.1(+), V1.2(−), V1.3(+), V1.4(−), V2.1(+), V2.2(−), V2.3(+) and V2.4(−).

In one embodiment the vector set consists essentially of V1.1(+), V1.2(−), V1.3(+), V1.4(−), V2.1(+), V2.2(−), V2.3(+) and V2.4(−).

In one embodiment the shuttle vector is a vector selected from the group consisting of plasmids, bacteriophage, phagemids, cosmids, fosmids, bacterial artificial chromosomes, yeast artificial chromosomes, and phage artificial chromosomes. In one embodiment the shuttle vector is a plasmid.

In one embodiment M1 is a scorable marker or a selectable marker. Preferably M1 is a selectable marker. In one embodiment the selectable marker is a polynucleotide encoding for antibiotic resistance. In one embodiment the antibiotic resistance is resistance to an antibiotic selected from the group consisting of kanamycin, chloramphenicol, tetracycline, streptomycin, spectinomycin, ampicillin, carbenicillin, nalidixic acid, amphotericin B, erythromycin, gentamycin, neomycin, nystatin.

In one embodiment the selectable marker is a gene that encodes a peptide that confers lethality on a cell or organism containing the marker, for example when the gene encoding the peptide is transformed into an appropriate cell, or when the cell or organism is grown under the appropriate conditions. In one embodiment the marker is selected from a group consisting of ccdB, pheS, rpsL, sacB. In one embodiment the marker is a mutant *E. coli* pheS selectable marker operably linked to a promoter, preferably an *E. coli* promoter, preferably the *E. coli* chloramphenicol acetyltransferase promoter. In one embodiment the mutant *E. coli* pheS selectable marker is a Thr$^{251}$Ala/Ala$^{294}$Gly double mutant.

In one embodiment M2 encodes a selectable marker or a scorable marker. In one embodiment the scorable marker is either a fluorescent marker selected from a group consisting of GFP, eGFP, YFP, DsRed, DsRed2, mCherry, or is a bioluminescent marker such as luciferase, or is a chromogenic marker selected from a list consisting of the gene encoding LacZ, β-glucuronidase or β-glucosidase, or the set of genes encoding CrtE, CrtB, CrtI, CrtY and CrtW (collectively called CRed) or encoding napthalene dioxygenase. Preferably the marker is a chromogenic marker, preferably a LacZ marker.

In one embodiment V1.1(+) is pML2(+)WF comprising SEQ ID NO: 122. In one embodiment pML2(+)WF consists essentially of SEQ ID NO: 122.

In one embodiment V1.2(−) is pML2(−)WR comprising SEQ ID NO: 123. In one embodiment pML2(−)WR consists essentially of SEQ ID NO: 123.

In one embodiment V1.3(+) is pML2(+)WR comprising SEQ ID NO: 124. In one embodiment pML2(+)WR consists essentially of SEQ ID NO: 124.

In one embodiment V1.4(−) is pML2(−)WF comprising SEQ ID NO: 125. In one embodiment pML2(−)WF consists essentially of SEQ ID NO: 125.

In one embodiment V2.1(+) is pML2(+)BF comprising SEQ ID NO: 126. In one embodiment pML2(+)BF consists essentially of SEQ ID NO: 126.

In one embodiment V2.2(−) is pML2(−)BR comprising SEQ ID NO: 127. In one embodiment pML2(−)BR consists essentially of SEQ ID NO: 127.

In one embodiment V2.3(+) is pML2(+)BR comprising SEQ ID NO: 128. In one embodiment pML2(+)BR consists essentially of SEQ ID NO: 128.

In one embodiment V2.4(−) is pML2(−)BF comprising SEQ ID NO: 129. In one embodiment pML2(−)BF consists essentially of SEQ ID NO: 129.

In one embodiment A1 and A2 are in a convergent orientation relative to each other in V1.1(+), V1.2(−), V1.3(+) and V1.4(−).

In one embodiment A1 and A2 are in a divergent orientation relative to each other in V2.1(+), V2.2(−), V2.3(+) and V2.4(−).

In one embodiment C1 and C2 are in a divergent orientation relative to each other in V1.1(+), V1.2(−), V1.3(+) and V1.4(−).

In one embodiment C1 and C2 are in a convergent orientation relative to each other in V2.1(+), V2.2(−), V2.3(+) and V2.4(−).

In one embodiment the vectors in the vector set are components in a cloning system.

In one embodiment the cloning system is useful for making a gene construct comprising at least one transcription unit (TU).

In one embodiment the vector set comprises part of a cloning system. In one embodiment the cloning system is useful for making a gene construct comprising at least one TU.

In one embodiment V1.1(+), V1.2(−), V1.3(+), V1.4(−), V2.1(+), V2.2(−), V2.3(+) or V2.4(−), or any combination thereof comprises at least two vectors, one V1 vector and one V2 vector, wherein at least one vector is a (+) vector and one vector is a (−) vector, are components in a cloning system.

In one embodiment the cloning system is useful for making a gene construct comprising at least one TU.

In one embodiment the gene construct is a multigene construct comprising at least two TUs. In one embodiment the multigene construct comprises at least three, preferably at least four, preferably at least five, preferably at least six, preferably at least seven, preferably at least eight, preferably at least nine, preferably at least ten TUs.

In one embodiment the multigene construct comprises, consists essentially or consists of at least one, preferably two, preferably three, preferably four, preferably five, preferably six, preferably seven, preferably eight, preferably nine, preferably at least ten TU's from a biosynthetic pathway.

In one embodiment the multigene construct comprises, consists essentially or consists of a complete biosynthetic pathway.

In one embodiment the biosynthetic pathway is a microbial, preferably fungal biosynthetic pathway.

In one embodiment the biosynthetic pathway is an indole diterpene biosynthetic pathway.

In one embodiment the indole diterpene biosynthetic pathway comprises, consists essentially of, or consists of at least one, preferably two, preferably three, preferably four genes required for the production of paspaline. In one embodiment the genes required for the production of paspaline comprise at least one of paxG, paxM, paxB and paxC, preferably at least two, preferably at least three, preferably all four of paxG, paxM, paxB and paxC. Preferably the genes required for the production of paspaline are from *Penicillium* spp, preferably *P. paxilli*.

In one embodiment the indole diterpene biosynthetic pathway comprises, consists essentially of, or consists of at least one, preferably two, preferably three, preferably four, preferably five, preferably six genes required for the production of paxilline. In one embodiment the genes required for the production of paxilline comprise at least one of paxG, paxM, paxB, paxC, paxQ and paxP, preferably at least two, preferably at least three, preferably at least four, preferably at least five, preferably all six of paxG, paxM, paxB, paxC, paxQ and paxP. Preferably the genes required for the production of paxiline are from *Penicillium* spp, preferably *P. paxilli*.

In one embodiment the biosynthetic is a naturally occurring biosynthetic pathway. In one embodiment the biosynthetic pathway is an artificial biosynthetic pathway.

In one embodiment the gene construct and/or multi gene construct is made by cloning a TU from a shuttle vector into the destination vector.

In one embodiment the TU is added into the destination vector by cloning into a pair of restriction sites that is the same as a pair of restriction sites on a shuttle vector.

In one embodiment the TU is added into the destination vector in either of two directions relative to another transcription unit present in the destination vector.

In one embodiment the TU is added into the destination vector in a position 5' of another transcription unit already present in the destination vector.

In one embodiment the TU is added in to the destination vector in a position 3' of another transcription unit already present in the destination vector.

In one embodiment the TU is added in a 5' to 3' or 3' to 5' orientation in the destination vector.

In one embodiment the vector set comprises at least one destination vector, the destination vector comprising a marker comprising flanking restriction sites, wherein the flanking restriction sites are the same as one of the first (A1, A2) or third (C1, C2) pair of restriction sites on the at least two shuttle vectors.

In one embodiment the flanking restriction sites are the same as A1 and A2. Preferably A1 and A2 are a pair of Type IIS restriction sites. Preferably A1 and A2 are AarI or BsmBI restriction sites. Preferably B1 and B2 are Type IIS restriction sites. Preferably C1 and C2 are Type IIS restriction sites. Preferably A1, A2, B1 and B2, preferably A1, A2, C1 and C2, preferably B1, B2, C1 and C2, preferably A1, A2, B1, B2, C1 and C2 are Type IIS restriction sites. Preferably the Type IIS restriction sites are selected from the group consisting of BsaI, AarI, BsmBI, AcuI, AlwI, BaeI, BbsI, BbvI, BccI, BceAI, BcgI, BciVI, BcoDI, BfuAI, BmrI, BpmI, BpuEI, BsaXI, BseRI, BsgI, BsmAI, BsmFI, BsmI, BspCNI, BspMI, BspQI, BsrDI, BsrI, BtgZI, BtsCI, BtsI, BtsIMutI, CspCI, EarI, EciI, FauI, FokI, HgaI, HphI, HpyAV, MboII, MlyI, MmeI, MnlI, NmeAIII, PleI, SapI, SfaNI sites.

In one embodiment the vector set comprises at least one source vector comprising a polynucleotide sequence encoding at least one marker flanked by two divergent restriction sites. Preferably the divergent restriction sites are Type IIS restriction sites. Preferably the Type IIS restriction sites are selected from the group consisting of BsaI, AarI, BsmBI, AcuI, AlwI, BaeI, BbsI, BbvI, BccI, BceAI, BcgI, BciVI, BcoDI, BfuAI, BmrI, BpmI, BpuEI, BsaXI, BseRI, BsgI, BsmAI, BsmFI, BsmI, BspCNI, BspMI, BspQI, BsrDI, BsrI, BtgZI, BtsCI, BtsI, BtsIMutI, CspCI, EarI, EciI, FauI, FokI, HgaI, HphI, HpyAV, MboII, MlyI, MmeI, MnlI, NmeAIII, PleI, SapI, SfaNI sites. Preferably the Type IIS restriction sites are BsmBI sites.

In one embodiment the marker in the at least one destination vector or the at least one source vector, or both is a selectable marker or scorable marker. In one embodiment the marker is selectable marker. In one embodiment the selectable marker is a polynucleotide encoding for antibiotic resistance. In one embodiment the antibiotic resistance is resistance to an antibiotic selected from the group consisting of kanamycin, chloramphenicol, tetracycline, streptomycin, spectinomycin, ampicillin, carbenicillin, nalidixic acid, amphotericin B, erythromycin, gentamycin, neomycin andnystatin.

In one embodiment the selectable marker is a gene that encodes a peptide that confers lethality on a cell or organism containing the marker, for example when the gene encoding the peptide is transformed into an appropriate cell, or when the cell or organism is grown under the appropriate conditions. In one embodiment the marker is selected from a group consisting of ccdB, pheS, rpsL, sacB. In one embodiment the marker is a mutant *E. coli* pheS selectable marker operably linked to a promoter, preferably an *E. coli* promoter, preferably the *E. coli* chloramphenicol acetyltransferase promoter. In one embodiment the mutant *E. coli* pheS selectable marker is a Thr$^{251}$Ala/Ala$^{294}$Gly double mutant.

In one embodiment the marker is a scorable marker. In one embodiment the scorable marker is either a fluorescent marker selected from a group consisting of GFP, eGFP, YFP, DsRed, DsRed2, mCherry, or is a bioluminescent marker such as luciferase, or is a chromogenic marker selected from a list consisting of the gene encoding LacZ, β-glucuronidase or β-glucosidase, or the set of genes encoding CrtE, CrtB, CrtI, CrtY and CrtW (collectively called CRed) or encoding napthalene dioxygenase. Preferably the marker is a chromogenic marker, preferably a LacZ marker.

In another aspect the present invention relates to a vector set comprising at least three shuttle vectors,
wherein at least two of the three vectors are V1 vectors selected from the group consisting of
V1.1(+)=5'-A1 B1 M1 B2 C1 C2 A2-3',
V1.2(−)=5'-A1 C1 C2 B1 M1 B2 A2-3',
V1.3(+)=5'-A1 B2 M1 B1 C1 C2 A2-3', and
V1.4(−−)=5'-A1 C1 C2 B2 M1 B1 A2-3',
wherein at least one of the V1 vectors is a (+) vector and another V1 vector is a (−) vector,
and wherein at least one of the three vectors is a V2 vector selected from the group consisting of
V2.1(+)=5'-C1 B1 M1 B2 A1 M2 A2 C2-3',
V2.2(−)=5'-C1 A1 M2 A2 B1 M1 B2 C2-3',
V2.3(+)=5'-C1 B2 M1 B1 A1 M2 A2 C2-3', and
V2.4(−)=5'-C1 A1 M2 A2 B2 M1 B1 C2-3',
wherein M1 is a first marker, M2 is a second marker, and A1, A2, B1, B2, C1 and C2 are restriction enzyme recognition sites,
wherein at least A1, A2, C1, and C2 are recognition sites for Type IIS restriction enzymes,
wherein A1, B1 and C1 are all different restriction sites, and
wherein A1=A2, C1=C2, and B1=B2 or B1≠B2.
In one embodiment, when the V1 vectors are
V1.1(+) and V1.2(−), or
V1.1(+) and V1.4(−), or
V1.2(−) and V1.3(+), or
V1.3(+) and V1.4(−), then
the V2 vector is selected from the group consisting of V2.1(+), V2.2(−), V2.3(+) and V2.4(−).
In one embodiment, when the at least two V1 vectors are V1.1(+) and V1.3(+), then V2 is V2.2(−) or V2.4(−).
In one embodiment, when the at least two V1 vectors are V1.2(−) and V1.4(−), then V2 is V2.1(+) or V2.3(+).
In one embodiment the vector set consists essentially of the at least three vectors.

Specifically contemplated for this aspect of the invention are the various embodiments of the invention relating to restriction sites A1, A2, B1, B2, C1 and C2, source vectors, shuttle vectors, destination vectors and markers including M1 and M2, as described herein for the first aspect of the invention.

In various embodiments specifically contemplated for this aspect of the invention the vector set comprises or consists essentially of the at least four shuttle vectors, at least five shuttle vectors, at least six shuttle vectors, or at least seven shuttle vectors set out in the various combinations (a), (b), (c), (d), (e), (f), (g), (h), (i), (j), (k) and (l) as described herein for the first aspect of the invention.

In one embodiment the vector set comprises V1.1(+), V1.2(−), V1.3(+), V1.4(−), V2.1(+), V2.2(−), V2.3(+) and V2.4(−).

In one embodiment the vector set consists essentially of V1.1(+), V1.2(−), V1.3(+), V1.4(−), V2.1(+), V2.2(−), V2.3(+) and V2.4(−).

In various embodiments specifically contemplated for this aspect of the invention, V1.1(+), V1.2(−), V1.3(+), V1.4(−), V2.1(+), V2.2(−), V2.3(+) and V2.4(−) are pML2(+)WF, pML2(−)WR, pML2(+)WR, pML2(−)WF, pML2(+)BF, pML2(−)BR, pML2(+)BR, and pML2(−)BF respectively comprising or consisting essentially of SEQ ID NO: 122, 123, 124, 125, 126, 127, 128 and 129 as defined for the first aspect of the invention as described herein.

In various embodiments specifically contemplated for this aspect of the invention, A1, A2, C1 and C2 are in divergent or convergent orientations relative to each other as described herein for V1.1(+), V1.2(−), V1.3(+), V1.4(−), V2.1(+), V2.2(−), V2.3(+) and V2.4(−) in accordance with the first aspect of the invention.

In various embodiments specifically contemplated for this aspect of the invention, the vectors in the vector set are components in a cloning system, or comprise part of a cloning system useful for making a gene and/or multigene construct as described for the first aspect of the invention.

In various embodiments specifically contemplated for this aspect of the invention, a gene construct and/or multigene construct is/are as described herein for the first aspect of the invention. Additionally, in various embodiments specifically contemplated for this aspect of the invention, a gene construct and/or multi gene construct is/are made, and a TU is, or multiple TUs are, added into the destination vector as described herein for the first aspect of the invention.

In another aspect the present invention relates to a vector set comprising at least three shuttle vectors,
wherein at least one of the three vectors is a V1 selected from the group consisting of
V1.1(+)=5'-A1 B1 M1 B2 C1 C2 A2-3',
V1.2(−)=5'-A1 C1 C2 B1 M1 B2 A2-3',
V1.3(+)=5'-A1 B2 M1 B1 C1 C2 A2-3', and
V1.4(−)=5'-A1 C1 C2 B2 M1 B1 A2-3',
and at least two of the three vectors are a V2 vector selected from the group consisting of
V2.1(+)=5'-C1 B1 M1 B2 A1 M2 A2 C2-3',
V2.2(−)=5'-C1 A1 M2 A2 B1 M1 B2 C2-3',
V2.3(+)=5'-C1 B2 M1 B1 A1 M2 A2 C2-3', and
V2.4(−)=5'-C1 A1 M2 A2 B2 M1 B1 C2-3',
wherein at least one of the V2 vectors is a (+) vector and another V2 vector is a (−) vector,
wherein M1 is a first marker, M2 is a second marker, and A1, A2, B1, B2, C1 and C2 are restriction enzyme recognition sites,
wherein at least A1, A2, C1, and C2 are recognition sites for Type IIS restriction enzymes,
wherein A1, B1 and C1 are all different restriction sites, and
wherein A1=A2, C1=C2, and B1=B2 or B1≠B2.
In one embodiment, when the V2 vectors are
V2.1(+) and V2.2(−), or
V2.1(+) and V2.4(−), or
V2.2(−) and V2.3(+), or
V2.3(+) and V2.4(−), then
the V1 vector is selected from the group consisting of V1.1(+), V1.2(−), V1.3(+) and V1.4(−).
In one embodiment, when the at least two V2 vectors are V2.1(+) or V2.3(+), then V1 is V1.2(−) or V1.4(−).
In one embodiment, when the at least two V2 vectors are V2.2(−) or V2.4(−), then V1 is V1.1(+) or V1.3(+).
In one embodiment the vector set consists essentially of the at least three vectors.

Specifically contemplated for this aspect of the invention are the various embodiments of the invention relating to restriction sites A1, A2, B1, B2, C1 and C2, source vectors, shuttle vectors, destination vectors and markers including M1 and M2, as described herein for the first aspect of the invention.

In various embodiments specifically contemplated for this aspect of the invention the vector set comprises or consists essentially of the at least four shuttle vectors, at least five shuttle vectors, at least six shuttle vectors, or at least seven shuttle vectors set out in the various combinations (a), (b), (c), (d), (e), (f), (g), (h), (i), (j), (k) and (l) as described herein for the first aspect of the invention.

In one embodiment the vector set comprises V1.1(+), V1.2(−), V1.3(+), V1.4(−), V2.1(+), V2.2(−), V2.3(+) and V2.4(−).

In one embodiment the vector set consists essentially of V1.1(+), V1.2(−), V1.3(+), V1.4(−), V2.1(+), V2.2(−), V2.3 (+) and V2.4(−).

In various embodiments specifically contemplated for this aspect of the invention, V1.1(+), V1.2(−), V1.3(+), V1.4(−), V2.1(+), V2.2(−), V2.3(+) and V2.4(−) are pML2(+)WF, pML2(−)WR, pML2(+)WR, pML2(−)WF, pML2(+)BF, pML2(−)BR, pML2(+)BR, and pML2(−)BF respectively comprising or consisting essentially of SEQ ID NO: 122, 123, 124, 125, 126, 127, 128 and 129 as defined for the first aspect of the invention as described herein.

In various embodiments specifically contemplated for this aspect of the invention, A1, A2, C1 and C2 are in divergent or convergent orientations relative to each other as described herein for V1.1(+), V1.2(−), V1.3(+), V1.4(−), V2.1(+), V2.2(−), V2.3(+) and V2.4(−) in accordance with the first aspect of the invention.

In various embodiments specifically contemplated for this aspect of the invention, the vectors in the vector set are components in a cloning system, or comprise part of a cloning system useful for making a gene and/or multigene construct as described for the first aspect of the invention.

In various embodiments specifically contemplated for this aspect of the invention, a gene construct and/or multigene construct is/are as described herein for the first aspect of the invention. Additionally, in various embodiments specifically contemplated for this aspect of the invention, a gene construct and/or multi gene construct is/are made, and a TU is, or multiple TUs are, added into the destination vector as described herein for the first aspect of the invention.

In another aspect the present invention relates to a vector set comprising at least two shuttle vectors, wherein
  each shuttle vector comprises a first marker (M1), and at least six restriction sites, wherein at least four of the restriction sites are Type IIS restriction sites,
  wherein in at least one first shuttle vector, a first four restriction sites are located 3' or 5' of M1, at least three of the four being Type IIS restriction sites, and a second two restriction sites are located 3' or 5' of M1, at least one of the two being a Type IIS restriction site, and
  wherein in at least one second shuttle vector, a first four restriction sites are located 3' or 5' of M1, at least three of the four being Type IIS restriction sites, and a second two restriction sites are located 5' or 3' of M1, at least one of the two being a Type IIS restriction site,
  wherein the at least one second shuttle vector comprises at least one second marker (M2) flanked by two Type IIS restriction sites, and
  wherein when the first four restriction sites are located 3' of M1 in the at least one first or second vector, the second two restriction sites are located 5' of M1, and the vector is a (+) vector, and
  when the first four restriction sites are located 5' of M1 in the at least one first or second vector, the second two restriction sites are located 3' of M1 and the vector is a (−) vector.

In one embodiment the set comprises at least three shuttle vectors
  wherein at least two shuttle vectors are first shuttle vectors, and at least one shuttle vector is a second shuttle vector, or
  wherein at least one shuttle vector is a first shuttle vector and at least two shuttle vectors are second shuttle vectors,
  wherein the three shuttle vectors comprise at least one (+) vector and at least one (−) vector.

In one embodiment the set comprises at least four shuttle vectors
  wherein at least two shuttle vectors are first shuttle vectors, and at least two shuttle vectors are second shuttle vectors,
  wherein the four shuttle vectors comprise at least one (+) vector and at least one (−) vector, preferably at least two (+) vectors and at least two (−) vectors.

In one embodiment the set comprises at least five shuttle vectors
  wherein at least two shuttle vectors are first shuttle vectors, and at least three shuttle vectors are second shuttle vectors, or
  wherein at least three shuttle vectors are first shuttle vectors, and at least two shuttle vectors are second shuttle vectors, or
  wherein the five shuttle vectors comprise at least one (+) vector and at least one (−) vector, preferably at least two (+) vectors and at least two (−) vectors.

In one embodiment the set comprises at least six shuttle vectors
  wherein at least three shuttle vectors are first shuttle vectors, and at least three shuttle vectors are second shuttle vectors,
  wherein the six shuttle vectors comprise at least one (+) vector and at least one (−) vector, preferably at least two (+) vectors and at least two (−) vectors, preferably at least three (+) vectors and at least three (−) vectors.

In one embodiment the set comprises at least seven shuttle vectors,
  wherein at least three shuttle vectors are first shuttle vectors, and at least three shuttle vectors are second shuttle vectors, or
  wherein four shuttle vectors are first shuttle vectors, and at least three shuttle vectors are second shuttle vectors,
  wherein the seven shuttle vectors comprise at least one (+) vector and at least one (−) vector, preferably at least two (+) vectors and at least two (−) vectors, preferably at least three (+) vectors and at least three (−) vectors.

In one embodiment the set comprises eight shuttle vectors comprising four first shuttle vectors and four second shuttle vectors,
  wherein the eight shuttle vectors comprise at least one (+) vector and at least one (−) vector, preferably at least two (+) vectors and at least two (−) vectors, preferably at least three (+) vectors and at least three (−) vectors, preferably four (+) vectors and four (−) vectors.

In one embodiment the vector set consists essentially of the eight shuttle vectors.

Specifically contemplated for this aspect of the invention are various embodiments of the invention relating to restriction sites, source vectors, shuttle vectors, destination vectors and markers including M1 and M2, as described herein for the first aspect of the invention.

In various embodiments specifically contemplated for this aspect of the invention, the first and second vectors in the vector set are components in a cloning system, or comprise part of a cloning system useful for making a gene and/or multigene construct as described for the first aspect of the invention.

In various embodiments specifically contemplated for this aspect of the invention, a gene construct and/or multigene construct is/are as described herein for the first aspect of the invention. Additionally, in various embodiments specifically contemplated for this aspect of the invention, a gene construct and/or multi gene construct is/are made, and a TU is, or multiple TUs are, added into the destination vector as described herein for the first aspect of the invention.

In another aspect the present invention relates to a set of eight shuttle vectors, each shuttle vector comprising a first marker (M1) and six restriction sites,
wherein each shuttle vector comprises a first set of four restriction sites positioned on one side of M1 and a second set of two restriction sites positioned on the other side of M1,
wherein
at least two of the restriction sites in the first set are the same as each other,
the two restriction sites in the second set are different from each other, at least one of the two restriction sites in the second set is the same as one of
the restriction sites in the first set, and
wherein four of the shuttle vectors comprise a second marker (M2),
wherein four of the vectors are (+) vectors comprising the first set of restriction sites 3' of M1, and four of the vectors are (−) vectors comprising the first set of restriction sites 5' of M1.

In one embodiment M1 or M2 or both are a selectable or scorable marker as described herein for any other aspect of the invention. In one embodiment M2 is located within the first set of restriction sites, preferably between a pair of restriction sites, preferably flanked by the pair of restriction sites. In one embodiment the pair of restriction sites are a pair of Type IIS restriction sites. Preferably the pair of Type IIS restriction sites are selected from the group consisting of BsaI, AarI, BsmBI, AcuI, AlwI, BaeI, BbsI, BbvI, BccI, BceAI, BcgI, BciVI, BcoDI, BfuAI, BmrI, BpmI, BpuEI, BsaXI, BseRI, BsgI, BsmAI, BsmFI, BsmI, BspCNI, BspMI, BspQI, BsrDI, BsrI, BtgZI, BtsCI, BtsI, BtsIMutI, CspCI, EarI, EciI, FauI, FokI, HgaI, HphI, HpyAV, MboII, MlyI, MmeI, MnlI, NmeAIII, PleI, SapI, SfaNI sites.

In one embodiment the six restriction sites comprise at least four, preferably six, Type IIS restriction sites. In one embodiment the Type IIS restriction sites are selected from the group consisting of BsaI, AarI, BsmBI, AcuI, AlwI, BaeI, BbsI, BbvI, BccI, BceAI, BcgI, BciVI, BcoDI, BfuAI, BmrI, BpmI, BpuEI, BsaXI, BseRI, BsgI, BsmAI, BsmFI, BsmI, BspCNI, BspMI, BspQI, BsrDI, BsrI, BtgZI, BtsCI, BtsI, BtsIMutI, CspCI, EarI, EciI, FauI, FokI, HgaI, HphI, HpyAV, MboII, MlyI, MmeI, MnlI, NmeAIII, PleI, SapI, SfaNI sites.

In various embodiments specifically contemplated for this aspect of the invention, the six restriction sites comprise A1, A2, B1, B2, C1 and C2 wherein A1, A2, B1, B2, C1 and C2 are restriction sites as described herein for any other aspect of the invention. In one embodiment the arrangement of A1, A2, B1, B2, C1 and C2 in at least one, preferably at least two, preferably at least three, preferably at least four, preferably at least five, preferably at least six, preferably at least seven, preferably all eight of the shuttle vectors, including relative to each other, is as described herein for any other aspect of the invention.

In one embodiment the arrangement of A1, A2, B1, B2, C1, C2 and the first marker (M1) in at least one, preferably at least two, preferably at least three, preferably at least four, preferably at least five, preferably at least six, preferably at least seven, preferably all eight of the shuttle vectors, including relative to each other, are as described herein for any other aspect of the invention.

In one embodiment the two restriction sites in the first set of restriction sites that are the same as each other are in divergent orientation relative to each other.

In one embodiment the one restriction sites in the first and second sets that are the same as each other are in a convergent orientation relative to each other.

In one embodiment the six restriction sites comprise three pairs of restriction sites, wherein in two pairs of the restriction sites, the restriction sites are in a divergent orientation relative to the other and in one pair of the restriction sites the restriction sites are in a convergent orientation relative to each other. In one embodiment the pair of restriction sites in a convergent orientation flank the two pairs of restriction sites having the divergent orientation.

In one embodiment the vector set comprises at least one destination vector, the destination vector comprising either a marker with flanking divergent restriction sites or divergent restriction sites and no marker, wherein the divergent restriction sites are, respectively, the same restriction sites as the one pair of restriction sites that are in a convergent orientation relative to each other in the four V1 shuttle vectors, or the same restriction sites as the one pair of restriction sites that are in a convergent orientation relative to each other in the four V2 shuttle vectors.

In one embodiment the vector set comprises at least one destination vector as described herein for any other aspect of the invention. In one embodiment the vector set comprises at least one source vector as described herein for any other aspect of the invention.

In various embodiments specifically contemplated for this aspect of the invention the vector set comprises or consists essentially of four V1 vectors and four V2 vectors as described herein for any other aspect of the invention. Preferably the four V1 and four V2 vectors consist of V1.1(+), V1.2(−), V1.3(+), V1.4(−), V2.1(+), V2.2(−), V2.3(+) and V2.4(−).

In various embodiments specifically contemplated for this aspect of the invention, the vectors in the vector set are components in a cloning system, or comprise part of a cloning system useful for making a gene and/or multigene construct as described for any other aspect of the invention.

In various embodiments specifically contemplated for this aspect of the invention, a gene construct and/or multigene construct is/are as described herein for any other aspect of the invention. Additionally, in various embodiments specifically contemplated for this aspect of the invention, a gene construct and/or multi gene construct is/are made, and a TU is, or multiple TUs are, added into the destination vector as described herein for any other aspect of the invention.

In one embodiment the vector set consists essentially of the eight shuttle vectors and the at least one destination vector. In one embodiment the vector set consists essentially of the eight shuttle vectors, the at least one destination vector, and at least one source vector. A skilled worker will appreciate that all embodiments set out herein regarding source, shuttle and destination vectors as described herein for any other aspect of the invention are also embodiments of the invention specifically contemplated for this aspect of the invention.

In another aspect the invention relates to a method of making a vector set comprising at least two shuttle vectors comprising combining at least one V1 shuttle vector or first shuttle vector of the invention with at least one V2 shuttle vector or second shuttle vector of the invention.

In one embodiment the at least one first or V1 vector is a (−) vector and the at least one second vector or V2 vector is a (+) vector.

In one embodiment the at least one first or V1 vector is a (+) vector and the at least one second vector or V2 vector is a (−) vector.

In one embodiment the method comprises combining at least two, preferably at least three, preferably four V1 shuttle vectors or first shuttle vectors as described herein with at least two, preferably at least three, preferably four V2 shuttle vectors or second shuttle vectors as described herein.

Specifically contemplated as embodiments of this aspect of the invention are V1 shuttle vectors, V2 shuttle vectors, first shuttle vectors and second shuttle vectors, including the types of markers and the types and arrangements of restriction sites, are as described herein for any other aspect of the invention.

In one embodiment the method comprises combining at least one destination vector as described herein with the shuttle vectors.

In one embodiment the method comprises combining at least one source vector as described herein with the shuttle vectors.

In one embodiment the method comprises combining at least one source vector and one destination vector with the shuttle vectors.

In various embodiments specifically contemplated for this aspect of the invention the method comprises or consists essentially of combining four V1 vectors and four V2 vectors as described herein for any other aspect of the invention. Preferably the four V1 and four V2 vectors consist of V1.1(+), V1.2(−), V1.3(+), V1.4(−), V2.1(+), V2.2(−), V2.3(+) and V2.4(−).

In various embodiments specifically contemplated for this aspect of the invention, the vectors in the vector set are components in a cloning system, or comprise part of a cloning system useful for making a gene and/or multigene construct as described for any other aspect of the invention.

In various embodiments specifically contemplated for this aspect of the invention, a gene construct and/or multigene construct is/are as described herein for any other aspect of the invention. Additionally, in various embodiments specifically contemplated for this aspect of the invention, a gene construct and/or multi gene construct is/are made, and a TU is, or multiple TUs are, added into the destination vector as described herein for any other aspect of the invention.

In one embodiment the method consists essentially of combining four V1 shuttle vectors or first shuttle vectors as described herein, four V2 shuttle vectors or second shuttle vectors as described herein, and at least one destination vector as described herein.

In one embodiment the method consists essentially of combining four V1 shuttle vectors or first shuttle vectors as described herein, four V2 shuttle vectors or second shuttle vectors as described herein, at least one destination vector as described herein, and at least one source vector as described herein.

In one embodiment the vector set is comprised in a kit.

In another aspect the invention relates to a method of making a multigene construct comprising at least two transcription units (TU), the method comprising:
(c) cloning a first cloning cassette comprising a first transcription unit (TU1), and four restriction sites A1, A2, C1 and C2 arranged in the following order:
5'-A1-TU1-C1-C2-A2-3', or
5'-A1-C1-C2-TU1-A2-3',
into a destination vector (V3) comprising a pair of restriction sites A1 and A2 flanking a second marker (M2) to make:
destination vector V3.1 comprising 5'-TU1-C1-C2-3' or
destination vector V3.2 comprising 5'-C1-C2-TU1-3',
(d) cloning a second cloning cassette comprising a second transcription unit (TU2), the second marker (M2), and four restriction sites A1, A2, C1 and C2 arranged in the following order:
5'-C1-TU2-A1-M2-A2-C2-3', or
5'-C1-A1-M2-A2-TU2-C2-3',
into V3.1 to make destination vector V4.1 comprising 5'-TU1-TU2-A1-M2-A2-3', or destination vector V4.2 comprising 5'-TU1-A1-M2-A2-TU2-3', or
into V3.2 to make destination vector V4.3 comprising 5'-TU2-A1-M2-A2-TU1-3', or destination vector V4.4 comprising 5'-A1-M2-A2-TU2-TU1-3'
wherein A1 and C1 are different restriction sites, and wherein A1=A2 and C1=C2.

In one embodiment V3.1 consists essentially of 5'-TU1-C1-C2-3'.

In one embodiment V3.2 consists essentially of 5'-C1-C2-TU1-3',

In one embodiment V4.1 consists essentially of 5'-TU1-TU2-A1-M2-A2-3'.

In one embodiment V4.2 consists essentially of 5'-TU1-A1-M2-A2-TU2-3'.

In one embodiment V4.3 consists essentially of 5'-TU2-A1-M2-A2-TU1-3'.

In one embodiment V4.4 consists essentially of 5'-A1-M2-A2-TU2-TU1-3'.

In one embodiment, A1 and A2 are removed from the first cloning cassette and the destination vector (V3) when the cloning cassette is cloned into V3 to make V3.1 or V3.2.

In one embodiment, C1 and C2 are removed from the second cloning cassette and the destination vector (V3.1 or V3.2) when the second cloning cassette is cloned into V3.1 or V3.2 to make V4.1 or V4.2, or V4.3 or V4.4, respectively.

In one embodiment, the method comprises:
(e) cloning a third cloning cassette comprising a third transcription unit (TU3) and four restriction sites A1, A2, C1 and C2 arranged in the following order:
5'-A1-TU3-C1-C2-A2-3', or
5'-A1-C1-C2-TU3-A2-3',
into V4.1 to make destination vector V5.1 comprising 5'-TU1-TU2-TU3-C1-C2-3', or destination vector V5.2 comprising 5'-TU1-TU2-C1-C2-TU3-3', or
into V4.2 to make destination vector V5.3 comprising 5'-TU1-TU3-C1-C2-TU2-3', or destination vector V5.4 comprising 5'-TU1-C1-C2-TU3-TU2-3', or
into V4.3 to make destination vector V5.5 comprising 5'-TU2-TU3-C1-C2-TU1-3', or destination vector V5.6 comprising 5'-TU2-C1-C2-TU3-TU1-3', or
into V4.4 to make destination vector V5.7 comprising 5'-TU3-C1-C2-TU2-TU1-3', or destination vector V5.8 comprising 5'-C1-C2-TU3-TU2-TU1-3',
wherein A1 and C1 are different restriction sites, and wherein A1=A2 and C1=C2.

In one embodiment, A1 and A2 are removed from the third cloning cassette and the destination vector when the cloning cassette is cloned into V4.1, V4.2, V4.3 or V4.4.

In one embodiment, the method comprises cloning a fourth cloning cassette comprising a fourth transcription unit (TU4) and four restriction sites A1, A2, C1 and C2 arranged in the following order:

5'-C1-TU4-A1-M2-A2-C2-3', or
5'-C1-A1-M2-A2-TU4-C2-3',
  into V5.1 to make destination vector V6.1 comprising 5'-TU1-TU2-TU3-TU4-A1-M2-A2-3', or destination vector V6.2 comprising 5'-TU1-TU2-TU3-A1-M2-A2-TU4-3', or
  into V5.2 to make destination vector V6.3 comprising 5'-TU1-TU2-TU4-A1-M2-A2-TU3-3', or destination vector V6.4 comprising 5'-TU1-TU2-A1-M2-A2-TU4-TU3-3', or
  into V5.3 to make destination vector V6.5 comprising 5'-TU1-TU3-TU4-A1-M2-A2-TU2-3', or destination vector V6.6 comprising 5'-TU1-TU3-A1-M2-A2-TU4-TU2-3', or
  into 5.4 to make destination vector V6.7 comprising 5'-TU1-TU4-A1-M2-A2-TU3-TU2-3', or destination vector V6.8 comprising 5'-TU1-A1-M2-A2-TU4-TU3-TU2-3', or
  into V5.5 to make destination vector V6.9 comprising 5'-TU2-TU3-TU4-A1-M2-A2-TU1-3', or destination vector V6.10 comprising 5'-TU2-TU3-A1-M2-A2-TU4-TU1-3', or
  into V5.6 to make destination vector V6.11 comprising 5'-TU2-TU4-A1-M2-A2-TU3-TU1-3', or destination vector V6.12 comprising 5'-TU2-A1-M2-A2-TU4-TU3-TU1-3', or
  into V5.7 to make destination vector V6.13 comprising 5'-TU3-TU4-A1-M2-A2-TU2-TU1-3', or destination vector V6.14 comprising 5'-TU3-A1-M2-A2-TU4-TU2-TU1-3', or
  into V5.8 to make destination vector V6.15 comprising 5'-TU4-A1-M2-A2-TU3-TU2-TU1-3', or destination vector V6.16 comprising 5'-A1-M2-A2-TU4-TU3-TU2-TU1-3',
  wherein A1 and C1 are different restriction sites, and wherein A1=A2 and C1=C2.

In one embodiment, C1 and C2 are removed from the fourth cloning cassette and the destination vector when the fourth cloning cassette is cloned into V5.1, V5.2, V5.3, V5.4, V5.5, V5.6, V5.7 or V5.8.

In further embodiments the method comprises adding additional cassettes to various destination vectors as described above for V1.1-V6.15 by cloning an $n^{th}$ cloning cassette comprising an $n^{th}$ TU (TUn) and four restriction sites A1, A2, C1 and C2 arranged either:
  (i) in a V1 vector as either:
  5'-A1-TUn-C1-C2-A2-3', or
  5'-A1-C1-C2-TUn-A2-3',
  into a destination vector that harbours an even number of TUs and a pair of restriction sites A1 and A2 flanking a second marker (M2), to make a destination vector harbouring an odd number of TUs. In one embodiment, A1 and A2 in (i) are removed from the $n^{th}$ cloning cassette and from the destination vector when the $n^{th}$ cloning cassette is cloned into the destination vector using A1 and A2 to make a new destination vector containing the $n^{th}$ TU.
  or
  (ii) in a V2 vector as either:
  5'-C1-TUn-A1-M2-A2-C2-3', or
  5'-C1-A1-M2-A2-TUn-C2-3',
  into a destination vector that harbours an odd number of TUs and a pair of restriction sites C1 and C2, to make a destination vector harbouring an even number of TUs. In one embodiment, C1 and C2 in (ii) are removed from the $n^{th}$ cloning cassette and from the destination vector when the $n^{th}$ cloning cassette is cloned into the destination vector using C1 and C2 to make a new destination vector containing the $n^{th}$ TU.

In one embodiment A1, A2, C1 and C2 are Type IIS restriction sites. In one embodiment the Type IIS restriction sites are selected from the group consisting of BsaI, AarI and BsmBI sites. In one embodiment A1 and A2 are AarI restriction sites. In one embodiment C1 and C2 are BsmBI restriction sites.

In one embodiment the destination vector is a vector selected from the group consisting of plasmids, bacteriophage, phagemids, cosmids, fosmids, bacterial artificial chromosomes, yeast artificial chromosomes, and phage artificial chromosomes or a combination thereof. In one embodiment the destination vector is a plasmid.

In one embodiment M2 encodes a selectable marker or a scorable marker. In one embodiment M2 is a scorable marker. In one embodiment the scorable is a chromogenic marker, preferably a lacZ marker.

In one embodiment M2 is a selectable marker. In one embodiment the selectable marker is a polynucleotide encoding for antibiotic resistance. In one embodiment the antibiotic resistance is resistance to an antibiotic selected from the group consisting of kanamycin, chloramphenicol, tetracycline, streptomycin, spectinomycin, ampicillin, carbenicillin, nalidixic acid, amphotericin B, erythromycin, gentamycin, neomycin, and nystatin.

In one embodiment M1 is a selectable marker. In one embodiment the selectable marker is a gene that encodes a peptide that confers lethality on a cell or organism containing the marker, for example when the gene encoding the peptide is transformed into an appropriate cell, or when the cell or organism is grown under the appropriate conditions. In one embodiment the marker is selected from a group consisting of ccdB, pheS, rpsL, sacB. In one embodiment the marker is a mutant *E. coli* pheS selectable marker operably linked to a promoter, preferably an *E. coli* promoter, preferably the *E. coli* chloramphenicol acetyltransferase promoter. In one embodiment the mutant *E. coli* pheS selectable marker is a $Thr^{251}Ala/Ala^{294}Gly$ double mutant.

In one embodiment the multigene construct comprises, consists essentially or consists of at least one, preferably two, preferably three, preferably four, preferably five, preferably six, preferably seven, preferably eight, preferably nine, preferably at least ten TU's from a biosynthetic pathway.

In one embodiment the multigene construct comprises, consists essentially or consists of a complete biosynthetic pathway.

In one embodiment the biosynthetic pathway is a microbial, preferably fungal biosynthetic pathway.

In one embodiment the biosynthetic pathway is an indole diterpene biosynthetic pathway.

In one embodiment the indole diterpene biosynthetic pathway is a penitremane pathway, preferably a penitrem A pathway. In one embodiment the pathway is from a fungus, preferably *Penicilium* spp., preferably *P. crustosum*.

In one embodiment the indole diterpene biosynthetic pathway is a janthitremane pathway, preferably a janthitrem B pathway. In one embodiment the pathway is from a fungus, preferably *Penicilium* spp., preferably *P. janthinellum*.

In one embodiment the indole diterpene biosynthetic pathway is a lolitremane pathway, preferably the lolitrem B biosynthetic pathway, preferably from a fungus, preferably *Epichloë* spp., preferably *E. festucae*.

In one embodiment the indole diterpene biosynthetic pathway comprises, consists essentially of, or consists of at least one, preferably two, preferably three, preferably four genes required for the production of paspaline. In one embodiment the genes required for the production of paspaline comprise at least one of paxG, paxM, paxB and paxC, preferably at least two, preferably at least three, preferably all four of paxG, paxM, paxB and paxC. Preferably the genes required for the production of paspaline are from *Penicillium* spp, preferably *P. paxilli*.

In one embodiment the indole diterpene biosynthetic pathway comprises, consists essentially of, or consists of at least one, preferably two, preferably three, preferably four, preferably five, preferably six genes required for the production of paxilline. In one embodiment the genes required for the production of paxilline comprise at least one of paxG, paxM, paxB, paxC, paxQ and paxP, preferably at least two, preferably at least three, preferably at least four, preferably at least five, preferably all six of paxG, paxM, paxB, paxC, paxQ and paxP. Preferably the genes required for the production of paxiline are from *Penicillium* spp, preferably *P. paxilli*.

In one embodiment the biosynthetic is a naturally occurring biosynthetic pathway. In one embodiment the biosynthetic pathway is an artificial biosynthetic pathway.

In another aspect, the invention relates to a set of vectors comprising:
(i) four first shuttle vectors or V1 shuttle vectors of the invention,
(ii) four second shuttle vectors or V2 vectors of the invention, and
(iii) at least one destination vector,
the at least one destination vector comprising a pair of restriction sites,
wherein the pair of restriction sites in (iii) have a divergent orientation relative to each other and are the same as a pair of restriction sites in each of the shuttle vectors in (i), and in each of the shuttle vectors in (ii)
wherein the restriction sites in (i) have a convergent orientation relative to each other, and
wherein the restriction sites in (ii) have a divergent orientation relative to each other.

In one embodiment the set of vectors consists essentially of (i) and (ii).

In one embodiment, restriction of the restriction sites in any one of the vectors in (i) generates nucleotide overhangs of at least one nucleotide, preferably at least two, preferably at least three, preferably at least four nucleotides.

In one embodiment, restriction of the restriction sites in the destination vector in (iii) generates nucleotide overhangs of at least one nucleotide, preferably at least two, preferably at least three, preferably at least four nucleotides.

In one embodiment the pair of restriction sites in (iii) are Type IIS restriction sites. In one embodiment the Type IIS restriction sites are selected from the group consisting of BsaI, AarI and BsmBI sites. In one embodiment A1 and A2 are AarI restriction sites. In one embodiment C1 and C2 are BsmBI restriction sites.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents; or such sources of information, in any jurisdiction, are prior art, or form part of the common general knowledge in the art.

The invention will now be illustrated in a non-limiting way by reference to the following examples.

EXAMPLES

Materials and Methods
Molecular Biology

Restriction endonucleases were purchased from New England Biolabs (NEB, Ipswich, Mass., USA), except AarI, which was purchased from Thermo Scientific (Thermo Fisher Scientific, Waltham, Mass., USA). T4 DNA Ligase, 10×T4 DNA Ligase buffer and 10 mM ATP were from NEB (Ipswich, Mass., USA).

Primers and gBlocks were synthesised by Integrated DNA Technologies (IDT, Coralville, Iowa, USA). Other synthetic polynucleotides were synthesised by Epoch Life Science, Inc (Missouri City, Tex., USA).

Kits for purification of plasmid DNA and PCR products using spin-column protocols were purchased from Macherey-Nagel (Düren, Germany). Genomic DNA from *Penicillium paxilli* was isolated using the ZR Fungal/Bacterial DNA MicroPrep™ Kit from Zymo Research (Irvine, Calif., USA).

All PCRs for the construction of the MIDAS source, shuttle and destination vectors and for amplification of MIDAS modules were performed using Phusion High-Fidelity PCR Master Mix with HF Buffer (NEB, Ipswich, Mass., USA).

Isopropyl β-D-1-thiogalactopyranoside (IPTG) was purchased from Calbiochem (San Diego, Calif., USA), 5-bromo-4-chloro-3-indolyl-β-D-galactopyranoside (X-Gal) from PanReac AppliChem (Darmstadt, Germany), and 4-chloro-DL-phenylalanine (4CP) from Sigma (St Louis, Mo., USA).

Antibiotics used in this work were; Geneticin® (G418, from Sigma), kanamycin (PanReac AppliChem, Darmstadt, Germany) and spectinomycin (Gold Biotechnology, Olivette, Mo., USA).

Bacterial and Fungal Strains

Routine growth of *Escherichia coli* was performed at 37° C. in LB broth. Chemically competent *E. coli* XL10-Gold Ultracompetent cells (Agilent Technologies, Santa Clara, Calif., USA) were used for transformation and maintenance of plasmids assembled at Level-3. Chemically competent *E. coli* HST08 Stellar cells (Clontech Laboratories, Inc., Mountain View, Calif., USA) were used for routine transformations and maintenance of all other plasmids (including all source, shuttle and destination vectors, and all plasmids assembled at Level-1 and Level-2). *Penicillium paxilli* strains used in this study are shown in Table 15.

Construction of MIDAS Vectors

As with the MIDAS modules, all MIDAS source, shuttle and destination vectors were required to be domesticated (i.e. made free of recognition sites for AarI, BsaI and BsmBI). To achieve this, the initial plasmids in the construction of the MIDAS vectors were assembled in a modular fashion by BsaI-mediated assembly of PCR fragments corresponding to specific, functional plasmid structures (e.g., origin of replication, resistance markers, etc.); with the number of PCR fragments depending both on the number of internal Type IIS sites to be removed, and on the number of plasmid structures to be maintained as independent, functional pieces. MIDAS precursor plasmids were constructed in a modular fashion by BsaI-mediated Golden Gate assembly of PCR-generated DNA fragments containing terminal, convergent BsaI recognition sites (see Tables 1, 2 and 3). Typically, 1-2 μL of each purified PCR fragment, 1 μL of BsaI (20 U/μL), 1 μL of T4 DNA Ligase (400 U/μL) and 2 μL of 10×T4 DNA Ligase buffer in a total reaction volume of 20 μL were incubated overnight at 37° C.

Construction of Level-1 Source Vector (pML1)

The pML1 precursor plasmid was generated using a four-way BsaI-mediated Golden Gate reaction between PCR fragments CV-161, CV-162, CV-74 and CV-152 (Table 1). Following Golden Gate assembly, an aliquot of each reaction was transformed into *E. coli* HST08 Stellar competent cells (Clontech Laboratories, Inc., Mountain View, Calif., USA) by heat shock and spread onto LB plates supplemented with 50 μg/mL spectinomycin, 1 mM IPTG and 50 μg/mL X-Gal. Blue colonies were screened by restriction enzyme digestion of purified plasmid DNA, and confirmed by sequencing.

The 329 bp NcoI-XhoI fragment in the pML1 precursor was replaced, by restriction enzyme digestion and ligation, with the 346 bp NcoI-XhoI fragment of PCR CV-81, which contains a lacZα-based Golden Gate cloning cassette ([CTCG]BsmBI-lacZα-BsmBI[AGAC]). The resultant plasmid is the Level-1 source vector pML1.

Construction of Level-2 Shuttle Vectors (pML2 Vectors)

A precursor of the pML2 shuttle vectors was generated using a four-way BsaI-mediated Golden Gate reaction between PCR fragments CV-153, CV-154, CV-77 and CV-152 (Table 2). Following Golden Gate assembly, an aliquot of each reaction was transformed into *E. coli* HST08 Stellar competent (Clontech Laboratories, Inc., Mountain View, Calif., USA) cells by heat shock and spread onto LB plates supplemented with 75 μg/mL kanamycin, 1 mM IPTG and 50 μg/mL X-Gal. Blue colonies were screened by restriction enzyme digestion of purified plasmid DNA, and confirmed by sequencing.

The pML2 precursor was digested with NcoI+XhoI and ligated to gBlocks digested with the same enzymes. The eight gBlocks (Table 4) can be classified into two groups—one group comprising four "W" gBlocks (ML2(+)WF, ML2(+)WR, ML2(−)WF and ML2(−)WR) and a second group composed of four "B" gBlocks (ML2(+)BF, ML2(+)BR, ML2(−)BF or ML2(−)BR). Ligations were transformed into *E. coli* Stellar and spread onto LB plates supplemented with 75 μg/mL kanamycin, 1 mM IPTG and 50 μg/mL X-Gal. White colonies were analysed by restriction enzyme digestion of purified plasmid DNA, and confirmed by sequencing. The resultant eight plasmids were designated "gBlock precursor plasmids", comprising four "W" gBlock precursor plasmids and four "B" gBlock precursor plasmids.

A synthetic polynucleotide sequence encoding the Thr$^{251}$Ala/Ala$^{294}$Gly double mutant of the *E. coli* pheS, as described by Miyazaki (33), was supplied by Epoch Life Science, Inc (Missouri City, Tex., USA). The coding sequence of the pheS gene was amplified (PCR CV-141) and placed under the control of the chloramphenicol acetyltransferase (cat) promoter by BsaI-mediated Golden Gate assembly with PCR CV-129. The BsaI was heat-inactivated and the assembled pheS gene was then ligated into each of the eight gBlock precursor plasmids generated in the previous step that had also been treated with BsaI. Ligations were transformed by heat shock into *E. coli* HST08 Stellar competent cells (Clontech Laboratories, Inc., Mountain View, Calif., USA), spread onto LB plates supplemented with 75 μg/mL kanamycin, and colonies analysed by restriction enzyme analysis and sequencing. For the four "W" gBlock precursor plasmids, ligation of the assembled pheS gene resulted in the four "W" Level-2 shuttle vectors: pML2(+)WF, pML2(+)WR, pML2(−)WF and pML2(−)WR.

To produce the four "B" Level-2 shuttle vectors, the four "B" gBlock precursor plasmids harbouring the assembled pheS gene from the previous step, were digested with AarI and ligated to BsaI-digested PCR CV-78, resulting in the four "B" Level-2 shuttle vectors: pML2(+)BF, pML2(+)BR, pML2(−)BF and pML2(−)BR. Ligations were transformed into *E. coli* HST08 Stellar (Clontech Laboratories, Inc., Mountain View, Calif., USA), spread onto LB plates supplemented with 75 μg/mL kanamycin, 1 mM IPTG and 50 μg/mL X-Gal. Blue colonies were analysed by restriction analysis and sequencing.

Functionality of the mutant pheS gene in each of the eight pML2 shuttle vectors was confirmed by transforming 0.1 μg of each plasmid into *E. coli* HST08 Stellar competent cells and spreading transformation mixes onto LB plates supplemented with 1.25 mM 4CP and 75 μg/mL kanamycin, and onto LB plates supplemented with 75 μg/mL kanamycin only (no 4CP). In each case, no colonies were observed when 4CP-containing plates were spread with undiluted transformation mixes (giving a calculated efficiency of $<3.25 \times 10^4$ Kan$^R$ cfu/μg), while $>1.3 \times 10^6$ Kan$^R$ cfu/μg plasmid DNA was calculated for each vector following growth on plates devoid of 4CP, indicating high counter-selection efficiency.

Construction of Level-3 Destination Vector (pML3)

Plasmid pML3 was generated using a four-way BsaI-mediated Golden Gate reaction between PCR fragments CV-161, CV-162, CV-79 and CV-152 (Table 3). Following Golden Gate assembly, an aliquot of each reaction was transformed into *E. coli* HST08 Stellar competent cells (Clontech Laboratories, Inc., Mountain View, Calif., USA) by heat shock and spread onto LB plates supplemented with 50 μg/mL spectinomycin, 1 mM IPTG and 50 μg/mL X-Gal. Blue colonies were screened by restriction enzyme digestion of purified plasmid DNA, and confirmed by sequencing.

Protocols for MIDAS Level-1 Module Cloning

PCR-amplified modules were purified using spin-column protocols and cloned into the MIDAS Level-1 plasmid, pML1, by BsmBI-mediated Golden Gate assembly. Typically, 1-2 μL (approximately 50-200 ng) of pML1 plasmid DNA from a miniprep was mixed with 1-2 μL of each purified PCR fragment, 1 μL of BsmBI (10 U/μL), 1 μL of T4 DNA Ligase (400 U/μL) and 2 μL of 10×T4 DNA Ligase buffer in a total reaction volume of 20 μL. Reactions were incubated at 37° C. for 1 to 3 hours and an aliquot (typically 2-3 μL) was transformed into 30 μL of *E. coli* HST08 Stellar competent cells (Clontech Laboratories, Inc., Mountain View, Calif., USA) by heat shock. Following a recovery period (addition of 250 μL SOC medium and incubation at 37° C. for 1 hour), aliquots of the transformation mix were spread onto LB agar plates supplemented with 50 μg/mL spectinomycin, 1 mM IPTG and 50 μg/mL X-Gal. Plates were incubated overnight at 37° C., and white colonies were chosen for analysis.

Protocols for MIDAS Level-2 TU Assembly

Using the modules cloned at Level-1, full-length TUs were assembled into MIDAS Level-2 plasmids by BsaI-mediated Golden Gate assembly. Typically, 40 fmol of pML2 plasmid DNA was mixed with 40 fmol of plasmid DNA of each Level-1 entry clone, 1 μL of BsaI-HF (20 U/μL), 1 μL of T4 DNA Ligase (400 U/μL) and 2 μL of 10×T4 DNA Ligase buffer in a total reaction volume of 20 μL. Reactions were incubated in a DNA Engine PTC-200 Peltier Thermal Cycler (Bio-Rad, Hercules, Calif., USA) using the following parameters: 45 cycles of (2 minutes at 37° C. and 5 minutes at 16° C.), followed by 5 minutes at 50° C. and 10 minutes at 80° C. Reactions were transformed into

*E. coli* HST08 Stellar competent cells as described under Protocols for MIDAS Level-1 module cloning and spread onto LB agar plates containing 75 μg/mL kanamycin and 1.25 mM 4CP. Following overnight incubation at 37° C., colonies were picked for analysis.

Protocols for MIDAS Level-3 Multigene Assembly

Full-length TUs assembled at Level-2, were used to create multigene assemblies in the Level-3 destination vector by alternating Golden Gate assembly using either AarI (for TUs cloned into pML2 "W" vectors) or BsmBI (for TUs cloned into pML2 "B" vectors). Typically, 40 fmol of Level-3 destination vector plasmid DNA was mixed with 40 fmol of Level-2 entry clone plasmid DNA.

For BsmBI-mediated assemblies, 1 μL of BsmBI (10 U/μL), 1 μL of T4 DNA Ligase (400 U/μL) and 2 μL of 10×T4 DNA Ligase buffer, was added to the plasmid DNA in a final reaction volume of 20 μL.

As discussed in the main text, two different reaction conditions were tested for AarI-mediated assemblies; (i) conventional Golden Gate reactions performed in T4 DNA Ligase buffer and (ii) reactions performed in AarI restriction enzyme buffer supplemented with ATP. For AarI-mediated reactions performed in T4 DNA Ligase buffer, 1 μL of AarI (2 U/μL), 0.4 μL of 50× oligonucleotide (25 μM, supplied with the enzyme), 1 μL of T4 DNA Ligase (400 U/μL) and 2 μL of T4 DNA Ligase buffer was added to the plasmid DNA, in a final reaction volume of 20 μL.

For AarI-mediated reactions carried out in restriction enzyme buffer, 1 μL of AarI (2 U/μL), 0.4 μL of 50× oligonucleotide (25 μM, supplied with the enzyme), 2 μL of 10× Buffer AarI (supplied with the enzyme), 1 μL of T4 DNA Ligase (400 U/μL) and 2 μL of 10 mM ATP was added to the plasmid DNA, in a final reaction volume of 20 μL.

All Level-3 reactions (BsmBI- and AarI-mediated) were incubated in a DNA Engine PTC-200 Peltier Thermal Cycler (Bio-Rad) using the following parameters: 45 cycles of (2 minutes at 37° C. and 5 minutes at 16° C.), followed by 5 minutes at 37° C. and 10 minutes at 80° C. Reactions were transformed into *E. coli* XL10-Gold competent cells as described under Protocols for MIDAS Level-1 module cloning and spread onto LB agar plates supplemented with 50 μg/mL spectinomycin, 1 mM IPTG and 50 μg/mL X-Gal. Plates were incubated overnight at 37° C. For AarI-mediated assembly reactions, white colonies were chosen for analysis while, for BsmBI-mediated assembly reactions, blue colonies were screened.

Media and Reagents Used for Fungal Work.

CDYE (Czapex-Dox/Yeast extract) medium with trace elements was made with deionized water and contained 3.34% (w/v) Czapex-Dox (Oxoid Ltd., Hampshire, England), 0.5% (w/v) yeast extract (Oxoid Ltd., Hampshire, England), and 0.5% (v/v) trace element solution. For agar plates, Select agar (Invitrogen, California, USA) was added to 1.5% (w/v).

Trace element solution was made in deionized water and contained 0.004% (w/v) cobalt(II) chloride hexahydrate (Ajax Finechem, Auckland, New Zealand), 0.005% (w/v) copper(II) sulfate pentahydrate (Scharlau, Barcelona, Spain), 0.05% (w/v) iron(II) sulfate heptahydrate (Merck, Darmstadt, Germany), 0.014% (w/v) manganese(II) sulfate tetrahydrate, and 0.05% (w/v) zinc sulfate heptahydrate (Merck, Darmstadt, Germany). The solution was preserved with 1 drop of 12 M hydrochloric acid.

Regeneration (RG) medium was made with deionized water and contained 2% (w/v) malt extract (Oxoid Ltd., Hampshire, England), 2% (w/v) D(+)-glucose anhydrous (VWR International BVBA, Leuven, Belgium), 1% (w/v) mycological peptone (Oxoid Ltd., Hampshire, England), and 27.6% sucrose (ECP Ltd. Birkenhead, Auckland, New Zealand). Depending on whether the media was to be used for plates (1.5% RGA) or overlays (0.8% RGA), Select agar (Invitrogen, Carlsbad, Calif., USA) was added to 1.5% or 0.8% (w/v), respectively.

Fungal Protocols—Protoplast Preparation

The preparation of fungal protoplasts for transformation was according to Yelton et al (34) with modifications. Five 25 mL aliquots of CDYE medium with trace elements, in 100 mL Erlenmeyer flasks, were inoculated with $5 \times 10^6$ spores and incubated for 28 hours at 28° C. with shaking (200 rpm). The fermentation broth from all five flasks was filtered through a sterile nappy liner and the combined mycelia were rinsed three times with sterile water and once with OM buffer (10 mM $Na_2HPO_4$ and 1.2 M $MgSO_4.7H_2O$, brought to pH 5.8 with 100 mM $NaH_2PO_4.2H_2O$). Mycelia were weighed, resuspended in 10 mL of filter-sterilized Lysing Enzymes solution (prepared by resuspending Lysing Enzymes from *Trichoderma harzianum* (Sigma, St Louis, Mo., USA) at 10 mg/mL in OM buffer) per gram of mycelia, and incubated for 16 hours at 30° C. with shaking at 80 rpm. Protoplasts were filtered through a sterile nappy liner into a 250 mL Erlenmeyer flask. Aliquots (5 mL) of filtered protoplasts were transferred into sterile 15 mL centrifuge tubes and overlaid with 2 mL of ST buffer (0.6 M sorbitol and 0.1 M Tris-HCl at pH 8.0). Tubes were centrifuged at 2600×g for 15 minutes at 4° C. The white layer of protoplasts that formed between the OM and ST buffers in each tube was transferred (in 2 mL aliquots) into sterile 15 mL centrifuge tubes, gently washed by pipette resuspension in 5 mL of STC buffer (1 M sorbitol, 50 mM Tris-HCl at pH 8.0, and 50 mM $CaCl_2$)) and centrifuged at 2600×g for 5 minutes at 4° C. The supernatant was decanted off and pelleted protoplasts from multiple tubes were combined by resuspension in 5 mL aliquots of STC buffer. The STC buffer wash was repeated three times until protoplasts were pooled into a single 15 mL centrifuge tube. The final protoplast pellet was resuspended in 500 μL of STC buffer and protoplast concentration was estimated with a hemocytometer. The protoplast stock was diluted to give a final concentration of $1.25 \times 10^8$ protoplasts per mL of STC buffer. Aliquots of protoplasts (100 μL) were used immediately for fungal transformations and excess protoplasts were preserved in 8% PEG solution (80 μL of protoplasts were added to 20 μL of 40% (w/v) PEG 4000 in STC buffer) in 1.7 mL microcentrifuge tubes and stored at −80° C.

Fungal Protocols—Transformation of *P. paxilli*

Fungal transformations—modified from Vollmer and Yanosfsky (35) and Oliver et al (36)—were carried out in 1.7 mL micro-centrifuge tubes containing 100 μL ($1.25 \times 10^7$) protoplasts, either freshly prepared in STC buffer, or stored in 8% PEG solution (as described above). A solution containing 2 μL of spermidine (50 mM in $H_2O$), 5 μL heparin (5 mg/mL in STC buffer), and 5 μg of plasmid DNA (250 μg/mL) was added to the protoplasts and, following incubation on ice for 30 minutes, 900 μL of 40% PEG solution (40% (w/v) PEG 4000 in STC buffer) was added. The transformation mixture was incubated on ice for a further 15-20 minutes, transferred to 17.5 mL of 0.8% RGA medium (prewarmed to 50° C.) in sterile 50 mL tubes, mixed by inversion, and 3.5 mL aliquots were dispensed onto 1.5% RGA plates. Following overnight incubation at 25° C., 5 mL of 0.8% RGA (containing sufficient geneticin to achieve a final concentration of 150 μg per mL of solid media) was overlaid onto each plate. Plates were incubated for a further 4 days at 25° C. and spores were picked from individual colonies and streaked onto CDYE agar plates supplemented with 150 µg/mL geneticin. Streaked plates were incubated at 25° C. for a further 4 days. Spores from individual colonies were suspended in 50 µL of 0.01% (v/v) triton X-100 and 5×5 µL aliquots of the spore suspension was transferred onto new CDYE agar plates supplemented with 150 µg/mL geneticin. Sporulation plates were incubated at 25° C. for 4 days and spore stocks were prepared as follows. Colony plugs from the sporulation plates were suspended in 2 mL of 0.01% (v/v) triton X-100, and 800 µL of suspended spores were mixed with 200 µL of 50% (w/v) glycerol in a 1.7 mL micro-centrifuge tube. Spore stocks were used to inoculate 50 mL of CDYE media, flash frozen in liquid nitrogen and stored at −80° C.

Large Scale Indole Diterpene Purification for NMR Analysis

Fungal transformants that produced high levels of novel indole diterpenes were grown in ≥1 litre of CDYE medium with trace elements, as described under "Indole diterpene production and extraction". Mycelia were pooled into 1 litre Schott bottles containing stir bars. 2-butanone was added and indole diterpenes were extracted overnight with stirring (≥700 rpm). Extracts were filtered through Celite® 545 (3. T. Baker®, Thermo Fisher Scientific, Waltham, Mass., USA) and dry loaded onto silica with rotary evaporation for crude purification by silica column prior to a final purification by semi-preparative HPLC. A 1 mL aliquot of crude extract was injected onto a semi-preparative reversed phase Phenomenex 5 µm C18(2) 100 Å (250×15 mm) column attached to an UltiMate® 3000 Standard LC system (Dionex, Thermo Fisher Scientific, Waltham, Mass., USA) run at a flow rate of 8.00 mL/minute. Multistep gradient methods were optimized for the purification of different sets of indole diterpenes. The purity of each indole diterpene was assessed by LC-MS and the structure was identified by NMR.

NMR

NMR samples were prepared in deuterated chloroform. Compounds were analysed by standard one-dimensional proton and carbon-13 NMR, two-dimensional correlation spectroscopy (COSY), heteronuclear single quantum correlation (HSQC) spectroscopy, and heteronuclear multiple bond correlation (HMBC) spectroscopy.

Indole Diterpene Production and Extraction

Fungal transformants were grown in 50 mL of CDYE medium with trace elements for 7 days at 28° C. in shaker cultures (200 rpm), in 250 mL Erlenmeyer flasks capped with cotton wool. Mycelia were isolated from fermentation broths by filtration through nappy liners, transferred to 50 mL centrifuge tubes (Lab Serv®, Thermo Fisher Scientific, Waltham, Mass., USA) and IDTs were extracted by vigorously shaking the mycelia (≥200 rpm) in 2-butanone for ≥45 minutes.

Thin-Layer Chromatography

The 2-butanone supernatant (containing extracted IDTs) was used for thin-layer chromatography (TLC) analysis on solid phase silica gel 60 aluminium plates (Merck, Darmstadt, Germany). IDTs were chromatographed with 9:1 chloroform:acetonitrile or 9:1 dichloromethane:acetonitrile and visualized with Ehrlich's reagent (1% (w/v) p-dimethylaminobenzaldehyde in 24% (v/v) HCl and 50% ethanol).

Liquid Chromatography-Mass Spectrometry

Samples were prepared for liquid chromatography-mass spectrometry (LC-MS) from those transformants that tested positive by TLC. Accordingly, a 1 mL sample of the 2-butanone supernatant (containing extracted IDTs) was transferred to a 1.7 mL micro-centrifuge tube and the 2-butanone was evaporated overnight. Contents were resuspended in 100% acetonitrile and filtered through a 0.2 µm membrane into an LC-MS vial. LC-MS samples were chromatographed on a reverse phase Thermo Scientific Accucore 2.6 µm C18 (50×2.1 mm) column attached to an UltiMate® 3000 Standard LC system (Dionex, Thermo Fisher Scientific, Waltham, Mass., USA) run at a flow rate of 0.200 mL/minute and eluted with aqueous solutions of acetonitrile containing 0.01% formic acid using a multistep gradient method (Table 13). Mass spectra were captured through in-line analysis on a maXis™ II quadrupole-time-of-flight mass spectrometer (Bruker, Billerica, Mass., USA).

Results

Metabolic Pathway Engineering

Gene reconstitution experiments using *Penicillium paxilli* strain PN2250 (CY2), which has a deletion of the entire PAX locus, have shown that four genes (paxG, paxC, paxM and paxB) are required for the production of paspaline (37), a key intermediate in the *P. paxilli* biosynthetic pathway for paxilline and other cyclic IDTs, with two additional genes (paxP and paxQ) being required for the biosynthesis of paxilline (38). To demonstrate the utility of MIDAS in synthetic biology applications, we decided to test the system for its ability to restore the *P. paxilli* pathway for paspaline and paxilline biosynthesis in this PAX-deficient strain. Accordingly, we tested the ability of MIDAS to: (i) assemble each of these six pax gene TUs from basic modules, (ii) assemble multigene plasmids containing up to six pax TUs (with each TU having the same relative position and orientation as that found in the native PAX cluster), and (iii) in a series of complementation experiments, determine whether such plasmids could reconstitute paspaline and/or paxilline production in the PAX-deficient strain.

Level-1 Assemblies

Transcription unit modules (ProUTR, CDS and UTRterm) were amplified for each of the six pax genes using genomic DNA from *P. paxilli* strain PN2013 as template (Table 7). Since the aim was to produce multigene plasmids for transformation of *P. paxilli* strains, a suitable selectable marker (nptII—conferring resistance to Geneticin®) was chosen for this work. Accordingly, a CDS module for the nptII gene was amplified and, to drive expression of this gene, ProUTR and UTRterm modules from the *Aspergillus nidulans* trpC gene were also amplified (see Table 7).

Figure 6:
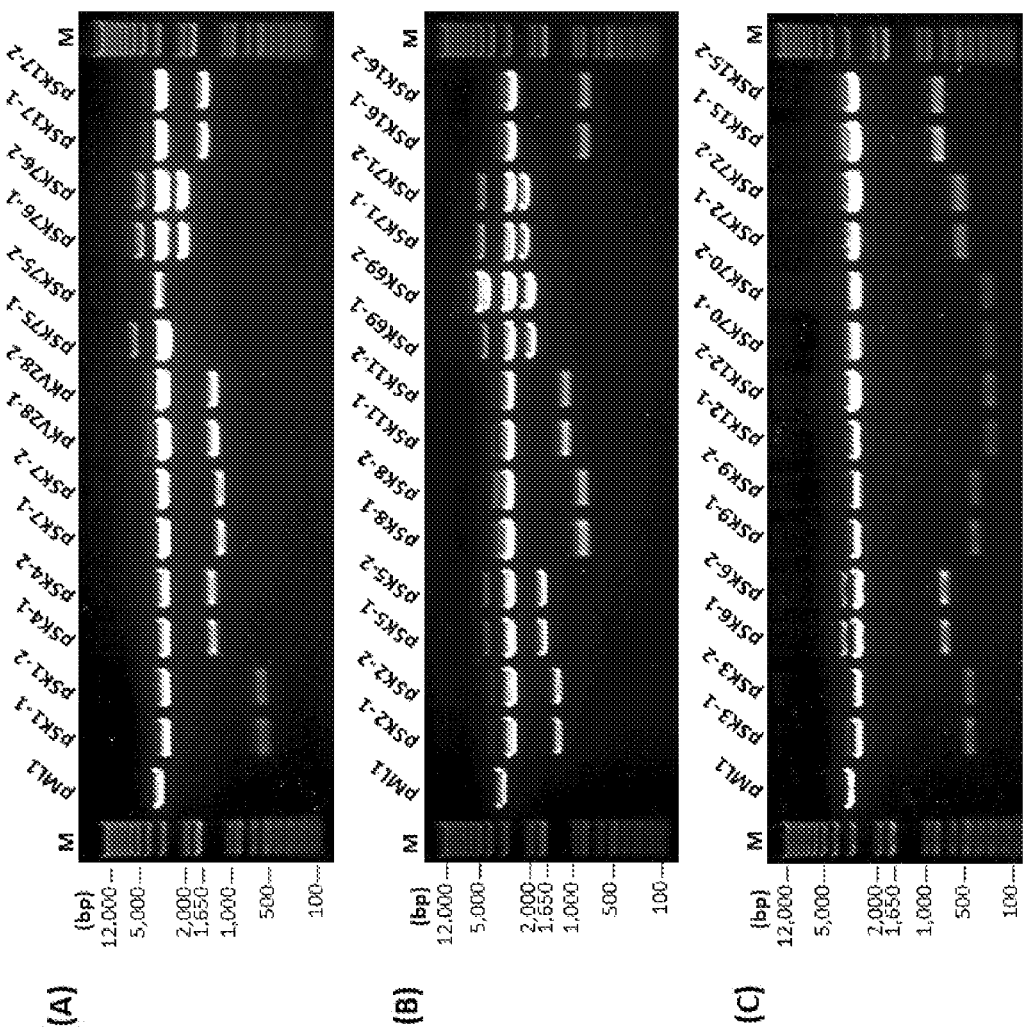
FIG. 6. Restriction digestion analysis of MIDAS Level-1 entry clones. Plasmid DNA prepared from 42 white Level-1 colonies (i.e., two colonies per module) was digested with BsaI and reactions were electrophoresed on 0.9% (w/v) agarose-TAE gels stained with SYBR® Safe (Thermo Fisher Scientific). The suffix (−1 or −2) after each plasmid name shown at the top of each gel indicates each of the two colonies analysed per construct. The module harboured by each plasmid is shown in parentheses. Expected sizes (bp) of fragments are listed. (A) Analysis of Level-1 ProUTR entry clones. pSK1 (paxG$_{ProUTR}$) 2720, 545; pSK4 (paxM$_{ProUTR}$) 2720, 1232; pSK7 (paxB$_{ProUTR}$) 2720, 1046; pKV28 (paxC$_{ProUTR}$) 2720, 1142; pSK75 (paxP$_{ProUTR}$): 2720, 2388; pSK76 (paxQ$_{ProUTR}$) 2720, 1760; pSK17 (trpC$_{ProUTR}$) 2720, 1289. (B) Analysis of Level-1 CDS entry clones. pSK2 (paxG$_{CDS}$): 2720, 1295; pSK5 (paxM$_{CDS}$): 2720, 1560; pSK8 (paxB$_{CDS}$): 2720, 820; pSK11 (paxC$_{CDS}$): 2720, 1078; pSK69 (paxP$_{CDS}$): 2720, 1850; pSK71 (paxQ$_{CDS}$): 2720, 2088; pSK16 (nptII$_{CDS}$): 2720, 797. (C) Analysis of Level-1 UTRterm entry clones. pSK3 (paxG$_{UTRterm}$): 2720, 511; pSK6 (paxM$_{UTRterm}$): 2250, 757; pSK9 (paxB$_{UTRterm}$): 2720, 425; pSK12 (paxC$_{UTRterm}$): 2720, 274; pSK70 (paxP$_{UTRterm}$): 2720, 273; pSK72 (paxQ$_{UTRterm}$): 2720, 502; pSK15 (trpC$_{UTRterm}$): 2720, 730. M: 1 kb Plus DNA ladder from Thermo Fisher Scientific. pML1 was also digested with BsaI: 3045. All cloned Level-1 modules showed the expected restriction digestion pattern.

The exon/intron structure of each of the pax genes was left unchanged and, where necessary, PCR primers were designed to amplify module fragments for domestication purposes (i.e., removal of internal recognition sites for AarI, BsaI and BsmBI). Domestication primers are listed in Table 7. The amplified full-length modules (and compatible sets of domesticated module fragments) were then cloned, by BsmBI-mediated Golden Gate assembly, into pML1. Reactions were transformed into *E. coli* HST08 Stellar cells and spread onto LB plates supplemented with spectinomycin, IPTG and X-Gal. Both the total numbers of colonies and the ratios of white:blue colonies showed a general inverse relationship to the number of PCR fragments required to be assembled together to form the functional module—with the number of PCR fragments in turn being dictated by domestication requirements (Table 8). Typically, modules assembled from only one PCR fragment (e.g., the paxG$_{ProUTR}$ module) produced higher numbers of cfus and higher ratios of white colonies (86-98%), whereas the numbers of cfus and proportion of white colonies (76-95%) trended lower for modules assembled from 2, 3, or 4 PCR fragments. Plasmid DNA from two white colonies from each assembly were analysed by restriction enzyme digestion using BsaI, which releases the cloned module. All forty-two Level-1 clones selected for restriction analysis contained an insert of the expected size (FIG. 6) and, of the subset of 28 clones that were sequenced, all BsmBI assembly junctions were correct, confirming the fidelity of the assembly reaction. The white:blue ratios and cloning efficiencies reported here for MIDAS Level-1 are in keeping with multi-fragment cloning efficiencies reported in the literature for other Golden Gate-based assembly techniques. The libraries of TUMs generated are shown in Table 9.

Level-2 Assemblies

Figure 7:
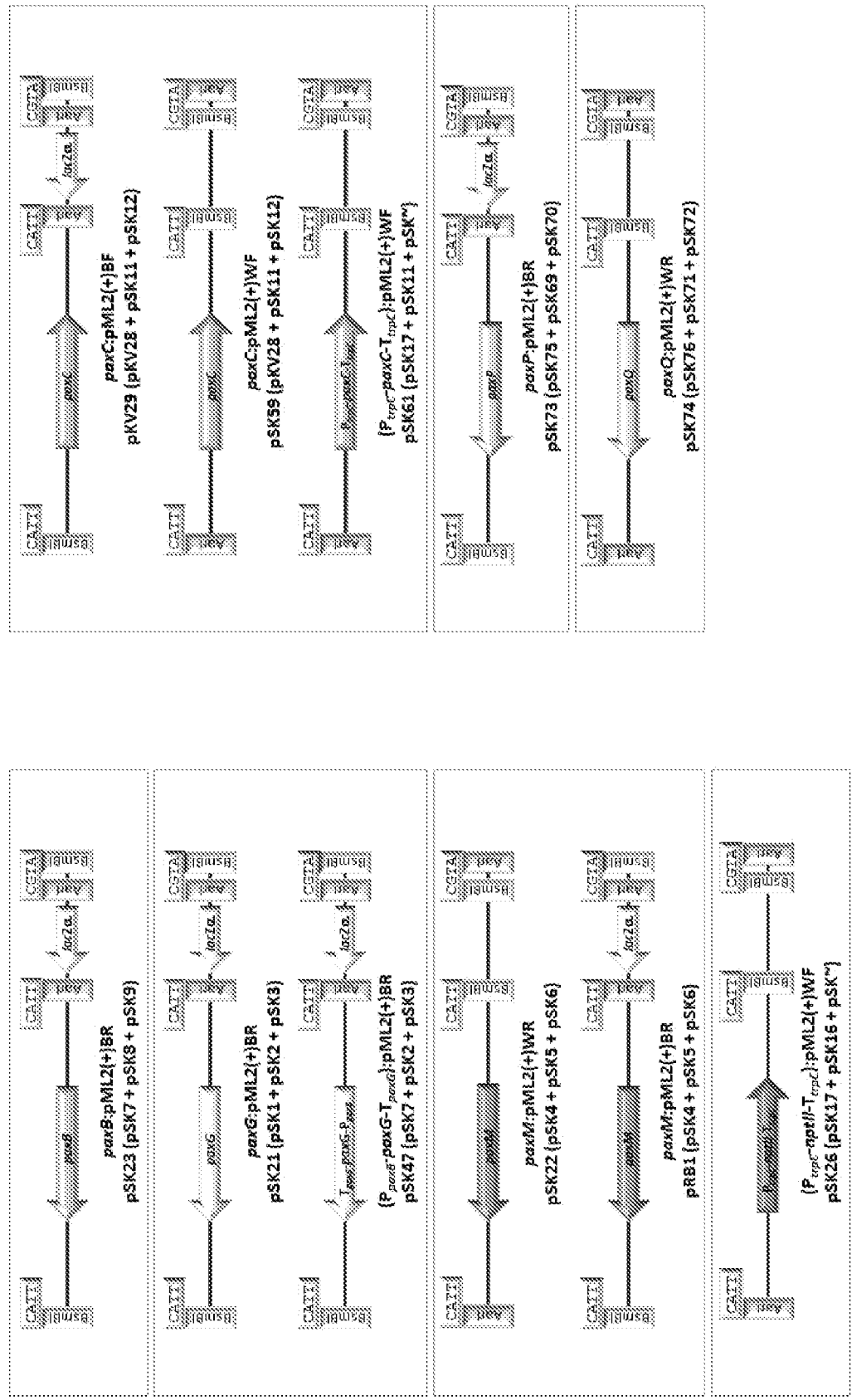
FIG. 7. MIDAS Level-2 transcription units (TUs) produced in this work. TUs are annotated using the name of the CDS they contain. TUs for paxB, paxP and paxQ were assembled from native promoter and terminator modules (giving rise to Level-2 entry clones pSK23, pSK73 and pSK74, respectively). Two paxM TUs were assembled using native promoter and terminator modules, albeit in different pML2 shuttle vectors—pSK22 was assembled using pML2(+)WR, while pRB1 was assembled using pML2(+)BR. Two paxG TU entry clones were assembled. The first (designated pSK21) was assembled from native promoter and terminator modules in pML2(+)BR. The second (pSK47) was also assembled using pML2(+)BR, but used the heterologous paxB$_{ProUTR}$ module and, for clarity, this TU is shown as P$_{paxB}$-paxG-T$_{paxG}$. Three paxC TUs were assembled. Two were assembled using native promoters and terminators; pKV29 was assembled using pML2(+)BF, pSK59 was assembled using pML2(+)WF. The third paxC TU was also assembled in pML2(+)WF but used the heterologous trpC$_{ProUTR}$ and trpC$_{UTRterm}$ modules. The resultant entry clone is designated pSK61 and, for clarity, the TU is shown as P$_{trpC}$-paxC-T$_{trpC}$. The nptII TU (conferring resistance to geneticin) was assembled in pML2(+)WF, producing plasmid pSK26 and the TU structure is shown as P$_{trpC}$-nptII-T$_{trpC}$.

At Level-2, TUs for paxG, paxC, paxM, paxB, paxP and paxQ were constructed by BsaI-assembling each pax CDS module with its homologous (i.e., native) ProUTR and UTRterm modules in pML2 shuttle vectors (see FIG. 7 and Table 10), and the assembled TUs are annotated with the name of the CDS they contain. For example, Level-2 entry clone pSK23, containing a paxB TU, was produced by assembling, in pML2(+)BR, the paxB$_{CDS}$ module (from plasmid pSK8) with the paxB promoter (i.e., the paxB$_{ProUTR}$ module in pSK7) and paxB terminator (paxB$_{UTRterm}$ module in pSK9). Likewise, a paxP TU (pSK73) was assembled in pML2(+)BR from paxP$_{ProUTR}$ (pSK75), paxP$_{CDS}$ (pSK69) and paxP$_{UTRterm}$ (pSK70) modules, while a paxQ TU (pSK74) was assembled in pML2(+)WR from paxQ$_{ProUTR}$ (pSK76), paxQ$_{CDS}$ (pSK71) and paxQ$_{UTRterm}$ (pSK72) modules.

Some TUs were assembled in more than one pML2 shuttle vector. For example, a paxM TU was assembled in both pML2(+)WR and pML2(+)BR. Both paxM Level-2 entry plasmids (pSK22 and pRB1) were assembled from the same Level-1 entry clones (pSK4, pSK5 and pSK6).

Two paxG TUs were assembled; in one case (plasmid pSK21) a paxG TU was produced by assembling, in pML2 (+)BR, the paxG$_{CDS}$ module (from plasmid pSK2) with its native promoter (i.e., the paxG$_{ProUTR}$ module in pSK1) and terminator (paxG$_{UTRterm}$, pSK3). To demonstrate the versatility of MIDAS for combinatorial assembly, a second paxG TU (plasmid pSK47) was also assembled in pML2(+)BR using the same paxG CDS (paxG$_{CDS}$, pSK2) and terminator (paxG$_{UTRterm}$, pSK3), but with expression driven by the heterologous paxB promoter (paxB$_{ProUTR}$, pSK7), and the TU structure in pSK47 is shown as P$_{paxB}$-paxG-T$_{paxG}$.

Three paxC TUs were assembled; in two cases (plasmids pSK59 and pKV29), the paxC TUs were assembled from the same Level-1 plasmids, by combining the paxC CDS (pSK11) with its native promoter (pKV28) and terminator (pSK12), albeit in different pML2 shuttle vectors—pML2 (+)WF in the case of pSK59, and pML2(+)BF in the case of pKV29. Once again, to demonstrate the versatility of MIDAS for combinatorial assembly, a third paxC TU (pSK61) was assembled in pML2(+)WF using the same paxC CDS, but using heterologous promoter (the trpC$_{ProUTR}$ in pSK17) and terminator (trpC$_{UTRterm}$, pSK15) modules. To distinguish this paxC TU from the other paxC TUs assembled from native promoters and terminators, the paxC TU structure in pSK61 is shown as P$_{trpC}$-paxC-T$_{trpC}$.

A nptII TU (conferring resistance to Geneticin®) was prepared by assembling the nptII$_{CDS}$ module (pSK16) with the trpC$_{ProUTR}$ (pSK17) and trpC$_{UTRterm}$ (pSK15) modules in pML2(+)WF, giving rise to the Level-2 entry clone pSK26 (and the TU structure is shown as P$_{trpC}$-nptII-T$_{trpC}$).

Figure 8:
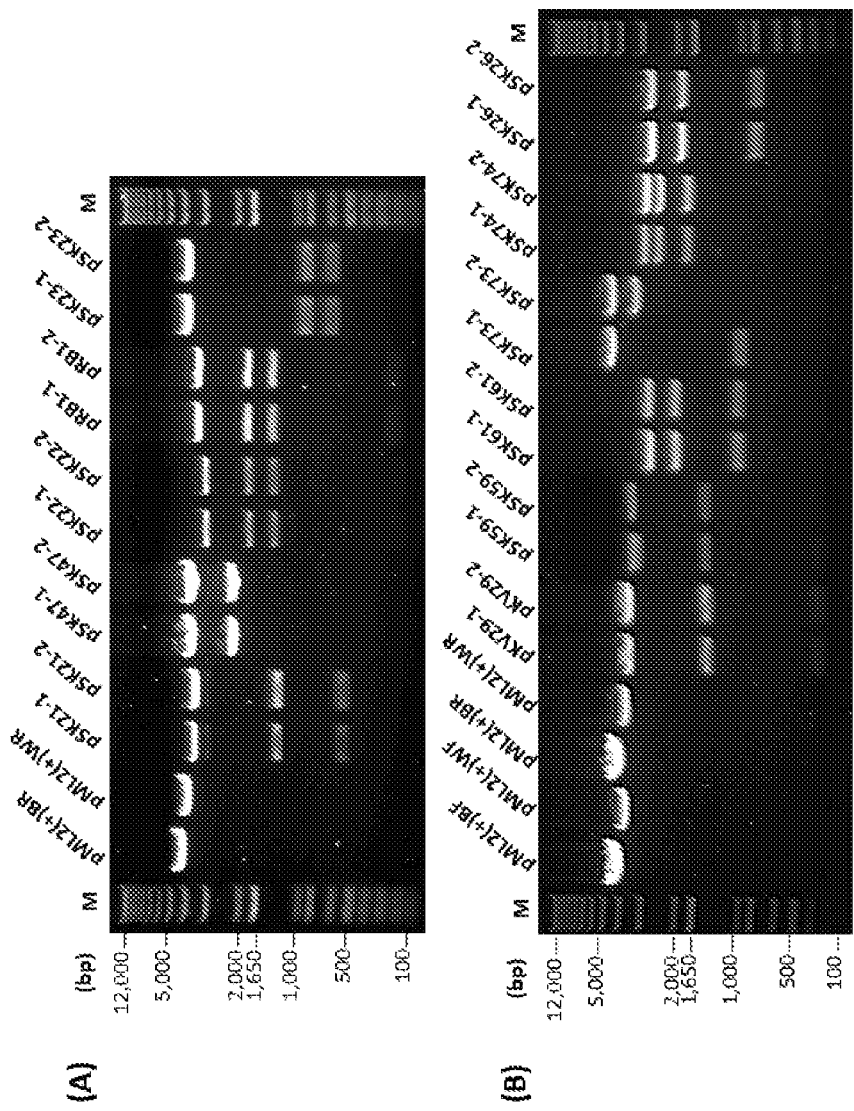
FIG. 8. Restriction digestion analysis of MIDAS Level-2 entry clones. Plasmid DNA prepared from 22 Level-2 colonies (two colonies per assembled plasmid) was treated with NcoI, unless otherwise stated, and reactions were electrophoresed on 0.9% (w/v) agarose-TAE gels stained with SYBR® Safe (Thermo Fisher Scientific). The suffix (−1 or −2) after each plasmid name shown at the top of each gel indicates each of the two colonies analysed per construct. The transcription unit harboured by each plasmid is shown in parentheses. Expected sizes (bp) of fragments are given. pSK21 (paxG TU) treated with NcoI+EcoRI: 3390, 1273, 591; pSK22 (paxM TU): 2884, 1739, 1314, 222; pSK23 (paxB TU): 3642, 901, 651; pSK59 (paxC TU): 3271, 1447, 386; pSK61 (P$_{trpC}$-paxC$_{CDS}$-T$_{trpC}$): 2716, 1980, 1011; pSK26 (P$_{trpC}$-nptII$_{CDS}$-T$_{trpC}$): 2716, 1871, 839; pRB1 (paxM TU): 3181, 1739, 1310, 222; pKV29 (paxC TU): 3568, 1447, 382; pSK47 (P$_{paxB}$-paxG$_{CDS}$-T$_{paxG}$): 3642, 2113; pSK73 (paxP TU) treated with NcoI+NheI: 4316, 3098; pSK74 (paxQ TU): 2827, 2402, 1731. M: 1 kb Plus DNA ladder from Thermo Fisher Scientific. Level-2 shuttle vectors were also digested with NcoI: pML2(+)WF: 3730; pML2(+)WR: 3730; pML2(+)BF: 4023; pML2(+)BR: 4023. All assembled TU clones, except pSK73-1, showed the expected restriction digest pattern (>95%).

After BsaI-mediated assembly, reactions were transformed into E. coli HST08 Stellar cells and spread onto LB plates supplemented with kanamycin and 4CP. For these 4-way assemblies (i.e. three entry clones and a pML2 shuttle vector), an average of approximately 6700 kanamycin resistant colonies was obtained per Golden Gate reaction (Table 10). Plasmid DNA from two colonies from each assembly reaction was analysed by restriction enzyme digestion and, of the 22 colonies analysed, 21 produced restriction digestion patterns consistent with the expected sizes (FIG. 8). To assess cloning fidelity, a subset of plasmids with the correct restriction enzyme digestion pattern were sequenced across the BsaI assembly junctions. The results showed that 100% (11/11) of the plasmids with the correct restriction pattern also had the correct assembly junctions, confirming the high fidelity of these BsaI-mediated multipart assemblies.

Level-3 Assemblies

Figure 9:
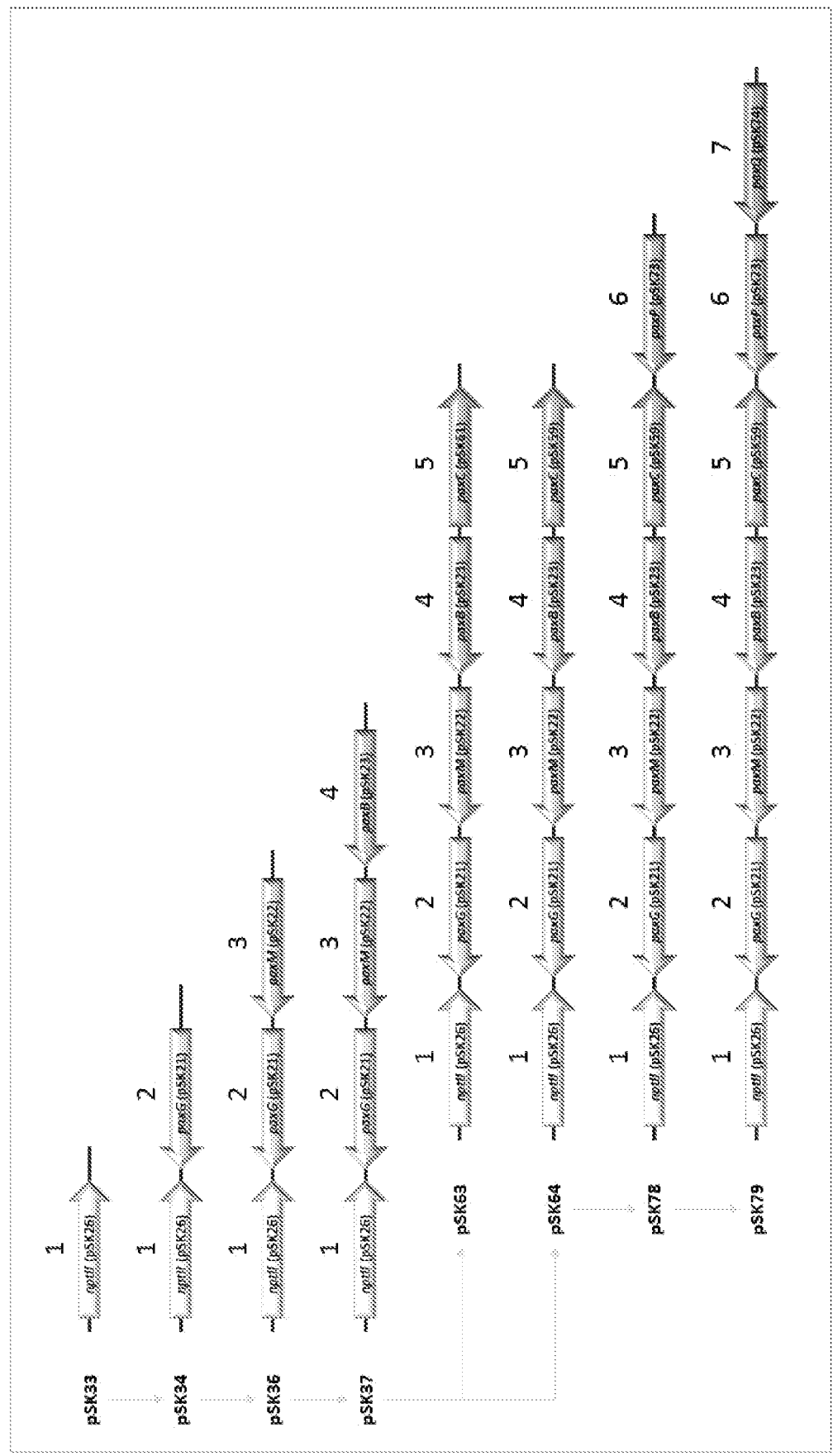
FIG. 9. MIDAS Level-3 multigene plasmids produced in this work for reconstructing the paxilline biosynthetic pathway in *P. paxilli* strain PN2250 (CY2). Plasmids were produced by sequentially loading the TUs for nptII, paxG, paxM, paxB, paxC, paxP and paxQ into the pML3 destination vector. The order in which each TU was loaded is shown by the numerals above each TU. Strain PN2250 (CY2) contains a deletion of the entire PAX cluster.

The TUs assembled at Level-2 were used to generate a variety of multigene plasmids at Level-3 (see FIG. 9 and Table 11). The first step in creating multigene plasmids suitable for transformation of P. paxilli strains was to clone in the fungal selectable marker gene. Therefore, following Level-2 assembly, the nptII TU (harboured by pML2 entry clone pSK26) was loaded into pML3 using an AarI-mediated Golden Gate reaction. The resultant plasmid (pSK33) then served as the destination vector for sequentially assembling multigene plasmids harbouring up to six pax genes.

The numbers of spectinomycin-resistant colonies obtained following transformation of each Level-3 Golden Gate reaction into E. coli XL10-Gold showed a general dependency on the size of the plasmid, with larger plasmids producing fewer colonies (Table 12).

Figure 10:
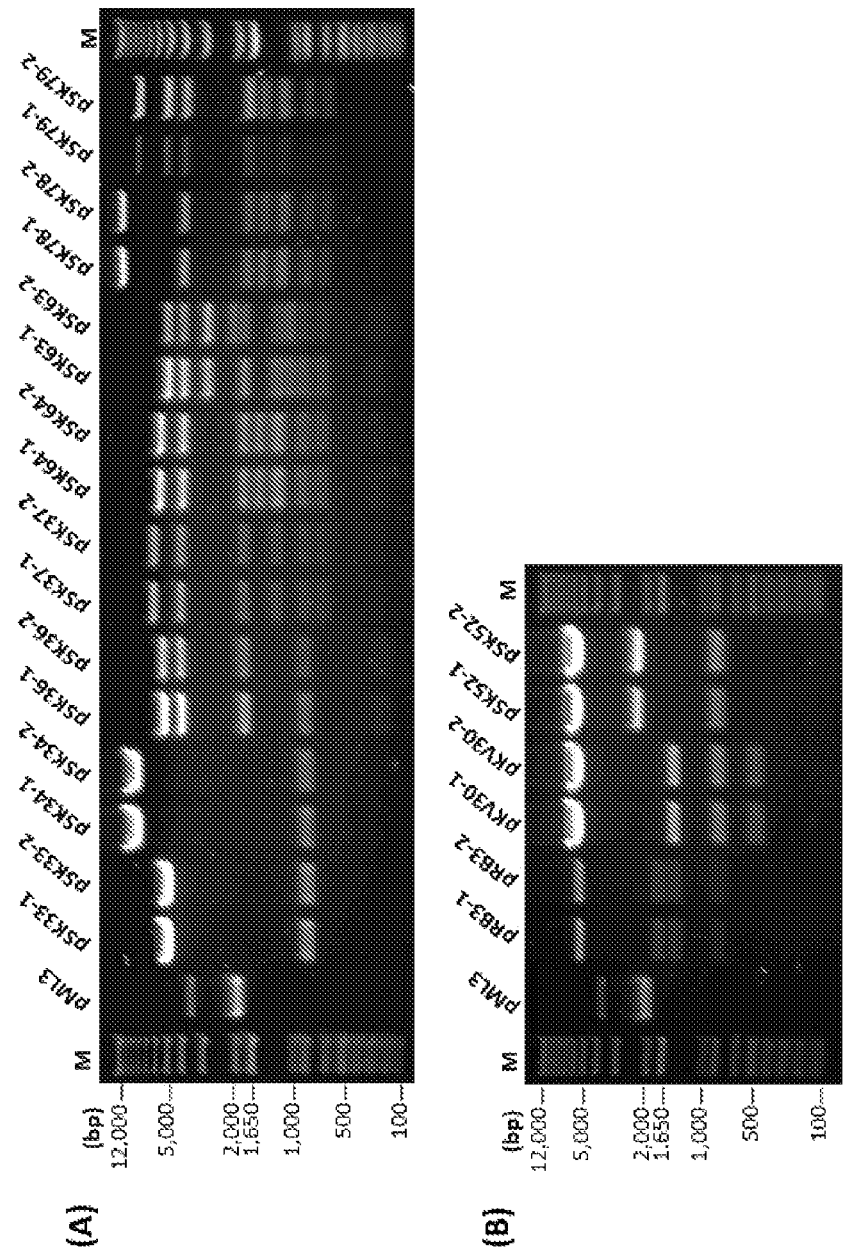
FIG. 10. Restriction digestion analysis of MIDAS Level-3 plasmids. Plasmid DNA prepared from 22 Level-3 colonies (two colonies per assembly reaction) was digested with NcoI and reactions were electrophoresed on 0.9% (w/v) agarose-TAE gels stained with SYBR® Safe (Thermo Fisher Scientific). The suffix (−1 or −2) after each plasmid name shown at the top of each gel indicates each of the two colonies analysed per construct. The transcription units harboured by each plasmid is shown in parentheses. Expected sizes (bp) of fragments are given. Uncut pML3: 3041; pSK33 (nptII): 4725, 839; pSK34 (nptII-paxG): 7385, 839; pSK36 (nptII-paxG-paxM): 4893, 3787, 1739, 839, 222; pSK37 (nptII-paxG-paxM-paxB): 5655, 3787, 1739, 1187, 839, 651, 222; pSK64 (nptII-paxG-paxM-paxB-paxC): 5280, 3787, 1739, 1447, 1187, 1129, 839, 651, 222; pSK63 (nptII-paxG-paxM-paxB-paxC): 4725, 3787, 2723, 1739, 1187, 1011, 839, 651, 222; pSK78 (nptII-paxG-paxM-paxB-paxC-paxP): 10100, 3787, 1739, 1447, 1187, 1129, 839, 651, 222; pSK79 (nptII-paxG-paxM-paxB-paxC-paxP-paxQ): 7590, 4836, 3787, 1739, 1731, 1447, 1187, 1129, 839, 651, 222; pRB3 (nptII-paxM): 5194, 1739, 1428, 839, 222; pKV30 (nptII-paxC): 5581, 1447, 839, 500; pSK52 (nptII-paxG): 5655, 2231, 839. M: 1 kb Plus DNA ladder from Thermo Fisher Scientific. All clones, except pSK63-2, showed the expected pattern of bands following restriction enzyme digestion (>95%).

BsmBI-mediated assemblies were very efficient, with >99% of the colonies obtained being of the desired (blue) colour (Table 12). Two blue colonies from each BsmBI-mediated reaction were selected for plasmid DNA purification and restriction analysis and, of the 12 plasmids analysed, all showed the expected restriction digestion pattern (FIG. 10).

For AarI-mediated assemblies, two different restriction-ligation conditions were tested. In the first set of experiments, AarI-mediated Golden Gate reactions were carried out, as usual, in T4 DNA Ligase buffer. The proportion of colonies of the desired colour (white) that were obtained was quite variable, ranging between 64-96% depending on the assembly reaction (Table 12). The high background of blue colonies suggested that AarI has reduced cleavage efficiency in the ligase buffer; indeed, many sites are not completely cleaved by AarI even under standard reaction conditions (39). Therefore, as an alternative approach, AarI assemblies were also performed in the reaction buffer supplied with the AarI restriction enzyme, additionally supplemented with ATP. Under these conditions, the assemblies showed a marked improvement in efficiency (>96% white colonies), and when two white colonies from each reaction were selected for plasmid DNA purification and restriction analysis, a high proportion (9/10) showed the expected restriction digestion pattern (FIG. 10).

Fungal Transformations and Analysis of IDT Phenotypes

Figure 14:
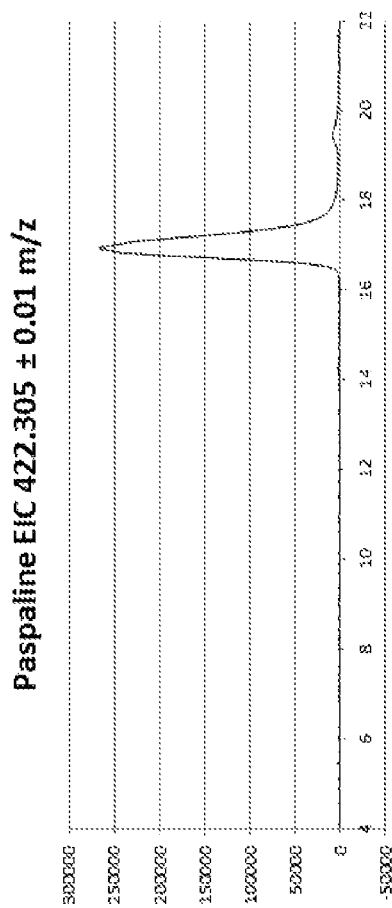
FIG. 14. Extracted ion chromatogram for paspaline standard (17.6 minutes, m/z 422.305±0.01) purified from wild type *P. paxilli* (strain PN2013).
Figure 15:
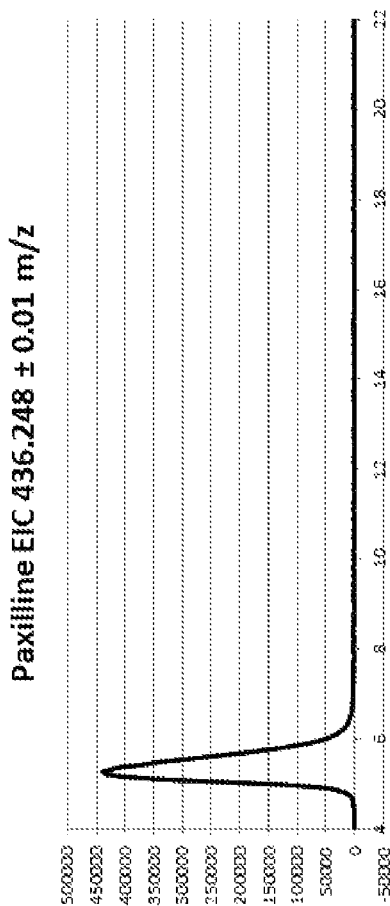
FIG. 15. Extracted ion chromatogram for paxilline standard (5.3 minutes, m/z 436.248±0.01) purified from wild type *P. paxilli* (strain PN2013).

In a series of complementation experiments, a selection of the Level-3 plasmids produced in this work were transformed into P. paxilli strains harbouring appropriate genetic backgrounds. Paspaline and/or paxilline phenotypes of geneticin resistant fungal transformants were determined by an initial thin-layer chromatography (TLC) screen of mycelial extracts and confirmed by LC-MS. For these purposes, paspaline and paxilline reference standards were prepared from extracts of wild type P. paxilli (strain PN2013) by semi-preparative HPLC. The HPLC peaks were analysed by high-resolution mass spectrometry, which identified [M+H]$^+$ masses of 422.3055 m/z at 17.6 minutes and 436.2485 m/z at 5.3 minutes, corresponding to the masses of paspaline (calc. [M+H]$^+$ 422.3054 m/z) and paxilline (calc. [M+H]$^+$ 436.2482 m/z), respectively (FIG. 14 and FIG. 15, respectively). NMR was used to confirm the structures of the purified reference standards (see Table 14 and FIGS. 22 to 31).

Restoration of Paspaline Production in a ΔPAX Deletion Mutant

Since genetic reconstitution experiments have shown that complementation using just four genes (paxG, paxM, paxB and paxC) can restore paspaline production in *P. paxilli* strain PN2250 (CY2), which has a deletion of the entire PAX locus (37), we decided to test whether MIDAS-assembled multigene plasmids harbouring these four core genes could also restore production of this IDT in this ΔPAX strain.

Accordingly, TUs for paxG (pSK21), paxM (pSK22) and paxB (pSK23), each under the control of their native promoters and terminators, were loaded sequentially into pSK33, followed by a paxC TU from either pSK59 (native promoter) or pSK61 (heterologous trpC promoter), to produce pSK64 and pSK63, respectively (see FIG. 9 and Table 11). Because pSK64 and pSK63 differ only in the final added TU, they were able to be constructed from the same precursor plasmid, pSK37.

Figure 11:
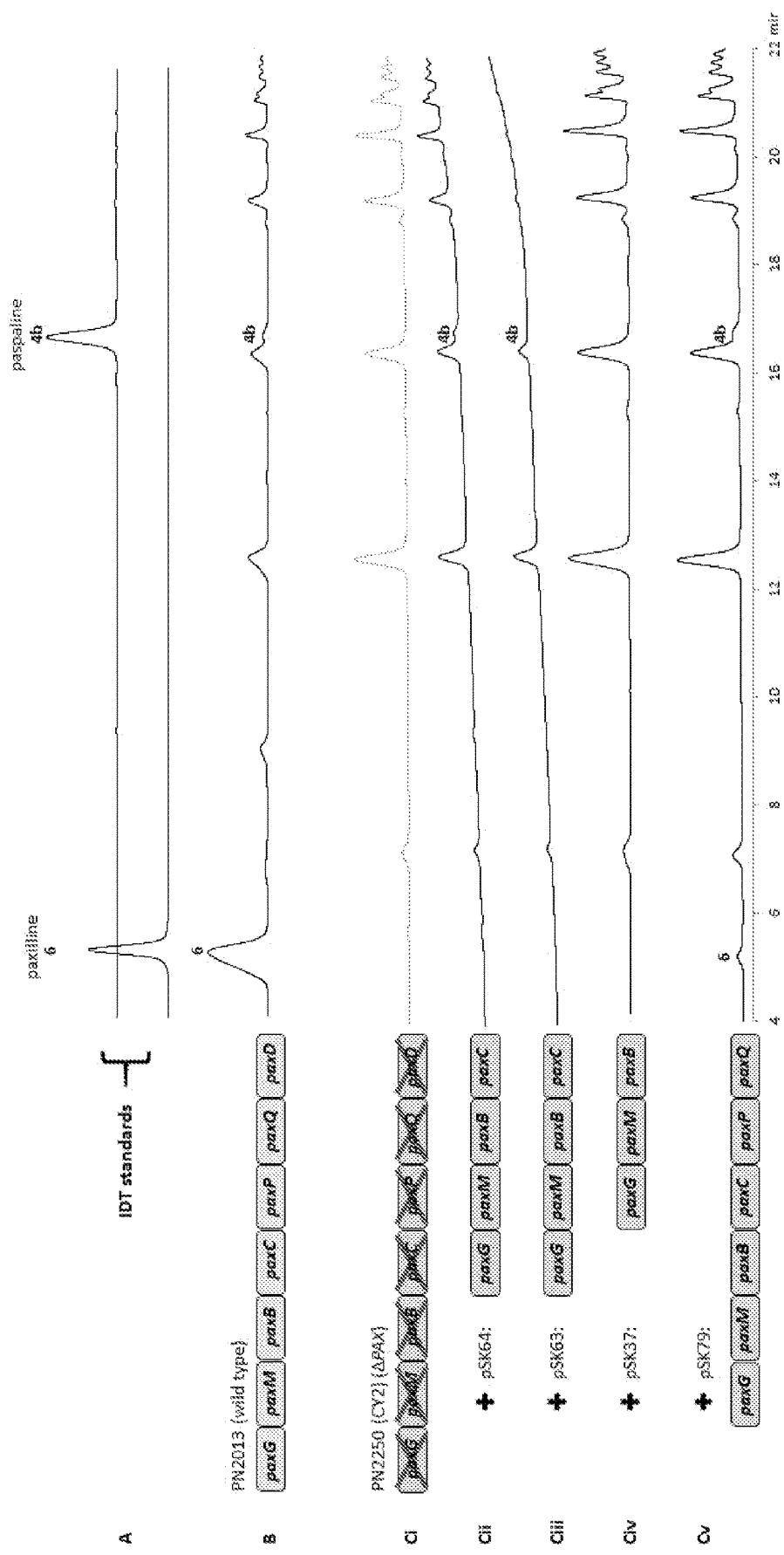
FIG. 11. HPLC analysis of *P. paxilli* transformants. HPLC analysis (271 nm) was used for identification of IDTs extracted from fungal mycelia. (A) Overlaid HPLC traces of paspaline and paxilline reference standards. (B) HPLC trace of wild type strain PN2013, showing the presence of paspaline and paxilline. An HPLC trace of the ΔPAX mutant PN2250 (CY2) is shown (Ci) and HPLC traces following transformation of this mutant with plasmids pSK64 (Cii), pSK63 (Ciii), pSK37 (Civ) or pSK79 (Cv). The coloured boxes to the left of the HPLC traces show the genotypes of each *P. paxilli* strain and the genotype of each transforming plasmid, with a cross (X) indicating the pax gene(s) that have been deleted from the genome of the KO strains. As expected paspaline and paxilline are absent from the parental ΔPAX KO strain PN2250 (CY2) as assessed by HPLC (trace Ci) and EIC (FIG. 17). For transformants pSK64:PN2250 and pSK63:PN2250 (traces Cii and Ciii, respectively), peaks corresponding to paspaline were identified, albeit at low levels. Their identity was confirmed by the corresponding 422.305±0.01 m/z EIC (FIG. 18A and FIG. 19A, respectively). Transformant pSK37:PN2250 served as a negative control and no peaks corresponding to paxilline or paspaline were identified by HPLC (trace Civ), nor in the EIC analysis (FIG. 20).
Figure 12:
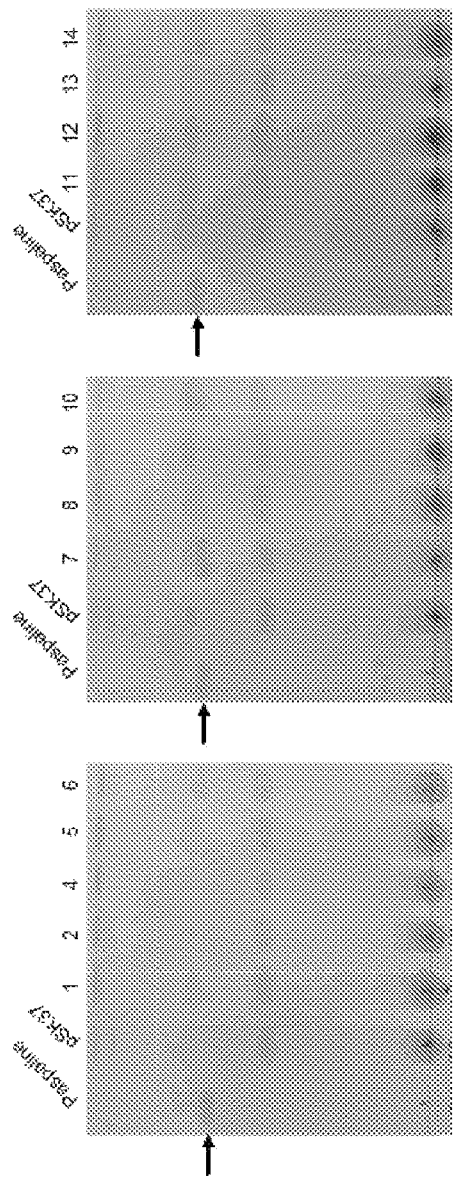
FIG. 12. Thin layer chromatography (TLC) analysis of mycelial extracts. In order to screen fungal transformants for production of IDTs, 2-butanone extracts of fungal mycelia were chromatographed, alongside a purified paspaline reference standard, on normal phase TLC plates and visualized with Ehrlich's reagent. The migratory position of the paspaline reference standard is indicated by the arrow. (A) Analysis of pSK64 transformants of *P. paxilli* PN2250 (CY2). Of the 13 fungal lines analysed following transformation of *P. paxilli* PN2250 (CY2) with plasmid pSK64, five (lines 6, 7, 8, 10 and 14) showed evidence for the presence of paspaline in their extracts. Fungi transformed with plasmid pSK37 acted as a negative control (lanes labelled "pSK37"). (B) Analysis of pSK63 transformants of *P. paxilli* PN2250 (CY2). Of the 5 fungal lines analysed following transformation of *P. paxilli* PN2250 (CY2) with plasmid pSK63, three (lines 5, 8 and 11) showed evidence for the presence of paspaline in their extracts. Fungi transformed with plasmid pSK37 acted as a negative control (lane labelled "pSK37"). (C) Analysis of pSK37 transformants of *P. paxilli* PN2250 (CY2). Given the low proportion (44%) of geneticin resistant transformants that produced paspaline in the TLC screens described in (A) and (B), a larger sample of pSK37 (negative control) transformants were screened. As expected, none of the 10 lines analysed showed evidence of paspaline in their extracts.
Figure 12:
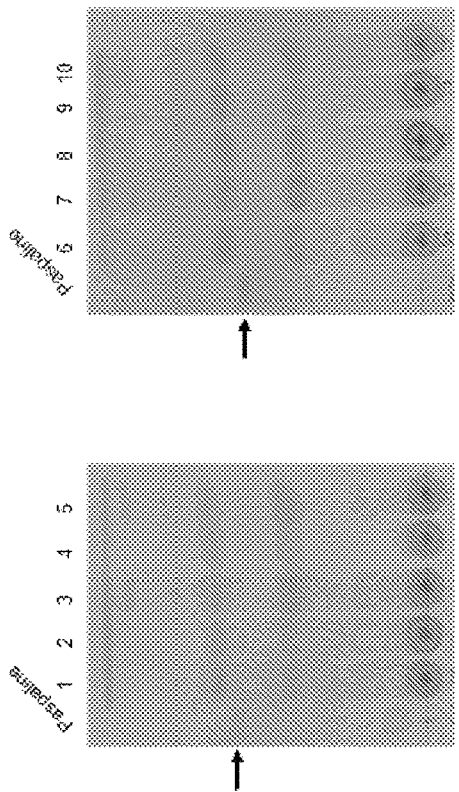
Figure 12:
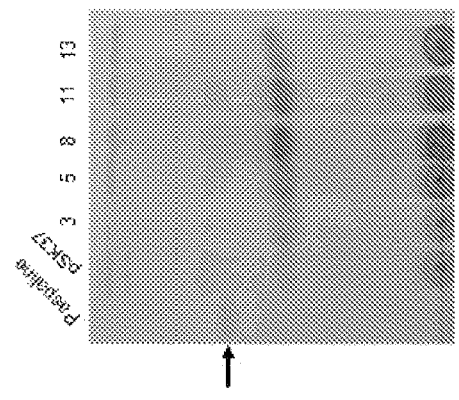

When plasmids pSK64 or pSK63 were transformed into *P. paxilli* strain PN2250 (CY2), 8/18 (approximately 44%) of the geneticin resistant colonies screened by thin layer chromatography (TLC) showed the presence of paspaline in their extracts (FIG. 12). LC-MS analysis of transformant pSK64:PN2250 #14 identified a peak with a retention time (see FIG. 11, trace Cii) and extracted-ion chromatogram (EIC) mass (FIG. 18A) corresponding to that of paspaline. In the case of transformant pSK63:PN2250 #8, a peak with the retention time of paspaline was barely detectable in the HPLC trace (FIG. 11, trace Ciii), but the EIC 422.305±0.01 m/z (FIG. 19A) confirmed the presence of paspaline. These results demonstrate successful restoration of the paspaline biosynthetic pathway in this KO mutant when the four core pax genes (paxGMBC) were introduced on these MIDAS-assembled multigene plasmids.

Figure 16:
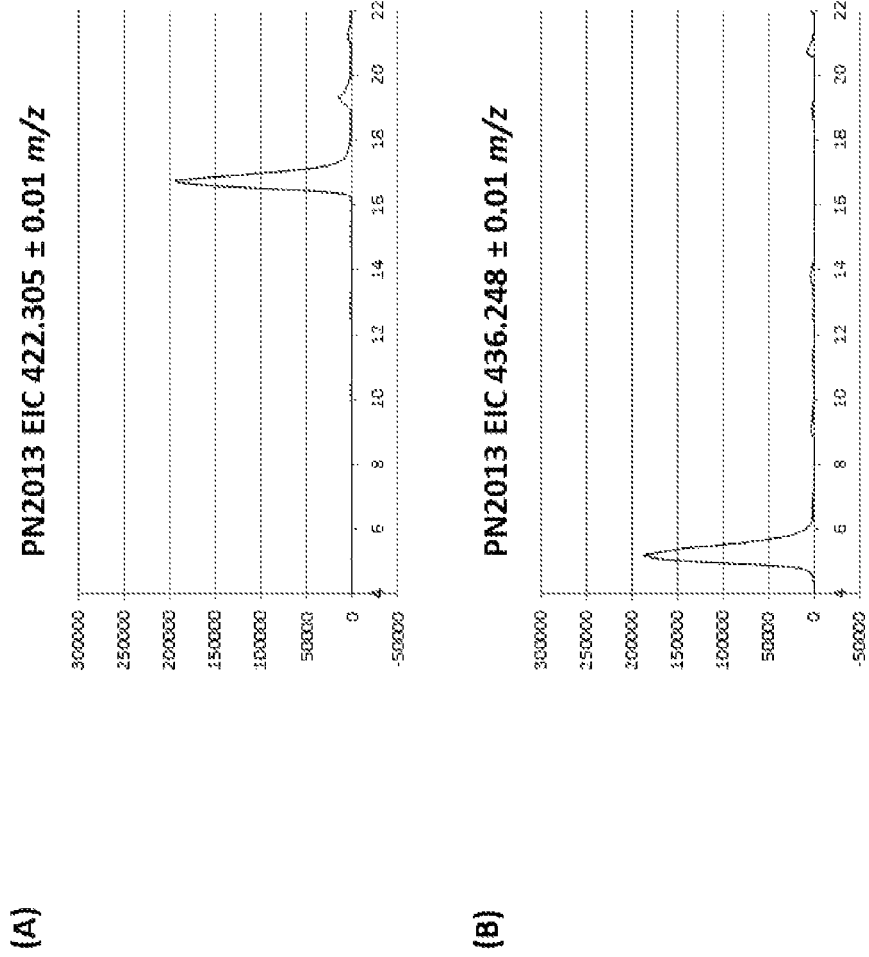
FIG. 16. Extracted ion chromatograms for wild type *P. paxilli* (strain PN2013) showing LC-MS peaks for (A) paspaline (17.6 minutes, m/z 422.305±0.01) and (B) paxilline (5.3 minutes, m/z, 436.248±0.01).
Figure 17:
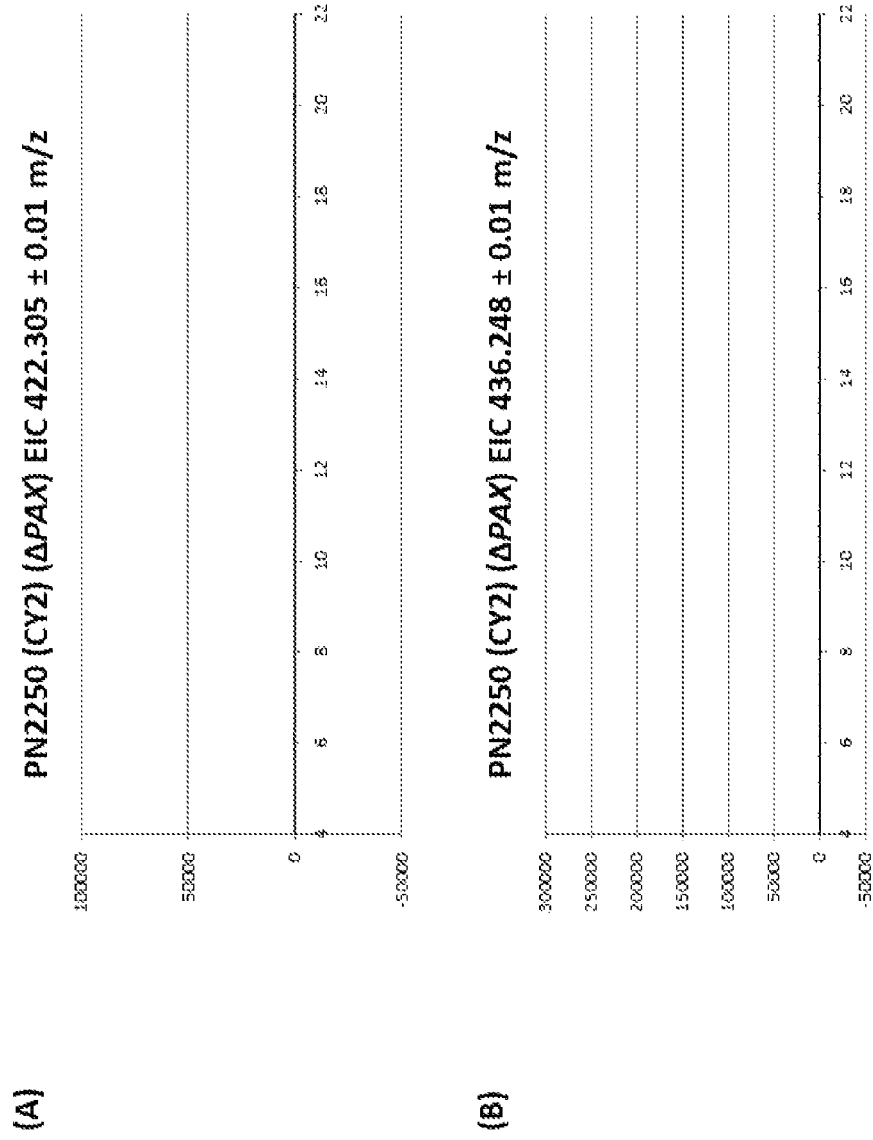
FIG. 17. Extracted ion chromatograms for *P. paxilli* ΔPAX mutant (strain PN2250 (CY2)) showing the absence of LC-MS peaks for (A) paspaline (17.6 minutes, m/z 422.305±0.01) and (B) paxilline (5.3 minutes, m/z, 436.248±0.01).
Figure 18:
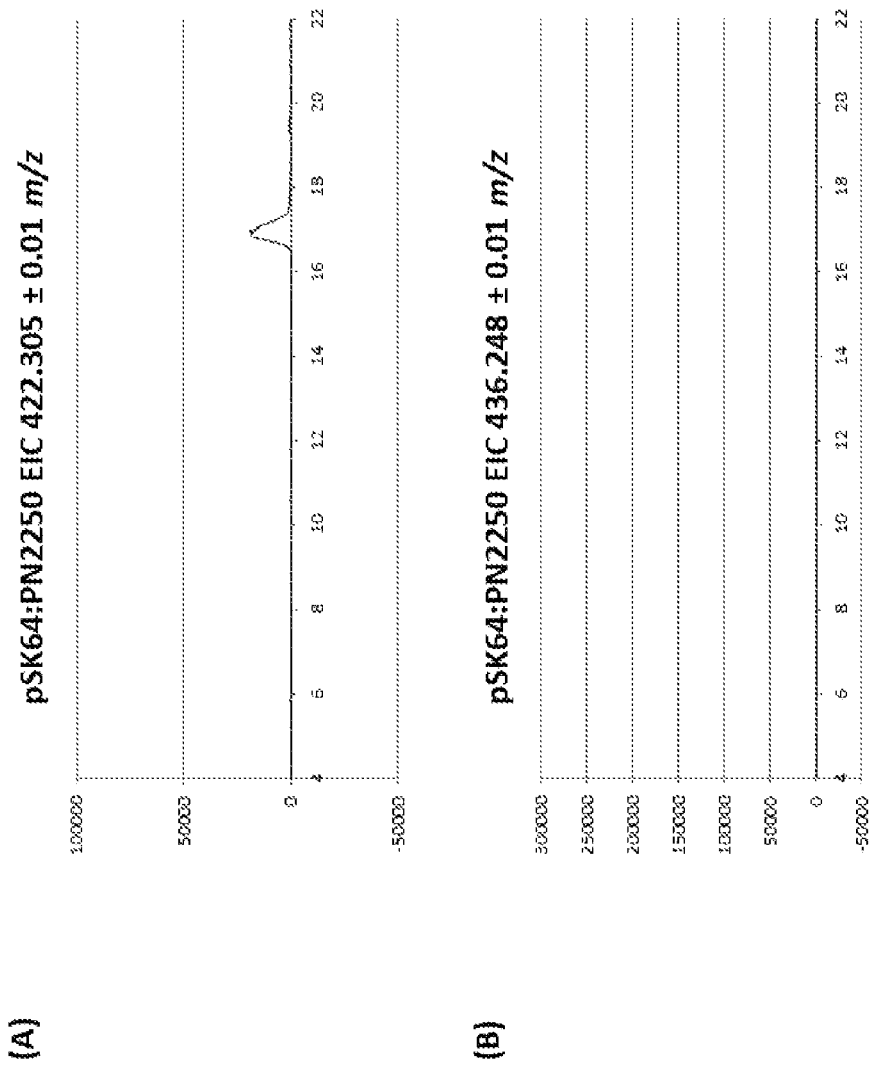
FIG. 18. Extracted ion chromatograms for pSK64:PN2250 transformant showing an LC-MS peak for (A) paspaline (17.6 minutes, m/z 422.305±0.01) but not (B) paxilline (5.3 minutes, m/z, 436.248±0.01).
Figure 19:
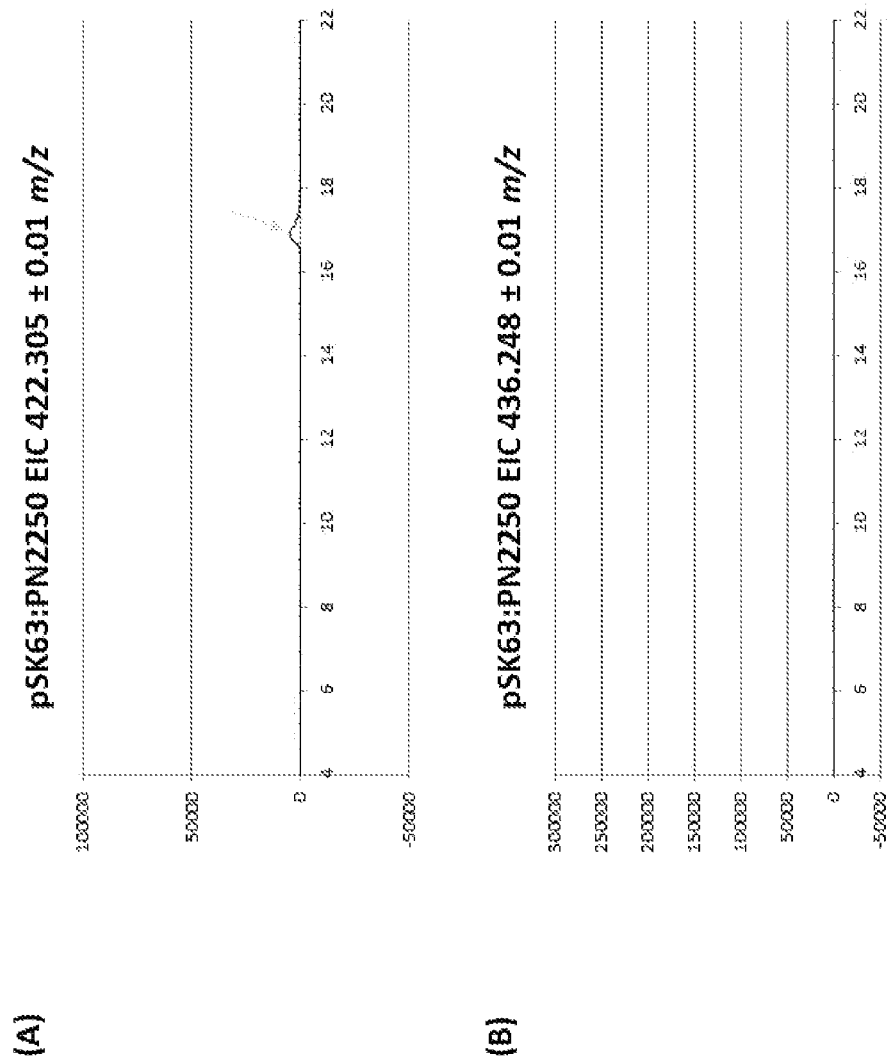
FIG. 19. Extracted ion chromatograms for pSK63:PN2250 transformant showing an LC-MS peak for (A) paspaline (17.6 minutes, m/z 422.305±0.01) but not (B) paxilline (5.3 minutes, m/z, 436.248±0.01). The arrow marks the position of the paspaline peak between 16 and 18.
Figure 21:
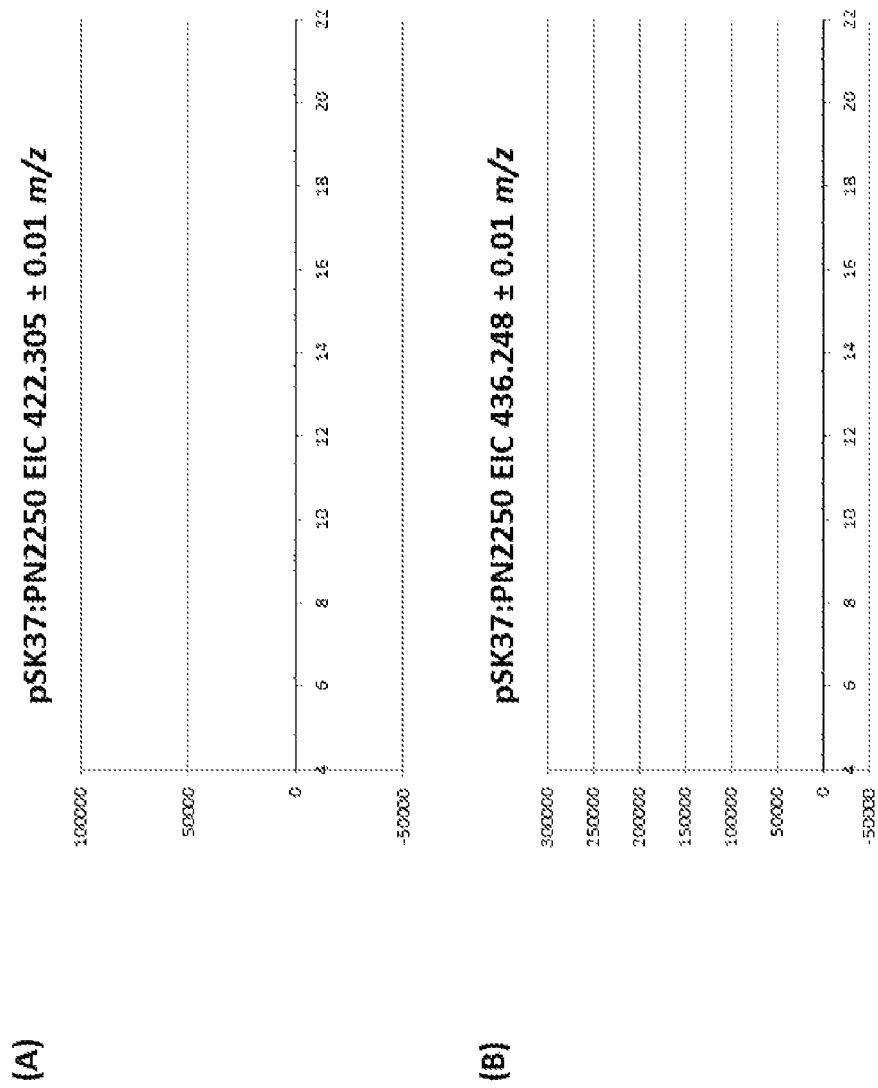
FIG. 21. Extracted ion chromatograms for pSK37:PN2250 transformant showing the absence of LC-MS peaks for (A) paspaline (17.6 minutes, m/z 422.305±0.01) and (B) paxilline (5.3 minutes, m/z, 436.248±0.01).
Figure 22:
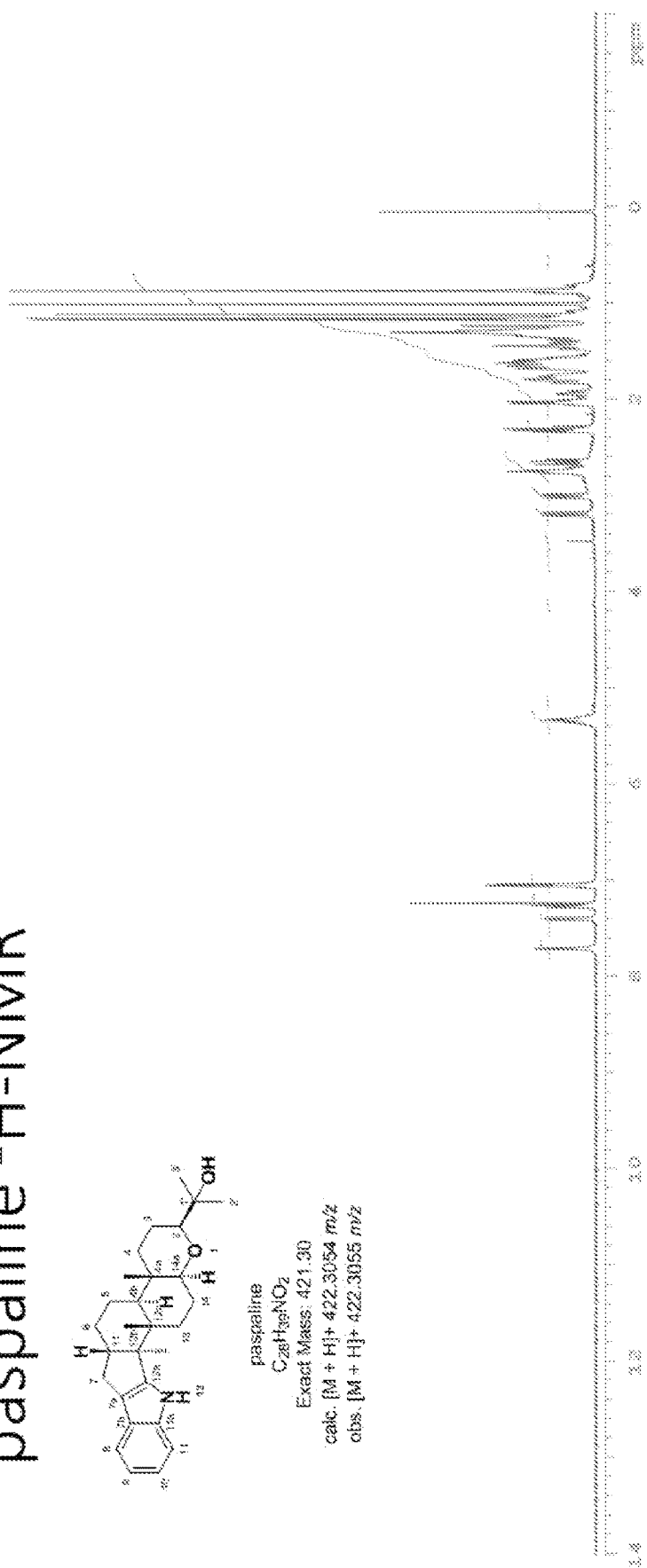
FIG. 22. $^1$H-NMR spectrum of paspaline.
Figure 23:
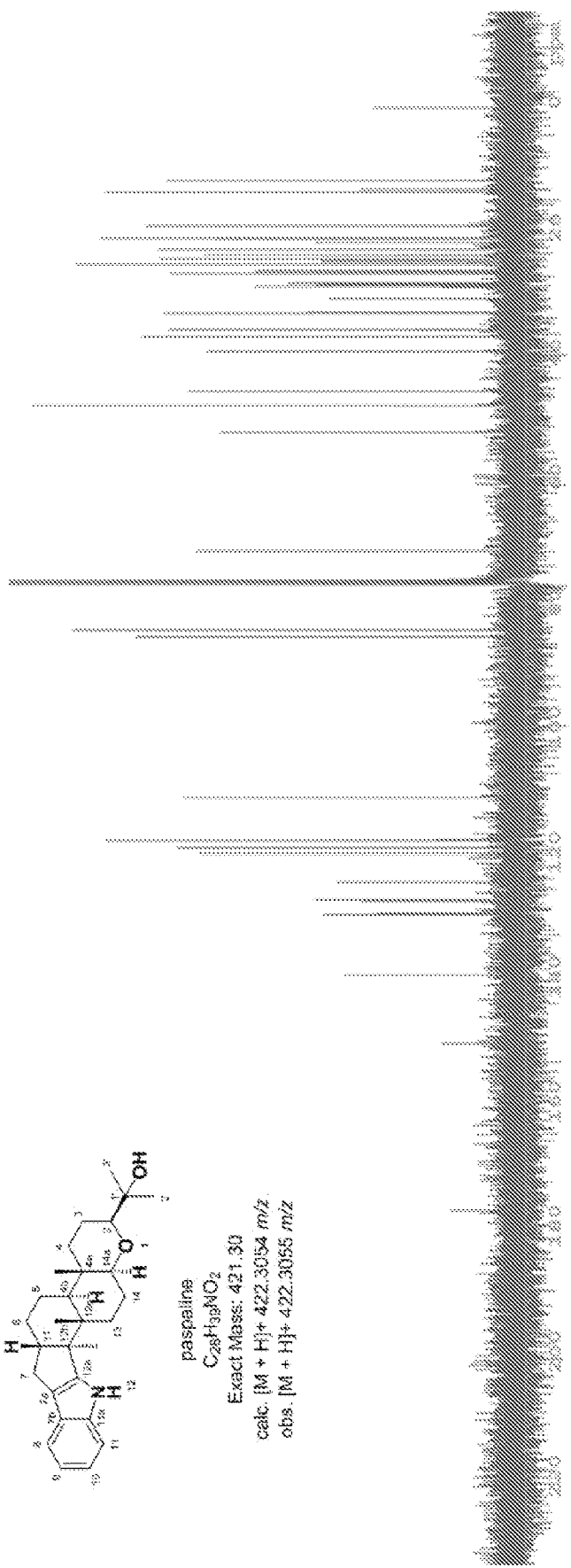
FIG. 23. $^{13}$C-NMR spectrum of paspaline.
Figure 24:
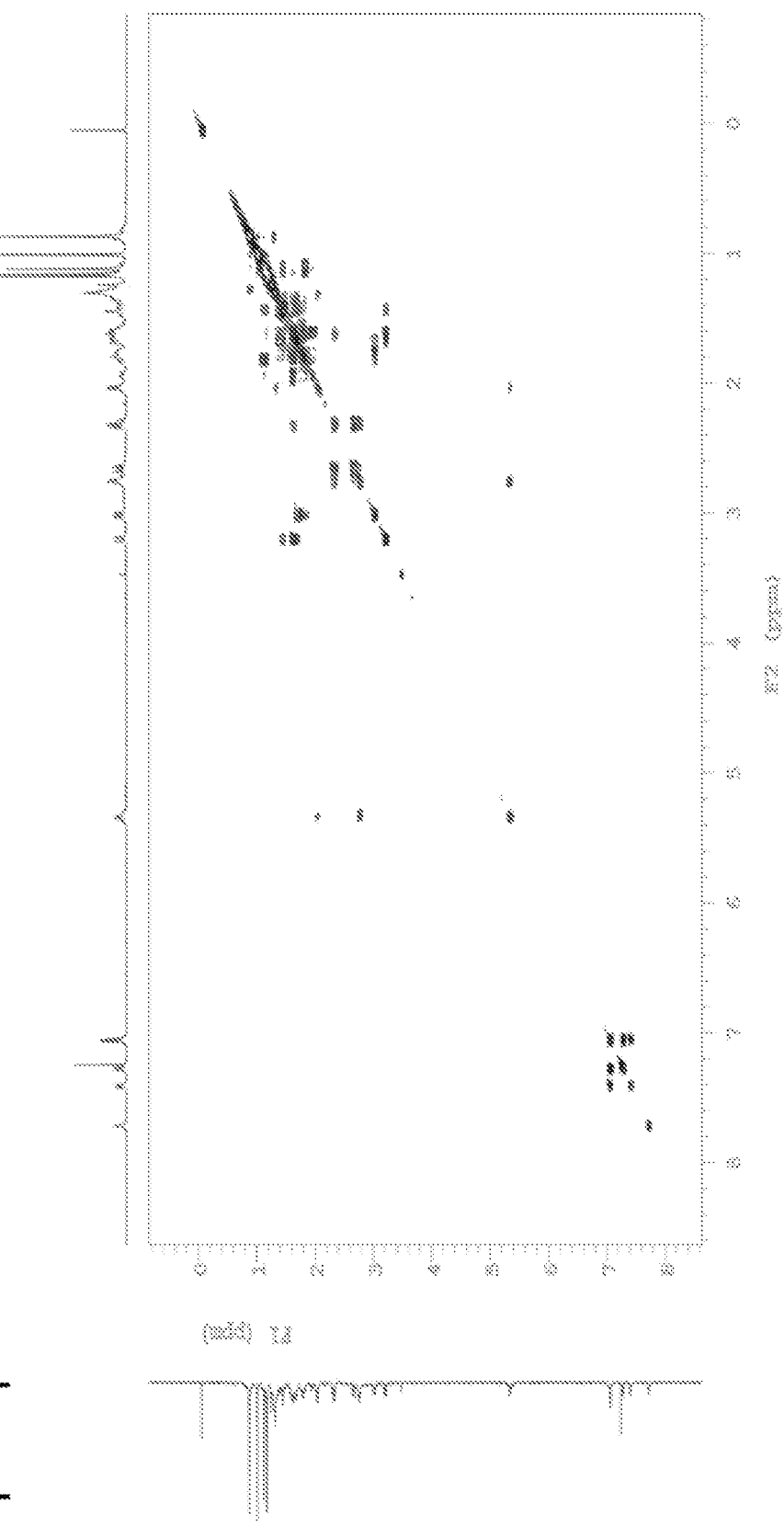
FIG. 24. $^1$H-$^1$H COSY-NMR spectrum of paspaline.
Figure 25:
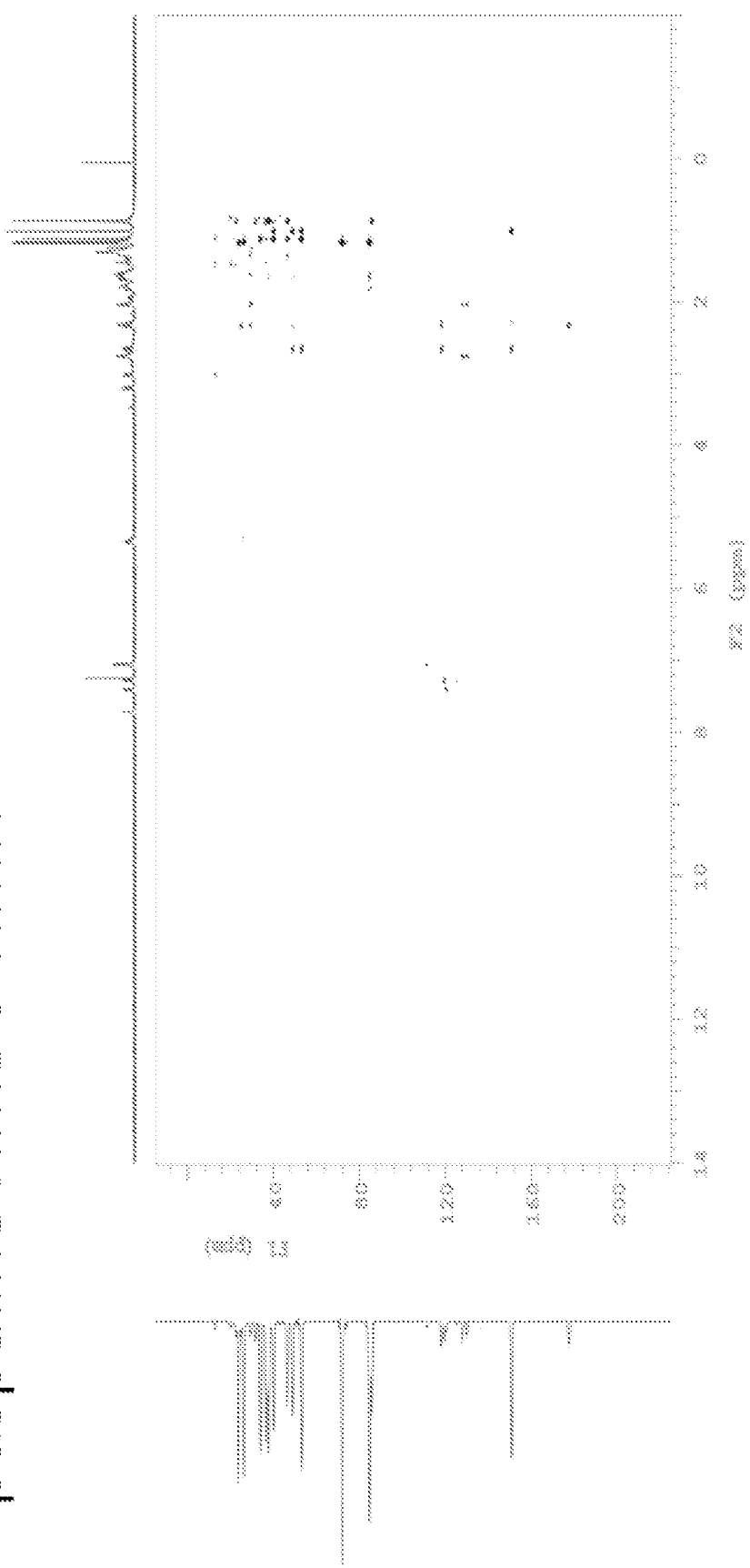
FIG. 25. HMBC-NMR spectrum of paspaline.
Figure 26:
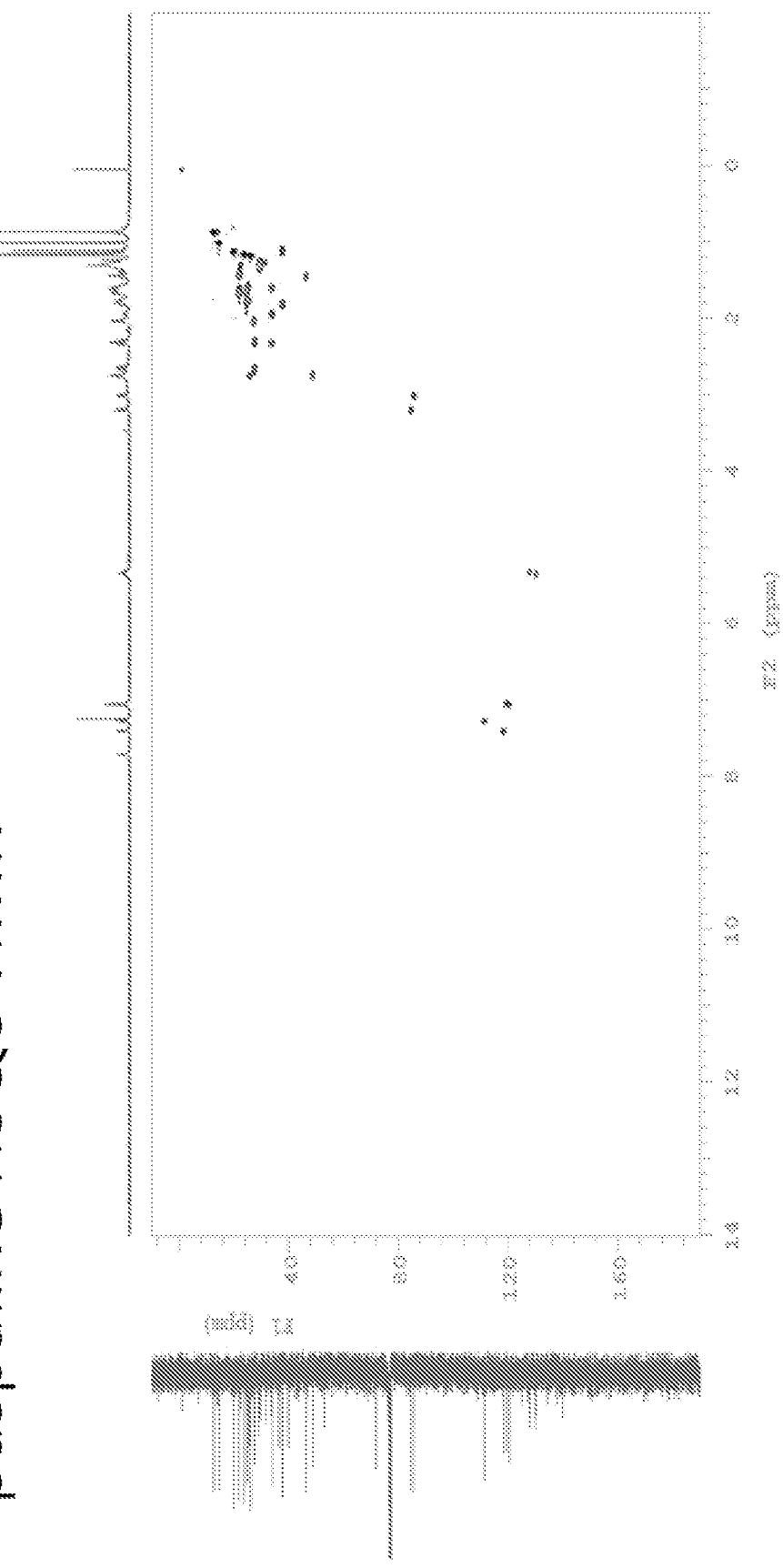
FIG. 26. HSQC-NMR spectrum of paspaline.
Figure 27:
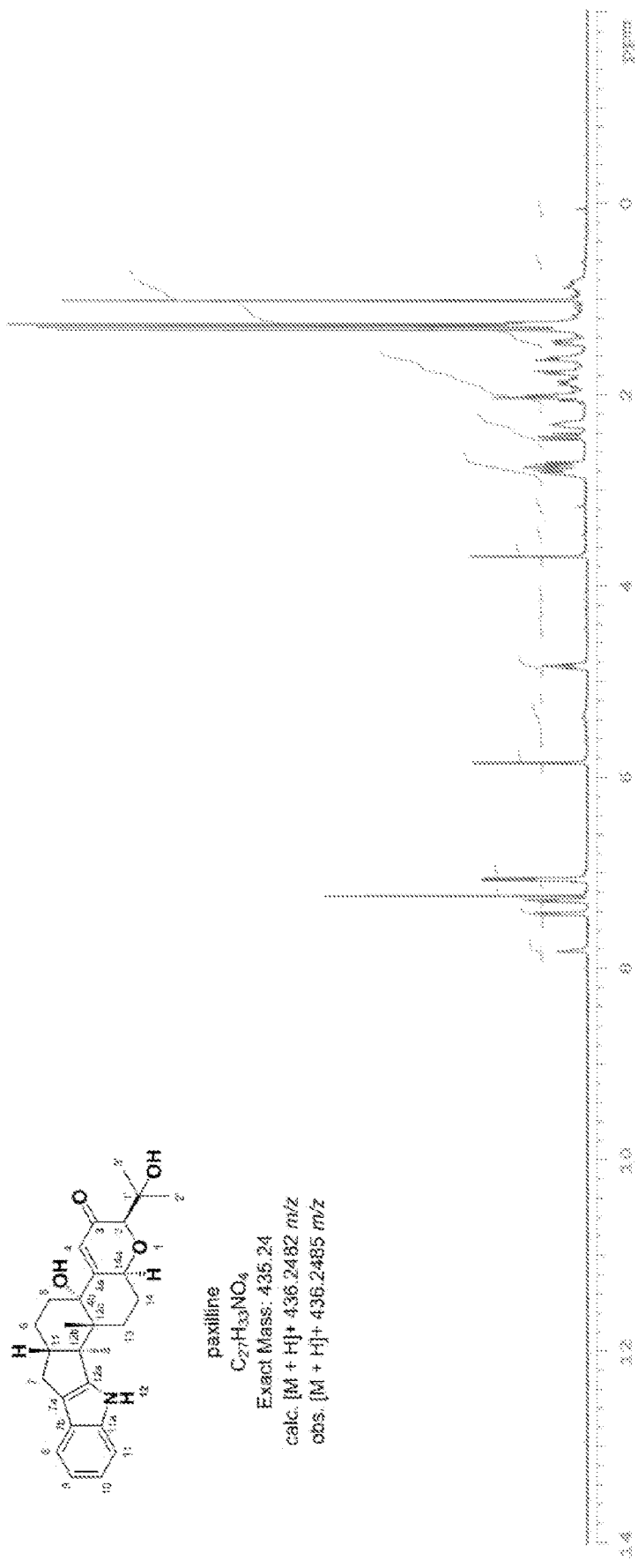
FIG. 27. $^1$H-NMR spectrum of paxilline.
Figure 28:
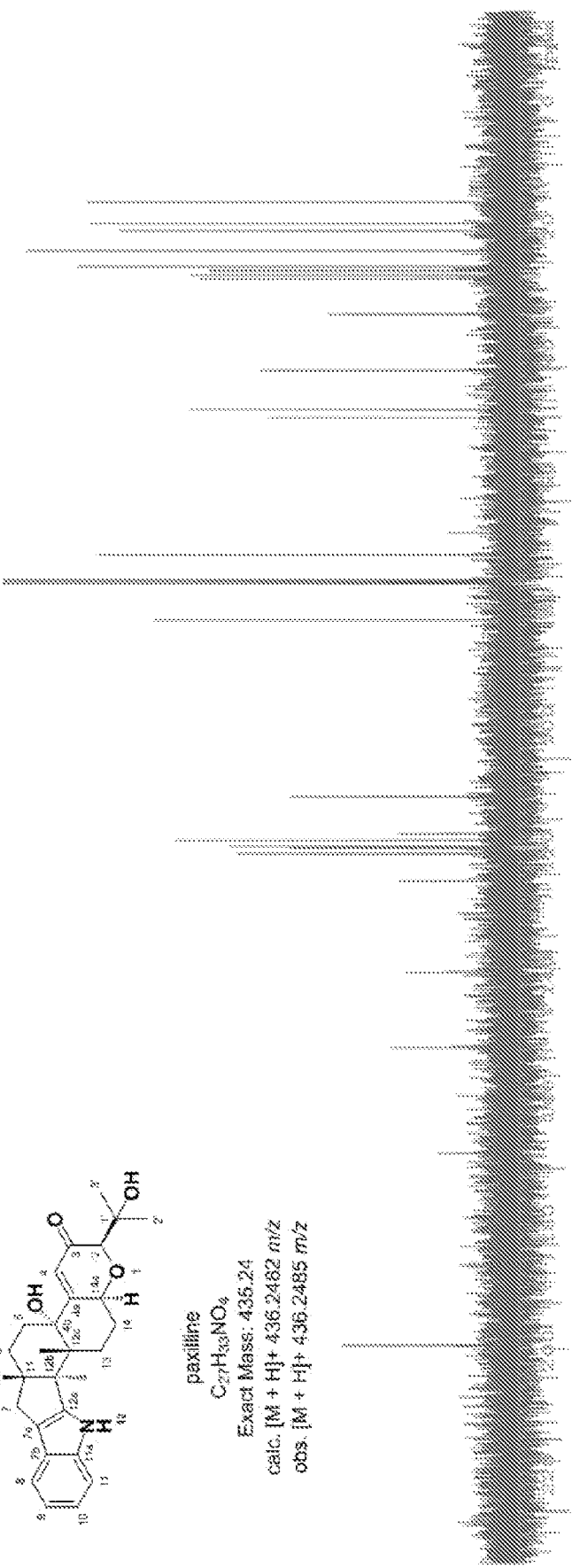
FIG. 28. $^{13}$C-NMR spectrum of paxilline.
Figure 29:
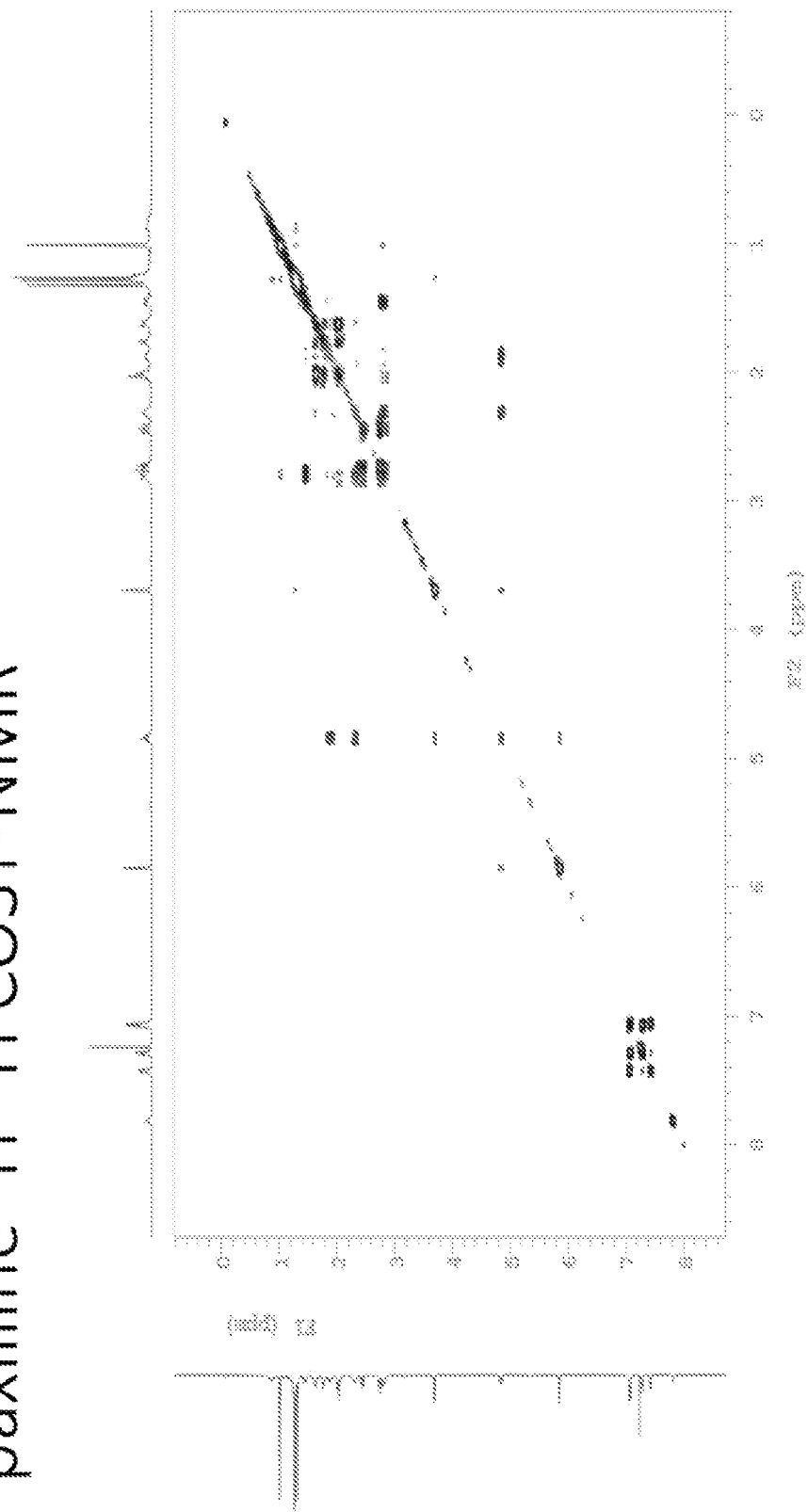
FIG. 29. $^1$H-$^1$H COSY-NMR spectrum of paxilline.
Figure 30:
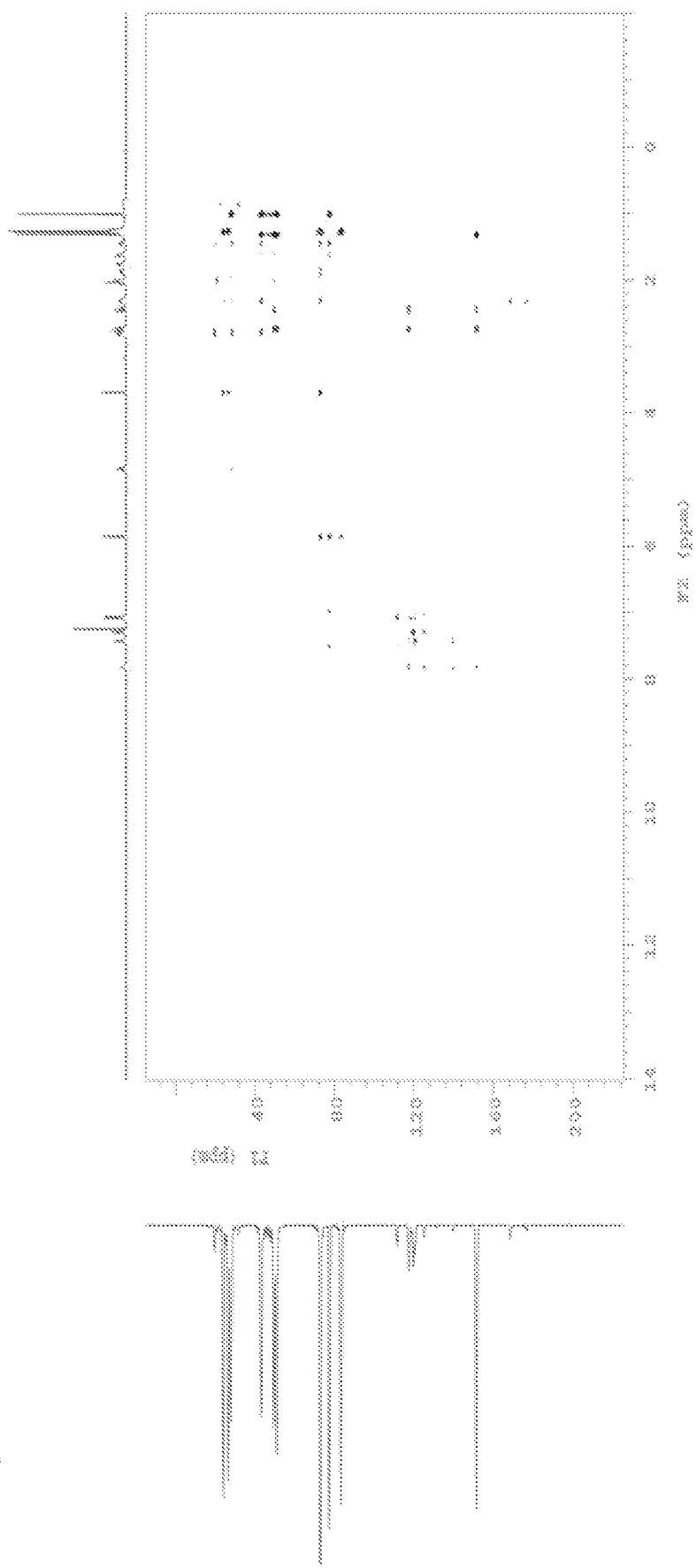
FIG. 30. HMBC-NMR spectrum of paxilline.
Figure 31:
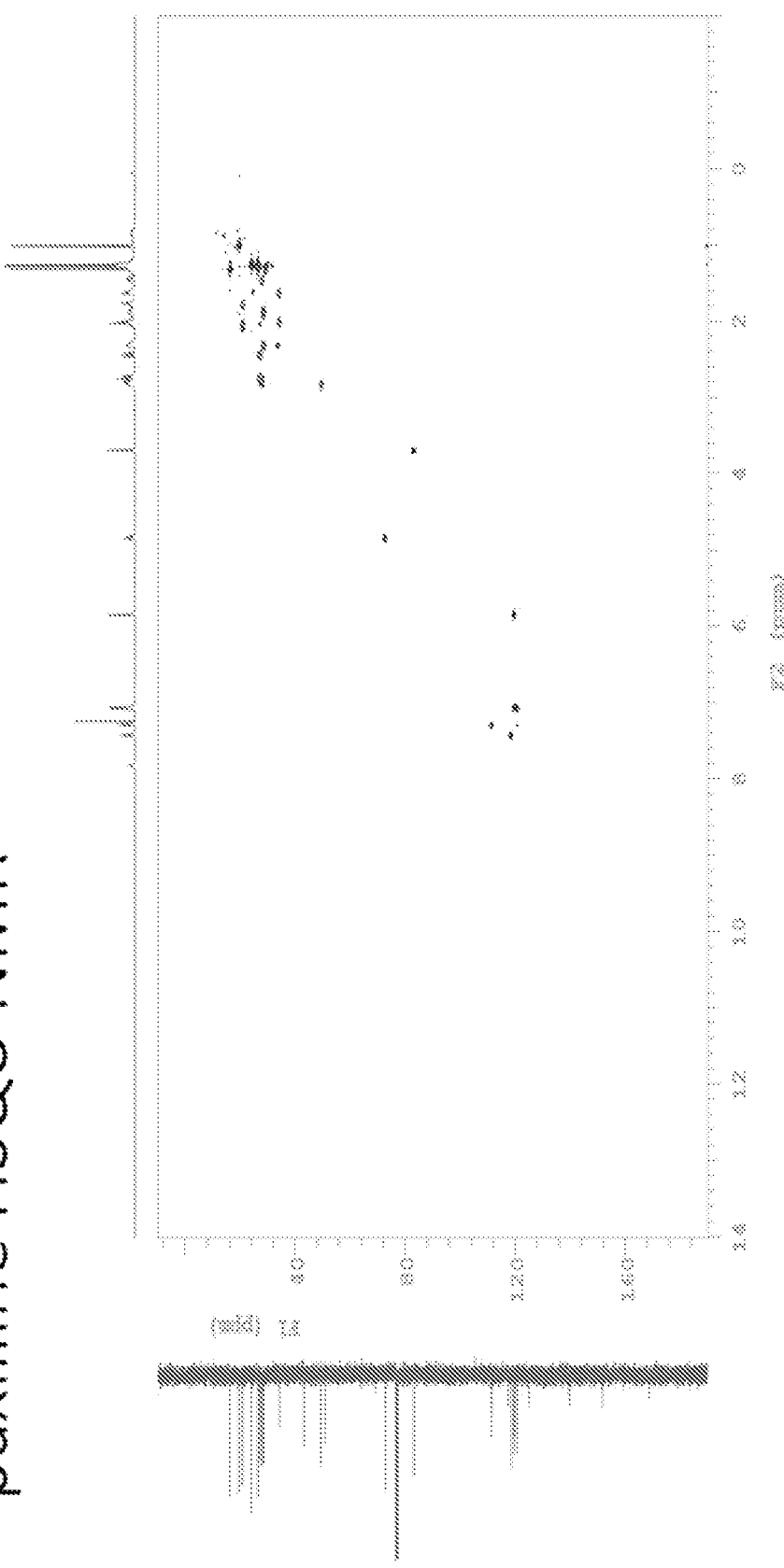
FIG. 31. HSQC-NMR spectrum of paxilline.

Due to the extensive deletion of the PAX cluster in parental strain PN2250 (CY2), which includes paxP and paxQ, as expected no paxilline was identified in the LC-MS analyses of these transformants (see FIGS. 18B and 19B). Also as expected, neither the parental strain, PN2250 (CY2), nor PN2250 (CY2) transformed with plasmid pSK37 (which harbours paxGMB, but not paxC), showed evidence of paspaline or paxilline in their extracts as assessed by HPLC (see FIG. 11, traces Ci and Civ, respectively) and EIC analysis (FIG. 17 and FIG. 21, respectively). This contrasts with the wild type strain (PN2013), which shows LC-MS peaks for both paspaline (17.6 min, 422.3055 m/z) and paxilline (5.3 min, 436.2485 m/z) (see FIG. 11, trace B and FIG. 16).

Restoration of Paxilline Production in a ΔPAX Deletion Mutant

Since gene disruption and chemical complementation experiments have shown that paxP and paxQ are required for the biosynthetic conversion of paspaline to paxilline (40), we also tested whether MIDAS-assembled multigene plasmids harbouring paxP and paxQ, in addition to the four core genes (paxGMBC), could restore production of paxilline in *P. paxilli* strain PN2250 (CY2). Therefore, plasmid pSK64 (harbouring the four core pax genes involved in paspaline biosynthesis, all under the control of their native promoters) was loaded sequentially with a paxP TU (from pSK73) to produce pSK78, and then with a paxQ TU (from pSK74) to produce plasmid pSK79, which harbours 6 pax genes in total.

Figure 13:
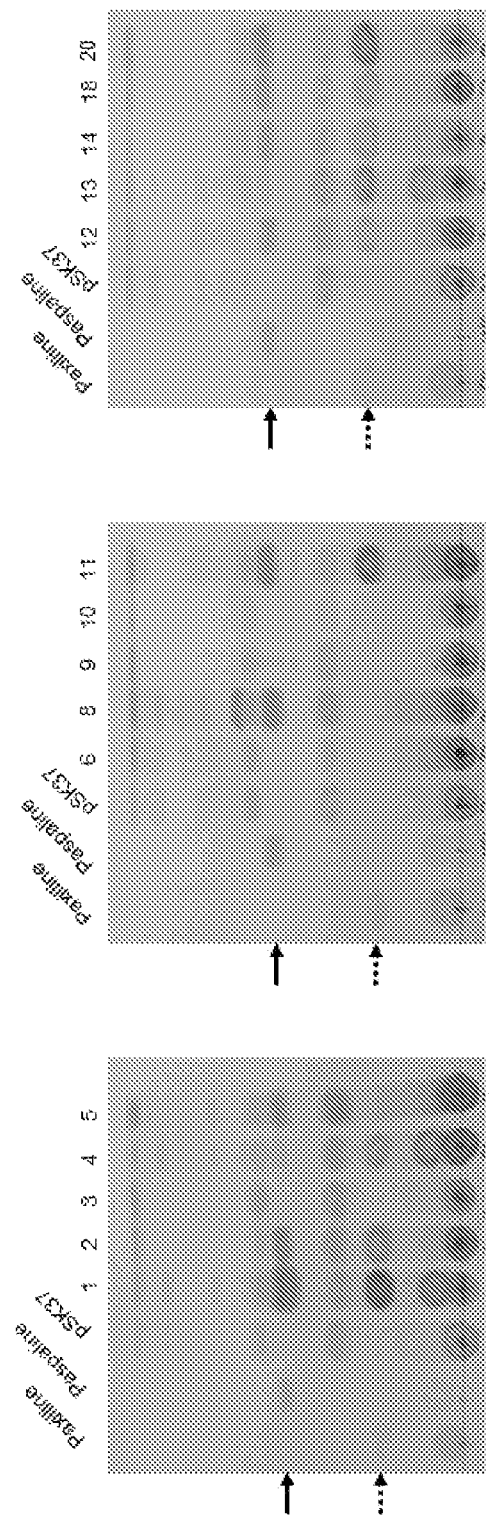
FIG. 13. Thin layer chromatography (TLC) analysis of mycelial extracts from pSK79 transformants of *P. paxilli* PN2250 (CY2). In order to screen pSK79 transformants for production of IDTs, 2-butanone extracts of fungal mycelia were chromatographed, alongside purified paspaline and paxilline reference standards, on normal phase TLC plates and visualized with Ehrlich's reagent. The migratory positions of the paspaline and paxilline reference standards are indicated by the solid and dashed arrows, respectively. Fungi transformed with plasmid pSK37 acted as a negative control (lanes labelled "pSK37"). Of the 15 fungal lines analysed following transformation of *P. paxilli* PN2250 (CY2) with plasmid pSK79, nine (lines 1, 2, 4, 11, 12, 13, 14, 18 and 20) showed evidence for the presence of both paxilline and paspaline in their extracts. Line 5 showed evidence of paspaline, but the paxilline phenotype was less clear by TLC. Four lines (3, 6, 9 and 10) produced neither paspaline nor paxilline. Line 8 also did not produce paxilline, but did produce paspaline and a compound (still to be characterised) that migrates above the papsaline in the TLC. As expected, fungi transformed with plasmid pSK37 produced no paspaline or paxilline.
Figure 20:
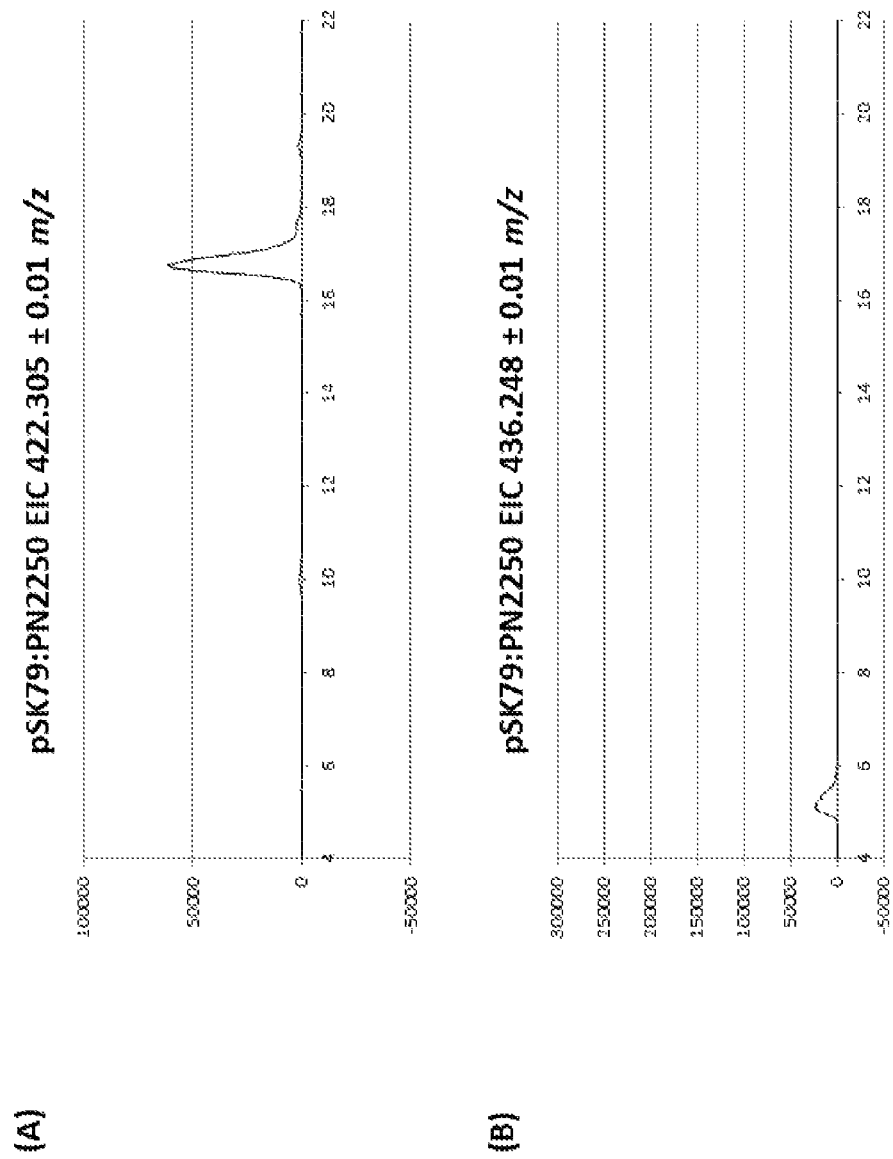
FIG. 20. Extracted ion chromatograms for pSK79:PN2250 transformant showing LC-MS peaks for (A) paspaline (17.6 minutes, m/z 422.305±0.01) and (B) paxilline (5.3 minutes, m/z, 436.248±0.01).

Plasmid pSK79 was transformed into *P. paxilli* PN2250 (CY2) and, of the 15 geneticin resistant lines screened by TLC, nine showed the presence of both paspaline and paxilline in their extracts (FIG. 13). LC-MS analysis of transformant pSK79:PN2250 #14 identified peaks with retention times (FIG. 11, trace Cv) and EIC masses (FIG. 20) corresponding to that of paspaline and paxilline, thereby confirming successful restoration of the paxilline biosynthetic pathway in this KO strain.

Paxilline Production Using Bacterial Artificial Chromosomes (BAC)

To demonstrate the principles of MIDAS, the Level-3 destination vector used thus far in this work (i.e., pML3) was designed with the high copy number pMB1 replicon (from pUC19) for ease of handling (i.e., high plasmid yields for restriction digestion and sequencing analysis). Although theoretically capable of indefinite growth, such high copy number, pMB1-based vectors will undoubtedly, at some point, encounter limitations relating to the stability of specific cloned sequences and/or size of insert. To ameliorate these potential issues, a Level-3 destination plasmid based on bacterial artificial chromosomes (BACs) could permit the cloning and stable maintenance of very large assemblies. BAC vectors harbouring an inducible replication element for on-demand control of copy number offer a particularly attractive way of building large metabolic arrays that could be stably maintained in *E. coli*.

To demonstrate the feasibility of BAC-based multigene assemblies, a Level-3 destination vector (named pML3-BAC) was also constructed, based on pSMART® BAC v2.0 (Lucigen, USA). The pML3-BAC destination vector, and derived multigene assemblies cloned into pML3-BAC, were propagated in *E. coli* BAC-Optimized Replicator v2.0 cells (Lucigen, USA) in the presence of 12.5 µg/mL chloramphenicol. For induction of high copy number, 0.01% L-arabinose was included in the culture medium. Construction of MIDAS Level-3 (multigene) assemblies in pML3-BAC proceeds in exactly the same way as for construction of multigene assemblies in pML3, i.e., by alternating AarI- and BsmBI-mediated Golden Gate reactions with TUs cloned into "White" and "Blue" pML2 shuttle vectors, respectively.

Figure 32:
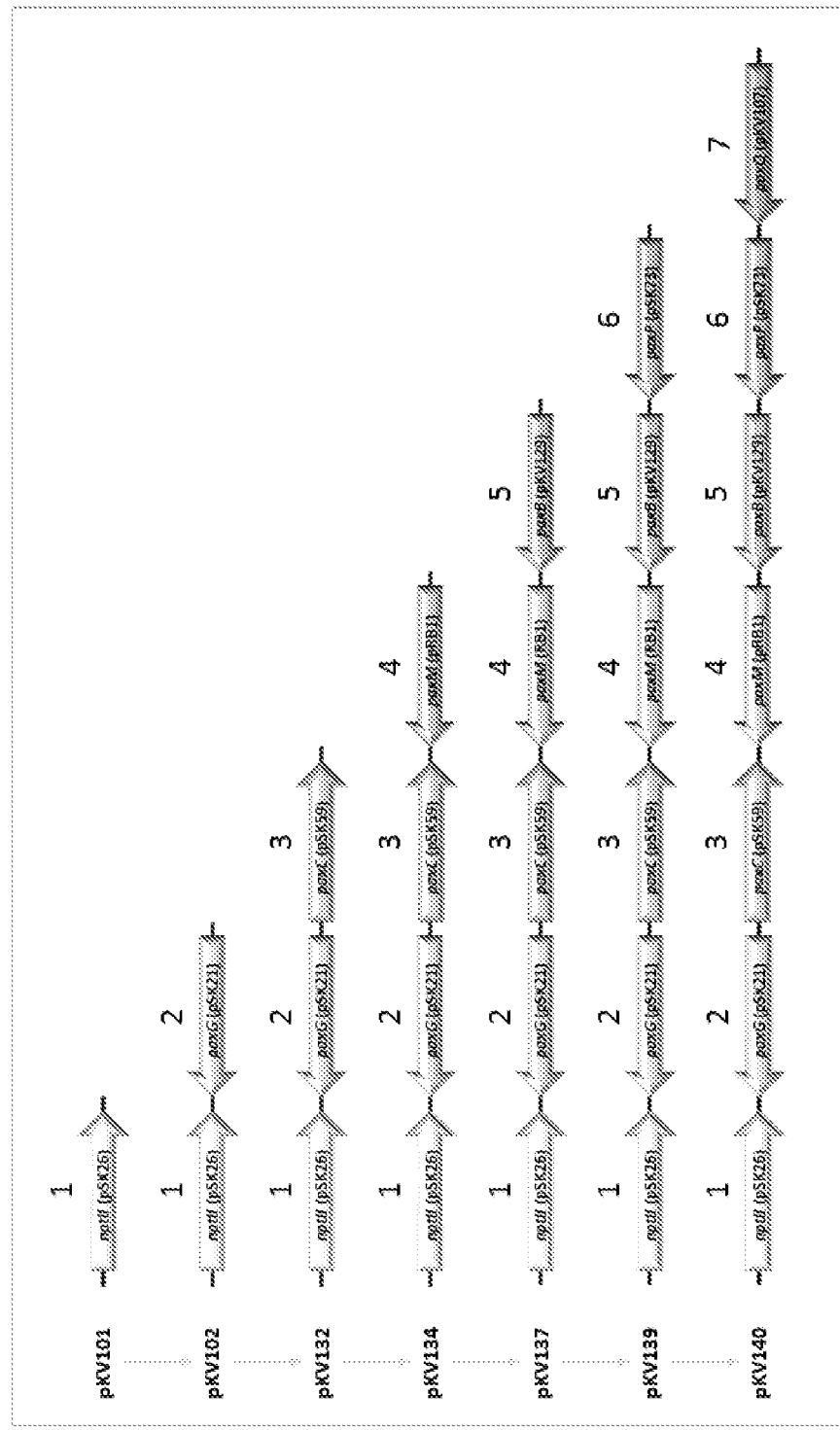
FIG. 32. MIDAS Level-3 bacterial artificial chromosome (BAC)-based multigene assemblies produced in this work. For reconstructing the paxilline biosynthetic pathway in *P. paxilli* strain PN2253 (LM662) using a bacterial artificial chromosome (BAC)-based Level-3 destination vector, multigene assemblies were produced by sequentially loading the TUs for nptII, paxG, paxC, paxM, paxB, paxP and paxQ into pML3-BAC. The order in which each TU was loaded is shown by the numerals above each TU. Strain PN2253 (LM662) contains a deletion of the entire PAX cluster.
Figure 33:
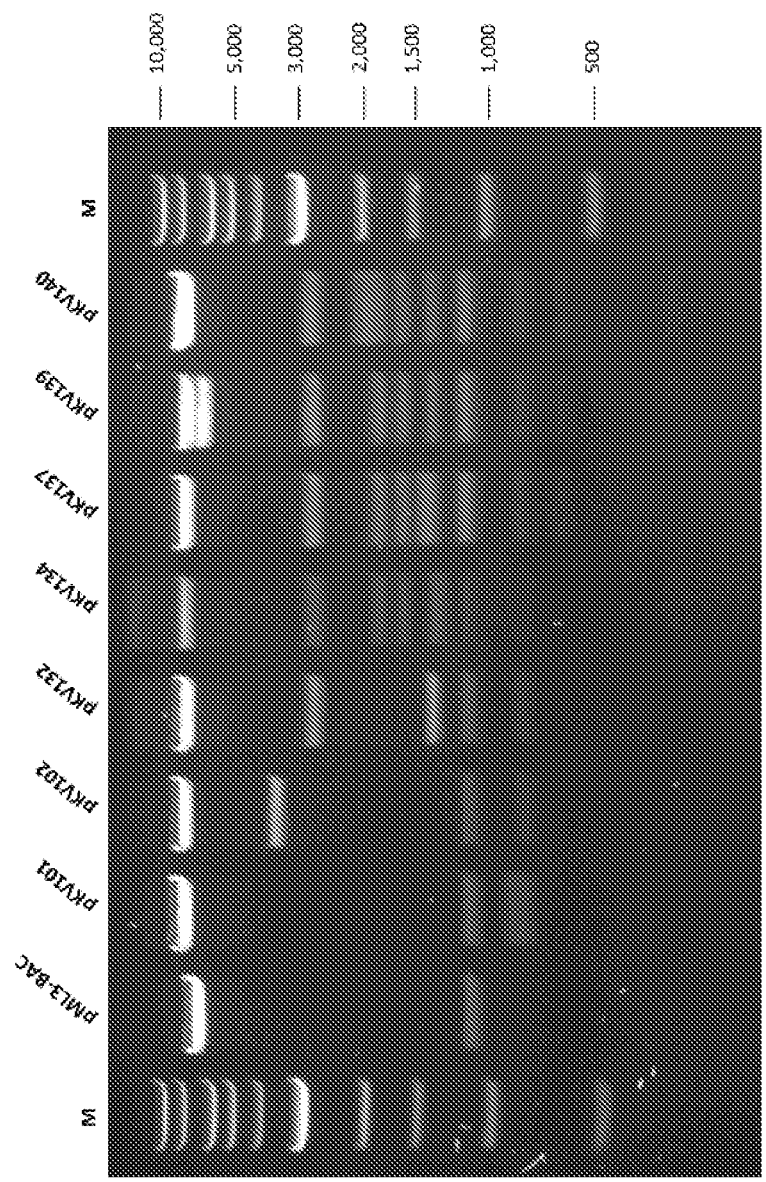
FIG. 33. Restriction digestion analysis of MIDAS Level-3 BAC assemblies. Plasmid DNA prepared from pML3-BAC and one colony per BAC assembly reaction was digested with NcoI and reactions were electrophoresed on a 0.8% (w/v) agarose-TAE gel stained with SYBR® Safe (Thermo Fisher Scientific). Expected sizes (bp) of fragments are listed as follows, with the transcription units harboured by each construct shown in parentheses. pML3-BAC: 6767, 1157; pKV101 (nptII): 7542, 1157, 910, 839; pKV102 (nptII-paxG): 7542, 3571, 1157, 839; pKV132 (nptII-paxG-paxC): 7542, 2860, 1465, 1447, 1157, 839; pKV134 (nptII-paxG-paxC-paxM): 7542, 2860, 1983, 1740, 1447, 1379, 1157, 839, 222; pKV137 (nptII-paxG-paxC-paxM-paxB): 7542, 2860, 1983, 1740, 1539, 1447, 1187, 1157, 839, 652, 222; pKV139 (nptII-paxG-paxC-paxM-paxB-paxP): 7542, 6359, 2860, 1983, 1740, 1447, 1187, 1157, 839, 652, 222; pKV140 (nptII-paxG-paxC-paxM-paxB-paxP-paxQ): 7664, 7542, 2860, 2156, 1983, 1740, 1447, 1187, 1157, 839, 652, 222. M: Quick-Load® Purple 1 kb DNA ladder from New England Biolabs Inc. All clones showed the expected pattern of bands following restriction enzyme digestion.

The paxilline biosynthetic pathway was assembled into pML3-BAC by sequentially loading the TUs for nptII, paxG, paxC, paxM, paxB, paxP and paxQ (FIG. 32), with the final plasmid (pKV140) harbouring all seven TUs. Colonies derived from each assembly reaction were selected for plasmid DNA purification and restriction digestion analysis, and a representative restriction digestion analysis showing each of the correctly assembled plasmids is presented in FIG. 33.

Figure 34:
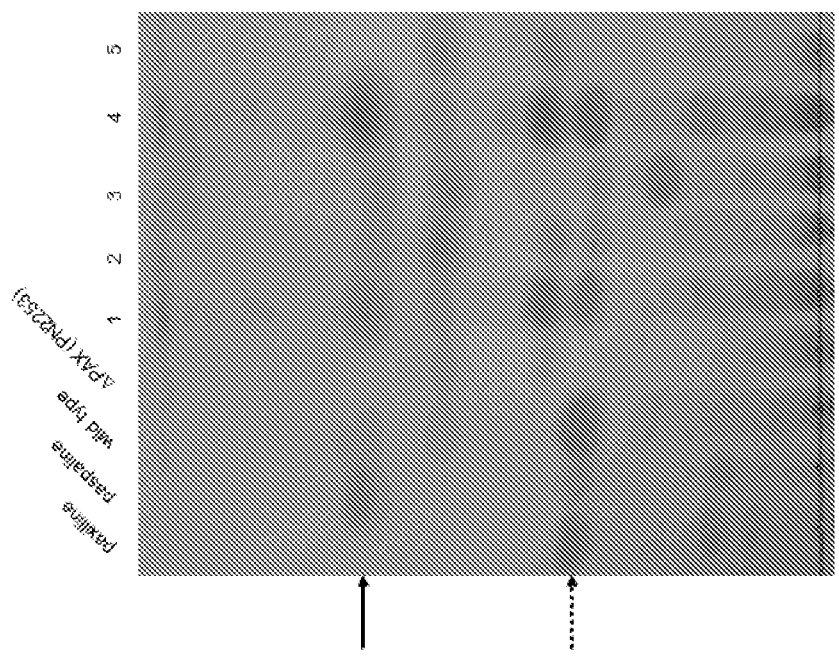
FIG. 34. Thin layer chromatography (TLC) analysis of mycelial extracts from pKV140 transformants of *P. paxilli* PN2253 (LM662). To screen transformants for production of IDTs, 2-butanone or ethyl acetate extracts of fungal mycelia were chromatographed, alongside purified paspaline and paxilline reference standards, on normal phase TLC plates and visualized with Ehrlich's reagent. The migratory positions of the paspaline and paxilline reference standards are indicated by the solid and dashed arrows, respectively. Of the five fungal lines analysed following transformation of *P. paxilli* PN2253 (LM662) with BAC pKV140, four (lines 1 to 4) showed evidence of paxilline and paspaline production and one (line 5) showed neither paxilline nor paspaline production.
Figure 35:
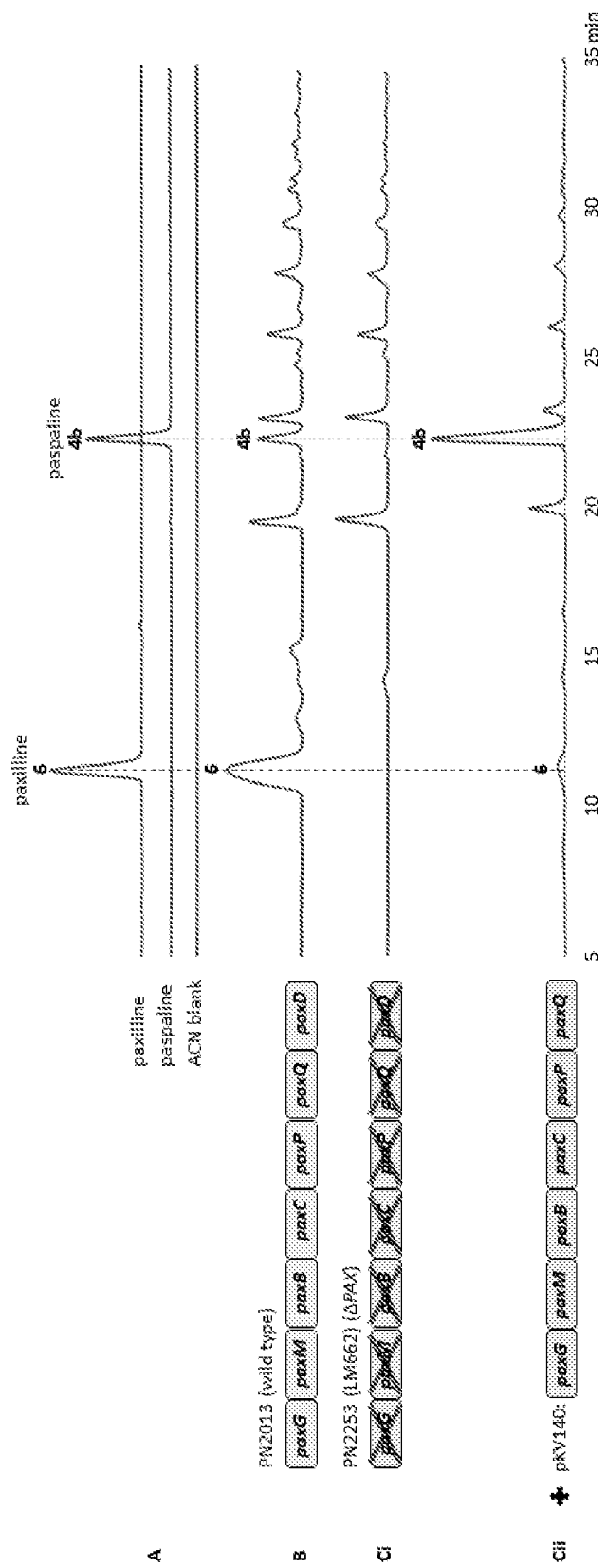
FIG. 35. HPLC analysis of extract from *P. paxilli* PN2253 (LM662) transformed with pKV140 BAC. HPLC analysis (280 nm) was used for identification of IDTs extracted from fungal mycelia. (A) Overlaid HPLC traces of paxilline, paspaline, and acetonitrile, ACN (blank) reference standards. (B) HPLC trace of wild type strain PN2013, showing the presence of paxilline and paspaline. An HPLC trace of the ΔPAX KO mutant PN2253 (LM662) is shown (trace Ci) and an HPLC trace following transformation of this mutant with the pKV140 BAC is shown (Cii). The boxes to the left of the HPLC traces show the genotypes of each *P. paxilli* strain and the genotype of the transforming BAC, with a cross (X) indicating the pax genes that have been deleted from the genome of the knockout strain. As expected, paxilline and paspaline are absent from the parental ΔPAX strain PN2253 (LM662) as assessed by HPLC (trace Ci). For transformant pKV140:PN2253 (Cii), peaks corresponding to paxilline and paspaline were identified, notably at inversed titres relative to the PN2013 wildtype strain (i.e. the transformant produced an exceptionally high amount of paspaline and relatively low amount of paxilline).

Plasmid pKV140 was transformed into the *P. paxilli* ΔPAX knockout strain PN2253 (LM662), which contains a deletion of the entire PAX cluster and, of the 5 geneticin resistant lines screened by TLC, four showed the presence of both paspaline and paxilline in their extracts (FIG. 34). HPLC analysis of one of the TLC-positive transformants identified peaks with retention times (FIG. 35, trace Cii) corresponding to that of paspaline and paxilline, thereby confirming successful restoration of the paxilline biosynthetic pathway in this KO strain using the BAC-based Level-3 destination vector pML3-BAC.

Tables 1-15 referenced in this specification are set out below:

TABLE 1

PCR primers used in the construction of the pML1 source vector.
Spec$^R$ denotes spectinomycin resistance.

| PCR name (Size, bp) | Plasmid fragment | Fragment description | Template (source/ reference) | Primer name (length): Primer sequence (5' to 3') | SEQ ID NO. |
|---|---|---|---|---|---|
| CV-161 (1125) | BsaI[ACCG]- P$_{aadA}$-Spec$^R$- [GAAT]BsaI | Bacterial spectinomycin resistance gene driven by te aadA promoter | pBB535 (41) | cvd2016-01-13a (41-mer): cgctcacggtctcaACCGgacgtcgatatccggatg aaggc | 10 |
| | | | | cvd2016-01-13b (45-mer): tgaacgaggtctcaATTCttatttgccgactacctt ggtgatctc | 11 |
| CV-162 (591) | BasI[GAAT]- f1ori- [GTGT]BsaI | Bacteriophage f1 origin of replication | pET -28a(+) (Novagen) | cvd2016-01-13c (55-mer): gatgagttggtctcaGAATtaattcatgagcggata catatttgaatgtatttag | 12 |
| | | | | cvd2015-11-18d (35-mer): gaggaacggtctccACACtggcgaatgggacgcgc | 13 |
| CV-74 (372) | BsaI[GTGT]- lacZα- [GGCA]BsaI | Wildtype laxZα fragment, driven by the lac promoter. | E. coli K12 ER2925 (New England Biolabs) | cvd2015-05-28b (47-mer): ctttccggtctcaGTGTccatggttattaccaggca aagcgccattc | 14 |
| | | | | cvd2015-05-28k (54-mer): gacaggtttggtctcgTGCCctcgagcagctggcg aacgcaattaatgtgagt | 15 |
| CV-152 (1070) | BsaI[GGCA]- pMB1 ori- [ACCG]BsaI | Bacterial pMB1 plasmid origin of replication. | pUC19 (Clontech Laboratories, Inc.) | cvd2015-11-18a (39-mer): cacattaaggtctctGGCAtcactgcccgctttcca gtc | 16 |
| | | | | cvd2015-11-18b (50-mer): tgattaggtctcgCGGTctgtcagaccaagtttact catatatactttag | 17 |
| CV-81 (367) | NcoI- [CTCG]BsmI- laxZα-BsmBI [AGAC]-XhoI | Fragment containing the pML1 Golden Gate cloning cassette, i.e., lacZα (driven by the lax promoter) flanked by divergent BamBI recognition sites. | E. coli K12 ER2925 (New England Biolabs) | cvd2015-05-28d (50-mer): cagctttcccatgttCTCGtgagacgttattaccag gcaaagcgccattc | 18 |
| | | | | cvd2015-05-281 (46-mer): tcccgacctcgagGTCTagagacggcgaacgcaat taatgtgagt | 19 |

TABLE 2

PCR primers used in the construction of the pML2 shuttle vectors.
Kan$^R$ denotes kanamycin resistance.

| PCR name (Size, bp) | Plasmid fragment | Fragment description | Template (source/ reference) | Primer name (length): Primer sequence (5' to 3') | SEQ ID NO. |
|---|---|---|---|---|---|
| CV-153 | BsaI[ACCG]- Kan$^R$- [TTTG]-BsaI | Bacterial kanamycin resistance gene driven by the kan promoter | pET -28a(+) (Novagen) | cvd2015-11-18c (40-mer): agaagatccggtctccACCGctacggggtctgacgc tcag | 20 |
| | | | | cvd2015-06-17a (38-mer): gattcgcgggtctccCAAAcgaaatacgcgatcgct gtt | 21 |
| | BsaI[TTTG]- KAN$^R$-f1ori- [GTGT] | | pET -28a(+) (Novagen) | cvd2015-06-17b (37-mer) domestication primer): atcgcgggtctcgTTTGgctcaggcgcaatcacgaa t | 22 |
| | | | | cvd2015-11-18d (35-mer): gaggaacggtctccACACtggcgaatgggacgcgc | 23 |
| CV-77 (363) | BsaI[GTGT]- laxZα- [GGCA]BsaI | Wild type laxZα fragment, driven by the lac promoter. | E. coli K12 ER2925 (New England Biolabs) | cvd2015-05-22b (47-mer): ctttccggtctcaGTGTccatggttattaccaggca aagcgccattc | 24 |
| | | | | cvd2015-05-22g (46-mer): cccgacggtctcgTGCCctcgaggcgcaacgcaatt aatgtgagtt | 25 |
| CV-152 (1070) | BsaI[GGCA]- pMB1ori- [ACCG]BsaI | Bacterial pMB1 plasmid origin of replication. | pUC19 (Clontech Laboratories, Inc. | cvd2015-11-18a (39-mer): cacattaaggtctctGGCAtcactgcccgctttcca gtc | 26 |
| | | | | cvd2015-11-18b (50-mer): tgattaggtctcgCGGTctgtcagaccaagtttact catatatactttag | 27 |

TABLE 2-continued

PCR primers used in the construction of the pML2 shuttle vectors.
Kan$^R$ denotes kanamycin resistance.

| PCR name (Size, bp) | Plasmid fragment | Fragment description | Template (source/ reference) | Primer name (length): Primer sequence (5' to 3') | SEQ ID NO. |
|---|---|---|---|---|---|
| CV-78 (376) | BsaI[CATT] AarI-lacZα- AarI[CGTA] BsaI | Wild type lacZα fragment, driven by the lac promoter. | E. coli K12 ER2925 (New England Biolabs) | cvd2015-05-22h (53-mer): agccagcggtctcaCATTgcttgcaggtgttattac caggcaaagcgccattg | 28 |
| | | | | cvd2015-05-22i (52-mer): caggtttcggtctcgTACGgcgggcaggtggcgcaa cgcaattaatgtgagt | 29 |
| CV-129 (140) | [GGAG]BsaI- P$_{ca}$▶ BsaI[TAAA] | Chloramphenicol acetyltransferase (cat) promoter | pBB528 (41) | cvd2015-10-20a (45-mer): ccacctGGAGagagaccaagctttgatcggcacgta agaggttcc | 30 |
| | | | | cvd2015-10-20b (42-mer): cctttccggtctctTTTAgcttccttagctcctgaa aatctc | 31 |
| CV-141 (1029) | BsaI[TAAA]- PheS(T251A/ A294G)▶*- [CGCT]BsaI | PheS negative selection marker | Synthetic gene (Epoch Life Science, Inc.) | cvd1025-10-20c (39-mer): agggaaaggtctcaTAAAatgtcacatctcgcagaa ctg | 32 |
| | | | | cvd2015-11-03a (54-mer): tgcctggAGCGagagaccaagcttttattatttaaa ctgtttgaggaaacgcag | 33 |

TABLE 3

PCR primers used in the construction of the pML3 destination vector.
Spec$^R$ denotes spectinomycin resistance.

| PCR name (Size, bp) | | Fragment description | Template (source/ reference) | Primer name (length): Primer sequence (5' to 3') | SEQ ID NO. |
|---|---|---|---|---|---|
| CV-161 (1125) | BasI[ACCG]- P$_{aadA}$-Spec$^R$- [GAAT]BsaI | Bacterial spectinomycin resistance gene driven by the aadA promoter | pBB535 (41) | cvd2016-01-13a (41-mer): cgctcacggtctcaACCGgacgtcgatatccggatg aaggc | 34 |
| | | | | cvd2016-10-13b (45-mer): tgaacgaggtctcaATTCttatttgccgactaccTt ggtgatctc | 35 |
| CV-162 (591) | BsaI[GAAT]- f1ori- [GTGT]BsaI | Bacteriophage f1 origin of replication | pET -28a(+) (Novegen) | cvd2016-01-13c (55-mer): gatgagttggtctcaGAATtaattcatgagcggata catatttgaatgtatttag | 36 |
| | | | | cvd2015-11-18d (35-mer): gaggaacggtctccACACtggcgaatgggacgcgc | 37 |
| CV-79 (384) | BsaI[GTGT] [CATT]AarI- lacZα- AarI[CGTA] [GGCA]BsaI | Fragment containing the pML3 Golden Gate cloning cassette, i.e. lacZα (driven by the lac promoter) flanked by divergent AarI recognition sites. | E. coli K12 ER2925 (New England Biolabs) | cvd2015-05-22d (58-mer): actccagcggtctcaGTGTCVATTgcttgcaggtgt tattaccaggcaaagcgccattc | 38 |
| | | | | cvd2015-05-22j (55-mer): cgacaggggtctcgTGCCTACGgcgggcaggtggcg caacgcaattaatgtgagt | 39 |
| CV-152 (1070) | BsaI[BBCA]- pMB1 ori- [ACCG]BsaI | Bacterial pMB1 plasmid origin of replication. | pUC19 (Clontech Laboratories, Inc.) | cvd2015-11-18a (39-mer): cacattaaggtctctGGCAtcactgccgctttcca gtc | 40 |
| | | | | cvd2015-11-18b (50-mer): tgattaggtctcgCGGTctgtcagaccaagtttact catatatactttag | 41 |

TABLE 4 gBlock sequences used for the construction of the pML2 shuttle vectors.
gBlocks are synthesized as double stranded DNA;
only the top strand (5' to 3') is shown in the table.

| gBlock name | | gBlock sequence (5' to 3') | SEQ ID NO |
|---|---|---|---|
| "W" gBlocks | ML2(+)WF | gaccccgtaggtgtccatggcacctgcagctcattggagagagaccttaagcttgca gcagcggtctctcgctcattagagacggccggattgcggccgctaaccggccgtctc acgtaatatgcaggtgctcgagggcatcaaat | 2 |
| | ML2(+)WR | gaccccgtaggtgtccatggcacctgcagctcattagcgagagaccttaagcttgca gcagcggtctctctcccattagagacggccggattgcggccgctaaccggccgtctc acgtaatatgcaggtgctcgagggcatcaaat | 3 |
| | ML2(-)WF | gaccccgtaggtgtccatggcacctgcagctcattagagacggccggattgcggccg ctaaccggccgtctcacgtaggagagagaccttaagcttgcagcagcggtctctcgc tcgtaatatgcaggtgctcgagggcatcaaat | 4 |
| | ML2(-)WR | gaccccgtaggtgtccatggcacctgcagctcattagagacggccggattgcggccg ctaaccggccgtctcacgtaagcgagagaccttaagcttgcagcagcggtctctctc ccgtaatatgcaggtgctcgagggcatcaaat | 5 |
| "B" gBlocks | ML2(+)BF | gaccccgtaggtgtccatggcgtctcacattggagagagaccttaagcttgcagcag cggtctctcgctcattatatgcaggtggccggattgcggccgctaaccggccacctg cagctcgtaagagacgctcgagggcatcaaat | 6 |
| | ML2(+)BR | gaccccgtaggtgtccatggcgtctcacattagcgagagaccttaagcttgcagcag cggtctctctcccattatatgcaggtggccggattgcggccgctaaccggccacctg cagctcgtaagagacgctcgagggcatcaaat | 7 |
| | ML2(-)BF | gaccccgtaggtgtccatggcgtctcacattatatgcaggtggccggattgcggccg ctaaccggccacctgcagctcgtaggagagagaccttaagcttgcagcagcggtctc tcgctcgtaagagacgctcgagggcatcaaat | 8 |
| | ML2(-)BR | gaccccgtaggtgtccatggcgtctcacattatatgcaggtggccggattgcggccg ctaaccggccacctgcagctcgtaagcgagagaccttaagcttgcagcagcggtctc tctcccgtaagagacgctcgagggcatcaaat | 9 |

TABLE 5

Generalised guidelines for the design of primers for amplification of ProUTR, CDS and UTRterm modules to be cloned into pML1. Generalized features of forward and reverse PCR primers used for amplification of ProUTR, CDS and UTRterm TUMs are listed. The 5' and 3' nucleotide-specific bases, which flank each TUM and form the basis of the address system for each of the MIDAS modules, are shown in bold.

| gBlock name | | gBlock sequence (5' to 3') | SEQ ID NO |
|---|---|---|---|
| "W" gBlocks | ML2(+)WF | gaccccgtaggtgtccatggcacctgcagctcattggagagagaccttaagcttgca gcagcggtctctcgctcattagagacggccggattgcggccgctaaccggccgtctc acgtaatatgcaggtgctcgagggcatcaaat | 2 |
| | ML2(+)WR | gaccccgtaggtgtccatggcacctgcagctcattagcgagagaccttaagcttgca gcagcggtctctctcccattagagacggccggattgcggccgctaaccggccgtctc acgtaatatgcaggtgctcgagggcatcaaat | 3 |
| | ML2(-)WF | gaccccgtaggtgtccatggcacctgcagctcattagagacggccggattgcggccg ctaaccggccgtctcacgtaggagagagaccttaagcttgcagcagcggtctctcgc tcgtaatatgcaggtgctcgagggcatcaaat | 4 |
| | ML2(-)WR | gaccccgtaggtgtccatggcacctgcagctcattagagacggccggattgcggccg ctaaccggccgtctcacgtaagcgagagaccttaagcttgcagcagcggtctctctc ccgtaatatgcaggtgctcgagggcatcaaat | 5 |
| "B" gBlocks | ML2(+)BF | gaccccgtaggtgtccatggcgtctcacattggagagagaccttaagcttgcagcag cggtctctcgctcattatatgcaggtggccggattgcggccgctaaccggccacctg cagctcgtaagagacgctcgagggcatcaaat | 6 |
| | ML2(+)BR | gaccccgtaggtgtccatggcgtctcacattagcgagagaccttaagcttgcagcag cggtctctctcccattatatgcaggtggccggattgcggccgctaaccggccacctg cagctcgtaagagacgctcgagggcatcaaat | 7 |
| | ML2(-)BF | gaccccgtaggtgtccatggcgtctcacattatatgcaggtggccggattgcggccg ctaaccggccacctgcagctcgtaggagagagaccttaagcttgcagcagcggtctc tcgctcgtaagagacgctcgagggcatcaaat | 8 |
| | ML2(-)BR | gaccccgtaggtgtccatggcgtctcacattatatgcaggtggccggattgcggccg ctaaccggccacctgcagctcgtaagcgagagaccttaagcttgcagcagcggtctc tctcccgtaagagacgctcgagggcatcaaat | 9 |

TABLE 6

Level-3 multigene assemblies are constructed by alternating Golden Gate cloning reactions using TUs assembled in "W" and "B" pML2 vectors. The table shows the cloning steps used to produce a hypothetical multigene construct containing four TUs, with each row depicting the input plasmids (Level-2 entry clone and destination plasmid), the type of Golden Gate reaction used for assembly, the product plasmid and the type of colonies screened.

| Step | Level-2 entry clone | Destination plasmid | Golden Gate reaction | Product plasmid | Screen |
|---|---|---|---|---|---|
| 1 | TU1 in a "W" pML2 vector | pML3 | AarI-mediated | pML3:TU1 | White colonies |
| 2 | TU2 in a "B" pML2 vector | pML3:TU1 | BsmBI-mediated | pML3:TU1:TU2 | Blue colonies |
| 3 | TU3 in a "W" pML2 vector | pML3:TU1:TU2 | AarI-mediated | pML3:TU1:TU2:TU3 | White colonies |
| 4 | TU4 in a "B" pML2 vector | pML3:TU1:TU2:TU3 | BsmBI-mediated | pML3:TU1:TU2:TU3:TU4 | Blue colonies |

TABLE 7

PCR primers for amplification of transcription unit modules (TUMs). The forward and reverse PCR primers used for amplification of pax gene TUMs and TUMs from other genes used in this study are listed. The names of the primers used to amplify TUM fragments for domestication purposes (i.e. removal of internal sites for AarI, BsaI or BsmBI) are shaded grey. The template for amplification of pax gene TUMs was genomic DNA from *Penicillium paxilli* strain ATCC26601 (PN2013) [Accession HM171111]. The PCR products used to produce the trpC ProUTR module, nptII CDS module (conferring resistance to geneticin), and trpC$_{UTRterm}$ module were all amplified from plasmid pII99 (42). The 5' and 3' nucleotide-specific bases, which flank each TUM and form the basis of the address system for each of the MIDAS modules, are shown in bold.

| TUM | Primer name | Primer Sequence (5' to 3') | SEQ ID NO. |
|---|---|---|---|
| paxG$_{ProUTR}$ | P paxG F | cgatgtacgtctcaCTCGGGAGattcacgacctgtgactagtcaa | 48 |
|  | P paxG R | gacctttcgtctctGTCTcaCATTgcgtcgaacttgatgaagttttct | 49 |
| paxG$_{CDS}$ | paxG frag1 F | cgatgtacgtctcaCTCGAATGtcctacatccttgcagaag | 50 |
|  | paxG frag1 R | cttctacgtctcgTACTgttctaatcgtgcttggtg | 51 |
|  | paxG frag2 F | gcacgacgtctccAGTAcaggtgctagaagatgacgttgac | 52 |
|  | paxG frag2 R | aggcgccgtctccACCAatctctttcaatcttgcttgttgga | 53 |
|  | paxG frag3 F | gattgacgtctctTGGTgaccccgcgcctt | 54 |
|  | paxG frag3 R | gtcgaccgtctctTTCCctagtatattggaagctccccg | 55 |
|  | paxG frag4 F | tccaatcgtctcgGGAAaccctaagtcgacttagtgcg | 56 |
|  | paxG frag4 R | gacctttcgtctctGTCTcaAAGCttaaactcttcctttctcattagtaggg | 57 |
| paxG$_{UTRterm}$ | T paxG F | cgatgtacgtctcacCTCGGCTTtcaatcgtgctgcatttctctt | 58 |
|  | T paxG R | gacctttcgtctctGTCTcaAGCGtcactcccgagcaatattgct | 59 |
| paxM$_{ProUTR}$ | P paxM F | cgatgtacgtctcaCTCGGGAGgttgttggcatgggagtaggat | 60 |
|  | p paxM R | gacctttcgtctctGTCTcaCATTgtttctgaatcttaaagatacatgaaaagaataaagc | 61 |
| paxM$_{CDS}$ | paxM frag1 F | cgatgtacgtctcaCTCGAATGgaaaaggccgagtttcaag | 62 |
|  | paxM frag1 R | tgacaacgtctcgTCCAtcgaataaagcgttgacttgc | 63 |
|  | paxM frag2 F | acgcttcgtctcaTGGActcactattgtcacaatccatggaaaag | 64 |
|  | paxM frag2 R | gacctttcgtctctGTCTcaAAGCttaaacttgaagaaaataaaacttcagggcac | 65 |
| paxM$_{UTRterm}$ | T paxM frag1 F | cgatgtacgtctcaCTCGGCTTaccattggagcaattttggttttc | 66 |
|  | T paxM frag1 R | gttcgccgtctcgACTCgattgcttgtgggtct | 67 |
|  | T paxM frag2 F | acaagccgtctccGAGTccagccagcgaacttg | 68 |
|  | T paxM frag2 R | gacctttcgtctctGTCTcaAGCGTttggcttacttcagtttaactgttTTG | 69 |
| paxB$_{ProUTR}$ | P paxB F | cgatgtacgtctcaCTCGGGAGaaggctgtgttggagagaatc | 70 |
|  | P paxB R | gacctttcgtctctGTCTcaCATTgtttctaaggttgacgtgggaaaaag | 71 |
| paxB$_{CDS}$ | paxB F | cgatgtacgtctcaCTCGAATGgacggttttgatgtttcccaa | 72 |
|  | paxB R | gacctttcgtctctGTCTcaAAGCtcaatttgctttttttcggcccgcttatgc | 73 |
| paxB$_{UTRterm}$ | T paxB F | cgatgtacgtctcaCTCGGCTTtcggcagttgagggtgaaac | 74 |
|  | T paxB R | gacctttcgtctctGTCTcaAGCGggttaacaatgaggaacgatgaacag | 75 |
| paxC$_{ProUTR}$ | P paxC F | cgatgtacgtctcaCTCGGGAGacaacaaaaagatcagccaatgg | 76 |
|  | P paxC R | gacctttcgtctctGTCTcaCATTaaaatggggacctacaccctgaa | 77 |
| paxC$_{CDS}$ | paxC frag1 F | cgatgtacgtctcaCTCGAATGggcgtagcaggga | 78 |
|  | paxC frag1 R | cattgacgtctccACGGcgccagacaaggga | 79 |
|  | paxC frag2 F | cccttgcgtctcgCCGTgacggagtcaatgggttc | 80 |
|  | paxC frag2 R | gacctttcgtctctGTCTcaAAGCtcatgccttcaggtcaagcttc | 81 |
| paxC$_{UTRterm}$ | T paxC F | cgatgtacgtctcaCTCGGCTTtggccttgtgaaatatgggactac | 82 |
|  | T paxC R | gacctttcgtctctGTCTcaAGCGatctctgtcatgtcggatatcagat | 83 |

TABLE 7-continued

PCR primers for amplification of transcription unit modules (TUMs). The forward and reverse PCR primers used for amplification of pax gene TUMs and TUMs from other genes used in this study are listed. The names of the primers used to amplify TUM fragments for domestication purposes (i.e. removal of internal sites for AarI, BsaI or BsmBI) are shaded grey. The template for amplification of pax gene TUMs was genomic DNA from Penicillium paxilli strain ATCC26601 (PN2013) [Accession HM171111]. The PCR products used to produce the trpC ProUTR module, nptII CDS module (conferring resistance to geneticin), and trpC$_{UTRterm}$ module were all amplified from plasmid pII99 (42). The 5' and 3' nucleotide-specific bases, which flank each TUM and form the basis of the address system for each of the MIDAS modules, are shown in bold.

| TUM | Primer name | Primer Sequence (5' to 3') | SEQ ID NO. |
|---|---|---|---|
| paxP$_{ProUTR}$ | P paxP F | cgatgtacgtctcaCTCGGGAGagggaaatttggaaatagattacactcga | 84 |
|  | P paxP R | gacctttcgtctctGTCTcaCATTttctttaggtagttttagttaaatcgaggaaagaga | 85 |
| paxP$_{CDS}$ | paxP frag1 F | cgatgtacgtctcaCTCGAATGgatctatccgatttccacatctc | 86 |
|  | paxP frag1 R | ggatagcgtctcaCTCTgtctcaaacttgaagtcatag | 87 |
|  | paxP frag2 F | gctttacgtctcaAGAGcacaaggaaagaccgaagaatct | 88 |
|  | paxP frag2 R | gacctttcgtctctGTCTcaAAGCttacgcctttgtagcccgac | 89 |
| paxP$_{UTRterm}$ | T paxP F | cgatgtacgtctcaCTCGGCTTatagggatacgttgccggtc | 90 |
|  | T paxP R | gacctttcgtctctGTCTcaAGCGgagcatggattacaattttgcgag | 91 |
| paxQ$_{ProUTR}$ | P paxQ F | cgatgtacgtctcaCTCGGGAGtctctaggatagatctggcctttggt | 92 |
|  | P paxQ R | gacctttcgtctctGTCTcaCATTcttgcgatagattctaacgaagg | 93 |
| paxQ$_{CDS}$ | paxQ frag1 F | cgatgtacgtctcaCTCGAATGgatttcgtgttatcagccttac | 94 |
|  | paxQ frag1 R | gcattgcgtctcaAGAGcgatgaaggagtgcag | 95 |
|  | paxQ frag2 F | gcacttcgtctcaCTCTcgaaagttgcaggtaattaactg | 96 |
|  | paxQ frag2 R | gcatgacgtctcaACCTgtctcaaagcaaggcagctc | 97 |
|  | paxQ frag3 F | cgtcatcgtctcaAGGTgcaagagttgtcgcac | 98 |
|  | paxQ frag3 R | gcatgacgtctcaAGGCctcgtcgctagctcaaataaac | 99 |
|  | paxQ frag4 F | gcacttcgtctcaGCCTgagtatgtcgagcctctg | 100 |
|  | paxQ frag4 R | gacctttcgtctctGTCTcaAAGCtcatgccgagacagactttctg | 101 |
| paxQ$_{UTRterm}$ | T paxQ F | cgatgtacgtctcaCTCGGCTTagggaaatttggaaatagattacactc | 102 |
|  | T paxQ R | gacctttcgtctctGTCTcaAGCGtctagtttcaaattcgctgggttg | 103 |
| trpC$_{ProUTR}$ | P trpC frag1 F | cgatgtacgtctcaCTCGGGAGgaattcatgccagttgttcccag | 104 |
|  | P trpC frag1 R | cgatgtacgtctcaGCTTggccgactcgctg | 105 |
|  | P trpC frag2 F | cacctttcgtctccAAGCagacgtgaagcaggacgg | 106 |
|  | P trpC frag2 R | cgatgtcgtctcgCAGAccattgcacaagcctc | 107 |
|  | P trpC frag3 F | gacctttcgtctcgTCTGcgcatggatcgctgc | 108 |
|  | P trpC frag3 R | gacctttcgtctctGTCTcaCATTtcgatgcttgggtagaataggtaag | 109 |
| trpC$_{UTRterm}$ | T trpC frag1 F | cgatgtacgtctcaCTCGGCTTgatccacttaacgttactgaaatcatcaaac | 110 |
|  | T trpC frag1 R | gacctttcgtctctCTGCttgatctcgtctgccga | 111 |
|  | T trpC frag2 F | cgatgtacgtctcaGCAGatcaacggtcgtcaacagacc | 112 |
|  | T trpC frag2 R | gacctttcgtctctGTCTcaAGCGtctagaaagaaggattacctctaaacaagtgt | 113 |
| nptII$_{CDS}$ | nptII F | cgatgtacgtctcaCTCGAATGattgaacaagatggattgcacg | 114 |
|  | nptII R | gacctttcgtctctGTCTcaAAGCctcagaagaactcgtcaagaaggc | 115 |

TABLE 8

Cloning TUMs into pML1. The ratio of white to blue colonies represents the total number of each type of colony obtained per Golden Gate reaction, extrapolated from the numbers of colonies obtained per plate. The columns labelled "Correct by restriction pattern" and "Correct by sequencing" show, respectively, the fraction of analysed clones that were correct as determined by either restriction enzyme analysis or by sequencing of the BsmBI assembly junctions.

| UM class | TUM | Plasmid name | Number of PCR fragments required to assemble the TUM in pML1 | Ratio white:blue | % white | Correct by restriction pattern | Correct by sequencing |
|---|---|---|---|---|---|---|---|
| ProUTR | paxG$_{ProUTR}$ | pSK1 | 1 | 8640:853 | 91.0 | 2/2 | 2/2 |
|  | paxM$_{ProUTR}$ | pSK4 | 1 | 7947:533 | 93.7 | 2/2 | 1/1 |
|  | paxB$_{ProUTR}$ | pSK7 | 1 | 9653:480 | 95.3 | 2/2 | 1/1 |
|  | paxC$_{ProUTR}$ | pKV28 | 1 | 5227:320 | 94.2 | 2/2 | 1/1 |
|  | paxP$_{ProUTR}$ | pSK75 | 1 | 10507:213 | 98.0 | 2/2 | 1/1 |
|  | paxQ$_{ProUTR}$ | pSK76 | 1 | 14240:427 | 97.1 | 2/2 | 1/1 |
|  | trpC$_{ProUTR}$ | pSK17 | 3 | 2027:453 | 81.7 | 2/2 | 2/2 |

TABLE 8-continued

Cloning TUMs into pML1. The ratio of white to blue colonies represents the total number of each type of colony obtained per Golden Gate reaction, extrapolated from the numbers of colonies obtained per plate. The columns labelled "Correct by restriction pattern" and "Correct by sequencing" show, respectively, the fraction of analysed clones that were correct as determined by either restriction enzyme analysis or by sequencing of the BsmBI assembly junctions.

| UM class | TUM | Plasmid name | Number of PCR fragments required to assemble the TUM in pML1 | Ratio white:blue | % white | Correct by restriction pattern | Correct by sequencing |
|---|---|---|---|---|---|---|---|
| CDS | $paxG_{CDS}$ | pSK2 | 4 | 1947:507 | 79.3 | 2/2 | 2/2 |
| | $paxM_{CDS}$ | pSK5 | 2 | 3840:1173 | 76.6 | 2/2 | 2/2 |
| | $paxB_{CDS}$ | pSK8 | 1 | 4747:587 | 89.0 | 2/2 | 1/1 |
| | $paxC_{CDS}$ | pSK11 | 2 | 4373:1280 | 77.4 | 2/2 | 1/1 |
| | $paxP_{CDS}$ | pSK69 | 2 | 8267:480 | 94.5 | 2/2 | 1/1 |
| | $paxQ_{CDS}$ | pSK71 | 4 | 1520:160 | 90.5 | 2/2 | 1/1 |
| | $nptII_{CDS}$ | pSK16 | 1 | 4800:747 | 86.5 | 2/2 | 2/2 |
| UTRterm | $paxG_{UTRterm}$ | pSK3 | 1 | 6667:427 | 94.0 | 2/2 | 1/1 |
| | $paxM_{UTRterm}$ | pSK6 | 2 | 5973:587 | 91.1 | 2/2 | 2/2 |
| | $paxB_{UTRterm}$ | pSK9 | 1 | 7093:693 | 91.1 | 2/2 | 2/2 |
| | $paxC_{UTRterm}$ | pSK12 | 1 | 9653:1387 | 87.4 | 2/2 | 1/1 |
| | $paxP_{UTRterm}$ | pSK70 | 1 | 12587:213 | 98.3 | 2/2 | 1/1 |
| | $paxQ_{UTRterm}$ | pSK72 | 1 | 13172:373 | 97.2 | 2/2 | 1/1 |
| | $trpC_{UTRterm}$ | pSK15 | 2 | 5120:373 | 93.2 | 2/2 | 1/1 |

TABLE 9

Level-1 TUM libraries in pML1. This table represents the information from Table 8 in a form that shows the cloned TUMs categorised into libraries, and shows the 4 nucleotide addresses flanking each TUM.

| [GGAG] | | [AATG] | | [GCTT] | | [CGCT] | |
|---|---|---|---|---|---|---|---|
| ProUTR modules | | CDS modules | | UTRterm modules | | | |
| Plasmid name | Description | Plasmid name | Description | Plasmid name | Description | Plasmid name | Description |
| pSK1 | $paxG_{ProUTR}$ | pSK2 | $paxG_{CDS}$ | pSK3 | $paxG_{UTRterm}$ | pSK75 | $paxP_{ProUTR}$ |
| pSK4 | $paxM_{ProUTR}$ | pSK5 | $paxM_{CDS}$ | pSK6 | $paxM_{UTRterm}$ | pSK76 | $paxQ_{ProUTR}$ |
| pSK7 | $paxB_{ProUTR}$ | pSK8 | $paxB_{CDS}$ | pSK9 | $paxB_{UTRterm}$ | pSK17 | $trpC_{ProUTR}$ |
| pKV28 | $paxC_{ProUTR}$ | pSK11 | $paxC_{CDS}$ | pSK12 | $paxC_{UTRterm}$ | | |

(continued)

| ProUTR modules | | CDS modules | | UTRterm modules | |
|---|---|---|---|---|---|
| Plasmid name | Description | Plasmid name | Description | Plasmid name | Description |
| pSK75 | $paxP_{ProUTR}$ | pSK69 | $paxP_{CDS}$ | pSK70 | $paxP_{UTRterm}$ |
| pSK76 | $paxQ_{ProUTR}$ | pSK71 | $paxQ_{CDS}$ | pSK72 | $paxQ_{UTRterm}$ |
| pSK17 | $trpC_{ProUTR}$ | pSK16 | $nptII_{CDS}$ | pSK15 | $trpC_{UTRterm}$ |

TABLE 10

Assembly of TUs in pML2 shuttle vectors. The table shows the Level-1 entry clones and pML2 shuttle vectors used to assemble TUs. The names of the Level-2 entry plasmids produced are shown in the grey shaded column. TUs assembled using the native promoters and terminators are annotated using the name of the CDS they contain; in all other cases, the promoter-CDS-terminator structure of the TU is elaborated. TU orientation is shown by the arrowhead. The column labelled "$Kan^R$ cfus" represents the total number of kanamycin resistant colonies obtained per Golden Gate reaction, extrapolated from the number of colonies obtained per plate. The columns labelled "Correct by restriction pattern" and "Correct by sequencing" show, respectively, the fraction of analysed clones that were correct as determined by either restriction enzyme analysis or by sequencing of the BsaI assembly junctions.

| | Level-1 entry clones used for TU assembly | | | pML2 shuttle vector | Level-2 entry clones | | $Kan^R$ cfus | Correct by restriction pattern | Correct by sequencing |
|---|---|---|---|---|---|---|---|---|---|
| TU | ProUTR | CDS | UTRterm | | Name | Description | | | |
| paxG | pSK1 | pSK2 | pSK3 | pML2(+)BR | pSK21 | ◄paxG:pML2(+)BR | 3720 | 2/2 | 1/1 |
| | pSK7 | pSK2 | pSK3 | pML2(+)BR | pSK47 | ◄($T_{paxG}$-paxG-$P_{paxB}$):pML2(+)BR | 3880 | 2/2 | 1/1 |
| paxM | pSK4 | pSK5 | pSK6 | pML2(+)WR | pSK22 | ◄paxM:pML2(+)WR | 3680 | 2/2 | 1/1 |
| | | | | pML2(+)BR | pRB1 | ◄paxM:pML2(+)BR | 5040 | 2/2 | 1/1 |
| paxB | pSK7 | pSK8 | pSK9 | pML2(+)BR | pSK23 | ◄paxB:pML2(+)BR | 9400 | 2/2 | 1/1 |
| paxC | pKV28 | pSK11 | pSK12 | pML2(+)BF | pKV29 | paxC►:pML2(+)BF | 7360 | 2/2 | 1/1 |
| | pKV28 | pSK11 | pSK12 | pML2(+)WF | pSK59 | paxC►:pML2(+)WF | 4880 | 2/2 | 1/1 |
| | pSK17 | pSK11 | pSK15 | pML2(+)WF | pSK61 | ($P_{trpC}$-paxC-$T_{trpC}$)►:pML2(+)WF | 9840 | 2/2 | 1/1 |
| paxP | pSK75 | pSK69 | pSK70 | pML2(+)BR | pSK73 | ◄paxP:pML2(+)BR | 9400 | 1/2 | 1/1 |
| paxQ | pSK76 | pSK71 | pSK72 | pML2(+)WR | pSK74 | ◄paxQ:pML2(+)WR | 11200 | 2/2 | 1/1 |
| nptII | pSK17 | pSK16 | pSK15 | pML2(+)WF | pSK26 | ($P_{trpC}$-nptII-$T_{trpC}$)►:pML2(+)WF | 5440 | 2/2 | 1/1 |

TABLE 11

Multigene assemblies. The table shows the Level-2 entry clones and Level-3 destination vectors used to construct the multigene plasmids. The names of the plasmids produced during each cycle of Level-3 assembly are shown in the grey shaded column. TUs are annotated with the name of the CDS they contain. TU orientation is shown by the arrowhead.

| Step | Level-2 entry clone Name | Description | Destination vector | Golden Gate reaction | Product Level-3 plasmid Name | Description | Plasmid size (kb) |
|---|---|---|---|---|---|---|---|
| 1 | pSK26 | (P$_{trpC}$-nptII-T$_{trpC}$)▶ :pML2(+)WF | pML3 | AarI | pSK33 | pML3:nptII▶ | 5.6 |
| 2 | pSK21 | ◀paxG:pML2(+)BR | pSK33 | BsmBI | pSK34 | pML3:nptII▶ : ◀paxG | 8.2 |
| 3 | pSK22 | ◀paxM:pML2(+)WR | pSK34 | AarI | pSK36 | pML3:nptII▶ : ◀paxG: ◀paxM | 11.5 |
| 4 | pSK23 | ◀paxB:pML2(+)BR | pSK36 | BsmBI | pSK37 | pML3:nptII▶ : ◀paxG: ◀paxM: ◀paxB | 14.1 |
| 5 | pSK59 | paxC▶ :pML2(+)WF | pSK37 | AarI | pSK64 | pML3:nptII▶ : ◀paxG: ◀paxM: ◀paxBpaxC▶ | 16.3 |
| 5 | pSK61 | (P$_{trpC}$-paxC-T$_{trpC}$)▶ :pML2(+)WF | pSK37 | AarI | pSK63 | pML3:nptII▶ : ◀paxG: ◀paxM: ◀paxBpaxC▶ | 16.9 |
| 6 | pSK73 | ◀paxP:pML2(+)BR | pSK64 | BsmBI | pSK78 | pML3:nptII▶ : ◀paxG: ◀paxM: ◀paxB: paxC▶ : ◀paxP | 21.1 |
| 7 | pSK74 | ◀paxQ:pML2(+)WR | pSK78 | AarI | pSK79 | pML3:nptII▶ : ◀paxG: ◀paxM: ◀paxB: paxC▶ : ◀paxP: ◀paxQ | 25.2 |
| 2 | pRB1 | ◀paxM:pML2(+)BR | pSK33 | BsmBI | pRB3 | pML3:nptII▶ : ◀paxM | 9.4 |
| 2 | pKV29 | paxC▶ :pML2(+)BF | pSK33 | BsmBI | pKV30 | pML3:nptII▶ :paxC▶ | 8.4 |
| 2 | pSK47 | ◀(T$_{paxG}$-paxG-P$_{paxB}$):pML2(+)BR | pSK33 | BsmBI | pSK52 | pML3:nptII▶ : ◀paxG | 8.7 |

TABLE 12

Multigene assembly data. The table presents the efficiencies of assembly of the multigene plasmids shown in Table 11. The first four columns are reproduced from Table 11. BsmBI-mediated assemblies were performed in T4 DNA Ligase buffer, as per conventional Golden Gate reactions. AarI-mediated assembly reactions were performed in either T4 DNA Ligase buffer, or in AarI restriction enzyme buffer supplemented with ATP. The ratio of white to blue colonies represents the total number of each type of colony obtained per Golden Gate reaction, extrapolated from the numbers of colonies obtained per plate, with the column labelled "Colony type (%)" showing the proportion (%) of colonies of the desired colour that were obtained from each Golden Gate reaction. The column labelled "Correct" shows the fraction of analysed clones that were correct as determined by restriction enzyme analysis.

| Golden Gate reaction | Product Level-3 lasmid Name | Description | Plasmid size (kb) | Assembly reaction performed in ligase buffer | | Assembly reaction performed in restriction enzyme buffer + ATP | | Correct |
|---|---|---|---|---|---|---|---|---|
| | | | | Ratio White:blue | Colony type (%) | Ratio White:blue | Colony type (%) | |
| AarI | pSK33 | pML3:nptII▶ | 5.6 | 68800:21760 | White (76) | 94667:533 | White (99.4) | 2/2 |
| BsmBI | pSK34 | pML3:nptII▶ : ◀paxG | 8.2 | 0:89600 | Blue (100) | — | — | 2/2 |
| AarI | pSK36 | pML3:nptII▶ : ◀paxG: ◀paxM | 11.5 | 31680:8960 | White (78) | 74133:2933 | White (96.2) | 2/2 |
| BsmBI | pSK37 | pML3:nptII▶ : ◀paxG: ◀paxM: ◀paxB | 14.1 | 533:83200 | Blue (99.4) | — | — | 2/2 |
| AarI | pSK64 | pML3:nptII▶ : ◀paxG: ◀paxM: ◀paxB:paxC▶ | 16.3 | 20640:800 | White (96.3) | 86400:267 | White (99.7) | 2/2 |
| AarI | pSK63 | pML3:nptII▶ : ◀paxG: ◀paxM: ◀paxB:paxC▶ | 16.9 | 17600:640 | White (96.5) | 72800:267 | White (99.6) | 1/2 |
| BsmBI | pSK78 | pML3:nptII▶ : ◀paxG: ◀paxM: ◀paxB: paxC▶ : ◀paxP | 21.1 | 0:32267 | Blue (100) | — | — | 2/2 |
| AarI | pSK79 | pML3:nptII▶ : ◀paxG: ◀paxM: ◀paxB: paxC▶ : ◀paxP: ◀paxQ | 25.2 | 3760:2120 | White (64) | 29067:267 | White (99.1) | 2/2 |
| BsmBI | pRB3 | pML3:nptII▶ : ◀paxM | 9.4 | 533:92267 | Blue (99.4) | — | — | 2/2 |
| BsmBI | pKV30 | pML3:nptII▶ :paxC▶ | 8.4 | 267:78400 | Blue (99.7) | — | — | 2/2 |
| BsmBI | pSK52 | pML3:nptII▶ : ◀paxG | 8.7 | 267:70667 | Blue (99.6) | — | — | 2/2 |

TABLE 13

Multistep acetonitrile gradient used for LC-MS analysis of fungal extracts.

| Time (minutes) | % (v/v) of acetonitrile + 0.01% (v/v) formic acid |
|---|---|
| 0 | 50 |
| 1 | 50 |
| 15 | 70 |
| 20 | 95 |
| 25 | 95 |
| 28 | 50 |
| 38 | 50 |

TABLE 14

$^1$H and $^{13}$C NMR data of paspaline and paxilline recorded in CDCl$_3$.

| Position | Paspaline $^1$H | Paspaline $^{13}$C | Paxilline $^1$H | Paxilline $^{13}$C |
|---|---|---|---|---|
| 1 | — | — | — | — |
| 2 | 3.1 | 85 | 3.7 | 83 |
| 3 | 1.7, 1.4 | 21 | — | 198 |
| 4 | 1.3, 1.3 | 37 | 5.8 | 119 |
| 4a | — | 36 | — | 170 |
| 4a-Me | | | | |
| 4b | 1.4 | 46 | — | 76 |
| 5 | 1.6, 1.3 | 21 | 1.7, 1.8 | 33 |
| 6 | 1.8, 1.5 | 25 | 1.6, 1.8 | 21 |
| 6a | 2.7 | 49 | 2.7 | 49 |
| 7 | 2.5, 2.6 | 29 | 2.6, 1.9 | 27 |
| 7a | — | 116 | — | 115 |
| 7b | — | 125 | — | 125 |
| 8 | 7.2 | 118 | 7.3 | 118 |
| 9 | 6.9 | 119 | 6.9 | 119 |
| 10 | 6.9 | 119 | 6.9 | 119 |
| 11 | 7.3 | 112 | 7.3 | 112 |
| 11a | — | 140 | — | 140 |
| 12 | — | — | — | — |
| 12a | — | 151 | — | 153 |
| 12b | — | 53 | — | 50 |
| 12b-Me | | | | |
| 12c | — | 39 | — | 43 |
| 12c-Me | | | | |
| 13 | 1.6, 1.9 | 31 | 1.9, 1.9 | 26 |
| 14 | 1.8, 1.7 | 25 | 2.6, 1.7 | 28 |
| 14a | 2.9 | 85 | 4.8 | 73 |
| 1' | — | 71 | — | 71 |
| 2' | 1 | 27 | 1.2 | 26 |
| 3' | 1.1 | 29 | 1.2 | 26 |

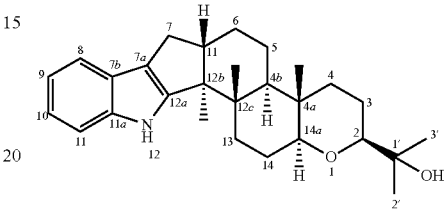

paspaline
C$_{28}$H$_{39}$NO$_2$
Exact Mass: 421.30
calc. [M + H]+ 422.3054 m/z
obs. [M + H]+ 422.3055 m/z

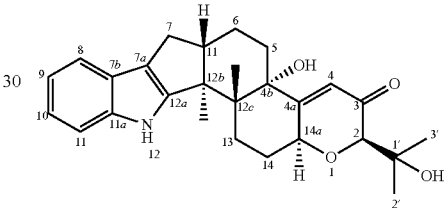

paxilline
C$_{27}$H$_{33}$NO$_4$
Exact Mass: 435.24
calc. [M + H]+ 436.2482 m/z
obs. [M + H]+ 436.2485 m/z

TABLE 15

*Penicillium paxilli* strains. Hyg$^R$ and Gen$^R$ denote hygromycin and geneticin resistance, respectively.

| *Penicillium paxilli* strain | Description | Indole diterpene phenotype Paspaline | Indole diterpene phenotype Paxilline | Source (reference) |
|---|---|---|---|---|
| PN2013 (=ATCC26601) | Wild type | + | + | Barry Scott, Massey University (43) |
| PN2250 (CY2) | PN2013/Deletion of entire PAX locus (ΔPAX); Hyg$^R$ | − | − | Barry Scott, Massey University (44) |
| PN2257 | PN2013/ΔpaxM::P$_{glcA}$-hph-T$_{trpC}$; Hyg$^R$ | − | − | Barry Scott, Massey University (33) |

INDUSTRIAL APPLICATION

The vector sets and methods of the invention have industrial application in molecular biology in providing a means to manipulate polynucleotide sequences to form in vitro and heterologous in vivo expression systems for the production of various biochemical molecules.

REFERENCES

1. D. L. Cheo et al., Concerted assembly and cloning of multiple DNA segments using in vitro site-specific recombination: functional analysis of multi-segment expression clones. *Genome research* 14, 2111-2120 (2004).
2. A. Kriz et al., A plasmid-based multigene expression system for mammalian cells. *Nature communications* 1, 120 (2010).
3. C. Bieniossek et al., Automated unrestricted multigene recombineering for multiprotein complex production. *Nature methods* 6, 447-450 (2009).
4. Q. J. Chen et al., MISSA is a highly efficient in vivo DNA assembly method for plant multiple-gene transformation. *Plant physiology* 153, 41-51 (2010).
5. B. S. Moriarity et al., Modular assembly of transposon integratable multigene vectors using RecWay assembly. *Nucleic Acids Res* 41, e92 (2013).
6. R. M. Horton, H. D. Hunt, S. N. Ho, 3. K. Pullen, L. R. Pease, Engineering Hybrid Genes without the Use of Restriction Enzymes—Gene-Splicing by Overlap Extension. *Gene* 77, 61-68 (1989).
7. D. G. Gibson et al., Enzymatic assembly of DNA molecules up to several hundred kilobases. *Nat Methods* 6, 343-345 (2009).
8. In-Fusion HD Cloning Kit User Manual. *Clontech Laboratories, Inc.*, (2014).
9. B. G. Zhu, G. F. Cai, E. O. Hall, G. J. Freeman, In-Fusion™ assembly: seamless engineering of multidomain fusion proteins, modular vectors, and mutations. *BioTechniques* 43, 356-359 (2007).
10. A. Rashtchian, G. W. Buchman, D. M. Schuster, M. S. Berninger, Uracil DNA Glycosylase-Mediated Cloning of Polymerase Chain Reaction-Amplified DNA—Application to Genomic and Cdna Cloning. *Anal Biochem* 206, 91-97 (1992).
11. C. Aslanidis, P. J. Dejong, Ligation-Independent Cloning of Pcr Products (Lic-Pcr). *Nucleic Acids Res* 18, 6069-6074 (1990).
12. J. Garcia-Nafria, J. F. Watson, I. H. Greger, IVA cloning: A single-tube universal cloning system exploiting bacterial In Vivo Assembly. *Scientific reports* 6, 27459 (2016).
13. K. Tsuge, K. Matsui, M. Itaya, One step assembly of multiple DNA fragments with a designed order and orientation in *Bacillus subtilis* plasmid. *Nucleic Acids Res* 31, e133 (2003).
14. M. Itaya, K. Fujita, A. Kuroki, K. Tsuge, Bottom-up genome assembly using the *Bacillus subtilis* genome vector. *Nature methods* 5, 41-43 (2008).
15. Z. Y. Shao, H. Zhao, H. M. Zhao, DNA assembler, an in vivo genetic method for rapid construction of biochemical pathways. *Nucleic Acids Res* 37, (2009).
16. H. Ma, S. Kunes, P. J. Schatz, D. Botstein, Plasmid Construction by Homologous Recombination in Yeast. *Gene* 58, 201-216 (1987).
17. D. G. Gibson et al., One-step assembly in yeast of 25 overlapping DNA fragments to form a complete synthetic *Mycoplasma genitalium* genome. *Proceedings of the National Academy of Sciences of the United States of America* 105, 20404-20409 (2008).
18. V. Larionov, N. Kouprina, J. Graves, M. A. Resnick, Highly selective isolation of human DNAs from rodent-human hybrid cells as circular yeast artificial chromosomes by transformation-associated recombination cloning. *Proceedings of the National Academy of Sciences of the United States of America* 93, 13925-13930 (1996).
19. I. J. W. M. Goderis et al., A set of modular plant transformation vectors allowing flexible insertion of up to six expression units. *Plant Mol Biol* 50, 17-27 (2002).
20. H. Ghareeb, S. Laukamm, V. Lipka, COLORFUL-Circuit: A Platform for Rapid Multigene Assembly, Delivery, and Expression in Plants. *Frontiers in plant science* 7, 246 (2016).
21. G. J. Cost, N. R. Cozzarelli, Directed assembly of DNA molecules via simultaneous ligation and digestion. *Biotechniques* 42, 84-89 (2007).
22. T. F. Knight, Idempotent Vector Design for Standard Assembly of Biobricks. 2003.
23. C. Engler, R. Kandzia, S. Marillonnet, A One Pot, One Step, Precision Cloning Method with High Throughput Capability. *Plos One* 3, (2008).
24. A. Sarrion-Perdigones et al., GoldenBraid: An Iterative Cloning System for Standardized Assembly of Reusable Genetic Modules. *Plos One* 6, (2011).
25. A. Sarrion-Perdigones et al., GoldenBraid 2.0: A Comprehensive DNA Assembly Framework for Plant Synthetic Biology. *Plant Physiol* 162, 1618-1631 (2013).
26. H. C. De Paoli, G. A. Tuskan, X. Yang, An innovative platform for quick and flexible joining of assorted DNA fragments. *Sci Rep* 6, 19278 (2016).
27. E. Weber, C. Engler, R. Gruetzner, S. Werner, S. Marillonnet, A Modular Cloning System for Standardized Assembly of Multigene Constructs. *Plos One* 6, (2011).
28. S. Werner, C. Engler, E. Weber, R. Gruetzner, S. Marillonnet, Fast track assembly of multigene constructs using Golden Gate cloning and the MoClo system. *Bioengineered* 3, 38-43 (2012).
29. A. Binder et al., A Modular Plasmid Assembly Kit for Multigene Expression, Gene Silencing and Silencing Rescue in Plants. *Plos One* 9, (2014).
30. N. J. Patron et al., Standards for plant synthetic biology: a common syntax for exchange of DNA parts. *The New phytologist* 208, 13-19 (2015).
31. R. Beck, H. Burtscher, Introduction of arbitrary sequences into genes by use of class IIs restriction enzymes. *Nucleic Acids Res* 22, 886-887 (1994).
32. N. Agmon et al., Yeast Golden Gate (yGG) for the Efficient Assembly of *S. cerevisiae* Transcription Units. *Acs Synth Biol* 4, 853-859 (2015).
33. K. Miyazaki, Molecular engineering of a PheS counter-selection marker for improved operating efficiency in *Escherichia coli*. *BioTechniques* 58, 86-88 (2015).
34. M. M. Yelton, 3. E. Hamer, W. E. Timberlake, Transformation of *Aspergillus nidulans* by using a trpC plasmid. *Proceedings of the National Academy of Sciences of the United States of America* 81, 1470-1474 (1984).
35. S. 3. Vollmer, C. Yanofsky, Efficient cloning of genes of *Neurospora crassa*. *Proceedings of the National Academy of Sciences of the United States of America* 83, 4869-4873 (1986).
36. R. P. Oliver et al., Transformation of *Fulvia fulva*, a fungal pathogen of tomato, to hygromycin B resistance *Current genetics* 12, 231-233 (1987).

37. S. Saikia, E. J. Parker, A. Koulman, B. Scott, Four gene products are required for the fungal synthesis of the indole-diterpene, paspaline. *FEBS letters* 580, 1625-1630 (2006).
38. B. Scott et al., Deletion and gene expression analyses define the paxilline biosynthetic gene cluster in *Penicillium paxilli*. *Toxins* 5, 1422-1446 (2013).
39. R. Grigaite, Z. Maneliene, A. Janulaitis, AarI, a restriction endonuclease from *Arthrobacter aurescens* SS2-322, which recognizes the novel non-palindromic sequence 5'-CACCTGC(N)4/8-3'. *Nucleic Acids Res* 30, e123 (2002).
40. L. K. McMillan et al., Molecular analysis of two cytochrome P450 monooxygenase genes required for paxilline biosynthesis in *Penicillium paxilli*, and effects of paxilline intermediates on mammalian maxi-K ion channels. *Molecular genetics and genomics: MGG* 270, 9-23 (2003).
41. A. de Marco, E. Deuerling, A. Mogk, T. Tomoyasu, B. Bukau, Chaperone-based procedure to increase yields of soluble recombinant proteins produced in *E. coli*. *BMC biotechnology* 7, 32 (2007).
42. F. Namiki et al., Mutation of an arginine biosynthesis gene causes reduced pathogenicity in *Fusarium oxysporum* f. sp *melonis*. *Mol Plant Microbe In* 14, 580-584 (2001).
43. Y. Itoh, R. Johnson, B. Scott, Integrative transformation of the mycotoxin-producing fungus, *Penicillium paxilli*. *Current genetics* 25, 508-513 (1994).
44. C. Young et al., Paxilline-negative mutants of *Penicillium paxilli* generated by heterologous and homologous plasmid integration. *Current genetics* 33, 368-377 (1998).

What we claim is:

1. A vector set comprising at least two shuttle vectors, V1 and V2, wherein V1 is selected from the group consisting of
V1.1(+)=5'-A1 B1 M1 B2 C1 C2 A2-3',
V1.2(−)=5'-A1 C1 C2 B1 M1 B2 A2-3',
V1.3(+)=5'-A1 B2 M1 B1 C1 C2 A2-3', and
V1.4(−)=5'-A1 C1 C2 B2 M1 B1 A2-3',
and V2 is selected from the group consisting of
V2.1(+)=5'-C1 B1 M1 B2 A1 M2 A2 C2-3',
V2.2(−)=5'-C1 A1 M2 A2 B1 M1 B2 C2-3',
V2.3(+)=5'-C1 B2 M1 B1 A1 M2 A2 C2-3', and
V2.4(−)=5'-C1 A1 M2 A2 B2 M1 B1 C2-3',
wherein M1 is a selectable marker, M2 is a scorable marker, and A1, A2, B1, B2, C1 and C2 are Type IIS restriction enzyme recognition sites, wherein A1, B1 and C1 are all different Type IIS restriction enzyme recognition sites, and wherein A1=A2, C1=C2, and B1=B2 or B1≠B2.

2. The vector set of claim 1 comprising three, four, five, six, seven, or eight different shuttle vectors.

3. The vector set of claim 1, wherein A1, A2, B1, B2, C1 and C2 comprise at least four, or six, Type IIS restriction sites.

4. The vector set of claim 1 further comprising a source vector or a destination vector or both, wherein the destination vector comprises a pair of restriction sites that are the same as A1 and A2 or as C1 and C2, wherein the destination vector optionally comprises a marker (DM) flanked by the pair of restriction sites, wherein the DM, when present, is the same as M2 in the V2 shuttle vectors.

5. The vector set of claim 1 comprising at least four shuttle vectors as follows:
(a) at least two V1 vectors and at least two V2 vectors,
(b) at least one V1 vector and at least three V2 vectors, or
(c) at least three V1 vectors and at least one V2 vector, wherein each of (a), (b) and (c) comprises at least one (−) vector and at least one (+) vector,
or comprising at least five shuttle vectors as follows:
(d) at least two V1 vectors and at least three V2 vectors,
(e) at least three V1 vectors and at least two V2 vectors,
(f) four V1 vectors and at least one V2 vector, or
(g) at least one V1 vector and four V2 vectors,
wherein each of (d), (e), (f) and (g) comprises at least one (−) vector and at least one (+) vector,
or comprising at least six shuttle vectors as follows:
(h) at least three V1 vectors and at least three V2 vectors,
(i) four V1 vectors and at least two V2 vectors,
(j) at least two V1 vectors and four V2 vectors,
wherein each of (i) and (j) comprises at least one (−) vector and at least one (+) vector,
or comprising at least seven shuttle vectors as follows:
(k) at least three V1 vectors and four V2 vectors,
(l) four V1 vectors and at least three V2 vectors.

6. The vector set of claim 1 comprising V1.1(+), V1.2(−), V1.3(+), V1.4(−), V2.1(+), V2.2(−), V2.3(+) and V2.4(−).

7. The vector set of claim 6, wherein V1.1(+) is pML2(+)WF comprising the nucleotide sequence SEQ ID NO: 122; V1.2(−) is pML2(−)WR comprising the nucleotide sequence SEQ ID NO: 123; V1.3(+) is pML2(+)WR comprising the nucleotide sequence SEQ ID NO: 124; V1.4(−) is pML2(−)WF comprising the nucleotide sequence SEQ ID NO: 125; V2.1(+) is pML2(+)BF comprising the nucleotide sequence SEQ ID NO: 126; V2.2(−) is pML2(−)BR comprising the nucleotide sequence SEQ ID NO: 127; V2.3(+) is pML2(+)BR comprising the nucleotide sequence SEQ ID NO: 128; and V2.4(−) is pML2(−)BF comprising the nucleotide sequence SEQ ID NO: 129.

8. The vector set of claim 1, wherein A1 and A2 are in a convergent orientation relative to each other in V1.1(+), V1.2(−), V1.3(+) and V1.4(−).

9. The vector set of claim 1, wherein the vectors in the vector set are components in a cloning system, wherein the cloning system is useful for making a gene construct comprising at least one transcription unit (TU).

10. A vector set comprising at least three shuttle vectors, wherein at least two of the three vectors are V1 vectors selected from the group consisting of
V1.1(+)=5′-A1 B1 M1 B2 C1 C2 A2-3′,
V1.2(−)=5′-A1 C1 C2 B1 M1 B2 A2-3′,
V1.3(+)=5′-A1 B2 M1 B1 C1 C2 A2-3′, and
V1.4(−)=5′-A1 C1 C2 B2 M1 B1 A2-3′,
wherein at least one of the V1 vectors is a (+) vector and another V1 vector is a (−) vector,
and wherein at least one of the three vectors is a V2 vector selected from the group consisting of
V2.1(+)=5′-C1 B1 M1 B2 A1 M2 A2 C2-3′,
V2.2(−)=5′-C1 A1 M2 A2 B1 M1 B2 C2-3′,
V2.3(+)=5′-C1 B2 M1 B1 A1 M2 A2 C2-3′, and
V2.4(−)=5′-C1 A1 M2 A2 B2 M1 B1 C2-3′,
wherein M1 is a selectable marker, M2 is a scorable marker, and A1, A2, B1, B2, C1 and C2 are Type IIS restriction enzyme recognition sites,
wherein A1, B1 and C1 are all different Type IIS restriction enzyme recognition sites, and
wherein A1=A2, C1=C2, and B1=B2 or B1≠B2.

11. A vector set comprising at least two shuttle vectors, wherein
each shuttle vector comprises a selectable marker (M1), and at least six restriction sites, wherein at least four of the restriction sites are Type IIS restriction enzyme recognition sites,
wherein in at least one first shuttle vector, a first four restriction sites are located 3′ or 5′ of M1, at least three of the four being Type IIS restriction enzyme recognition sites, and a second two restriction sites are located 3′ or 5′ of M1, at least one of the two being a Type IIS restriction enzyme recognition site, and
wherein in at least one second shuttle vector, a first four restriction sites are located 3′ or 5′ of M1, at least three of the four being Type IIS restriction enzyme recognition sites, and a second two restriction sites are located 5′ or 3′ of M1, at least one of the two being a Type IIS restriction enzyme recognition site,
wherein the at least one second shuttle vector comprises at least one scorable marker (M2) flanked by two Type IIS restriction enzyme recognition sites, and
wherein when the first four restriction sites are located 3′ of M1 in the at least one first or second vector, the second two restriction sites are located 5′ of M1, and the vector is a (+) vector, and
when the first four restriction sites are located 5′ of M1 in the at least one first or second vector, the second two restriction sites are located 3′ of M1 and the vector is a (−) vector.

12. A set of eight shuttle vectors, each shuttle vector comprising a selectable marker (M1), and six restriction sites,
wherein each shuttle vector comprises a first set of four restriction sites positioned on one side of M1 and a second set of two restriction sites positioned on the other side of M1,
wherein
two of the restriction sites in the first set are the same as each other,
the two restriction sites in the second set are different from each other, and
at least one of the two restriction sites in the second set is the same as one of the four restriction sites in the first set, and
wherein four of the shuttle vectors comprise a scorable marker (M2),
wherein four of the vectors are (+) vectors comprising the first set of restriction sites 3′ of M1, and four of the vectors are (−) vectors comprising the first set of restriction sites 5′ of M1.

13. A set of vectors comprising
(i) the V1 shuttle vectors as defined in claim 1,
(ii) the V2 vectors as defined in claim 1, and
(iii) at least one destination vector comprising a pair of restriction sites,
wherein the pair of restriction sites in (iii) have a divergent orientation relative to each other and are the same as a pair of restriction sites in each of the shuttle vectors in (i), and in each of the shuttle vectors in (ii)
wherein the restriction sites in (i) have a convergent orientation relative to each other, and
wherein the restriction sites in (ii) have a divergent orientation relative to each other.

14. The vector set of claim 1, wherein A1, A2, B1, B2, C1 and C2 comprise at least four, or comprise six, Type IIS restriction enzyme recognition sites, A2 are AarI restriction sites, B1 and B2 are BsaI restriction sites, and/or C1 and C2 are BsmBI restriction sites.

15. The vector set of claim 1, wherein A1 and A2 are in a divergent orientation relative to each other in V2.1(+), V2.2(−), V2.3(+) and V2.4(−).

16. The vector set of claim 1, wherein C1 and C2 are in a divergent orientation relative to each other in V1.1(+), V1.2(−), V1.3(+) and V1.4(−).

17. The vector set of claim 1, wherein C1 and C2 are in a convergent orientation relative to each other in V2.1(+), V2.2(−), V2.3(+) and V2.4(−).

18. A method of making a multigene construct comprising at least two transcription units (TU), the method comprising:
(a) cloning a first cloning cassette comprising a first transcription unit (TU1), and four Type IIS restriction enzyme recognition sites A1, A2, C1 and C2 arranged in the following order:
5′-A1-TU1-C1-C2-A2-3′, or
5′-A1-C1-C2-TU1-A2-3′,
into a destination vector (V3) comprising a pair of Type IIS restriction enzyme recognition sites A1 and A2 flanking a storable marker (M2) to make:
destination vector V3.1 comprising 5′-TU1-C1-C2-3′ or
destination vector V3.2 comprising 5′-C1-C2-TU1-3′,
(b) cloning a second cloning cassette comprising a second transcription unit (TU2), the scorable marker (M2), and four Type IIS restriction enzyme recognition sites A1, A2, C1 and C2 arranged in the following order:
5′-C1-TU2-A1-M2-A2-C2-3′, or
5′-C1-A1-M2-A2-TU2-C2-3′,
into V3.1 to make destination vector V4.1 comprising 5′-TU1-TU2-A1-M2-A2-3′, or destination vector V4.2 comprising 5′-TU1-A1-M2-A2-TU2-3′, or
into V3.2 to make destination vector V4.3 comprising 5′-TU2-A1-M2-A2-TU1-3′, or destination vector V4.4 comprising 5′-A1-M2-A2-TU2-TU1-3′
wherein A1 and C1 are different Type IIS restriction enzyme recognition sites, and
wherein A1=A2 and C1=C2.

19. The method of claim 18 wherein A1, A2, C1 and C2 are Type IIS restriction enzyme recognition sites selected from the group consisting of BsaI, AarI and BsmBI sites.

* * * * *

SEQUENCE LISTING

```
<160> NUMBER OF SEQ ID NOS: 129

<210> SEQ ID NO 1
<211> LENGTH: 10
<212> TYPE: DNA
<213> ORGANISM: Artificial Sequence
<220> FEATURE:
<223> OTHER INFORMATION: Primer

<400> SEQUENCE: 1
cgcttgagac                                                                 10

<210> SEQ ID NO 2
<211> LENGTH: 146
<212> TYPE: DNA
<213> ORGANISM: Artificial Sequence
<220> FEATURE:
<223> OTHER INFORMATION: Cassette

<400> SEQUENCE: 2
gaccccgtag gtgtccatgg cacctgcagc tcattggaga gagaccttaa gcttgcagca          60
gcggtctctc gctcattaga gacggccgga ttgcggccgc taaccggccg tctcacgtaa         120
tatgcaggtg ctcgagggca tcaaat                                              146

<210> SEQ ID NO 3
<211> LENGTH: 146
<212> TYPE: DNA
<213> ORGANISM: Artificial Sequence
<220> FEATURE:
<223> OTHER INFORMATION: Cassette

<400> SEQUENCE: 3
gaccccgtag gtgtccatgg cacctgcagc tcattagcga gagaccttaa gcttgcagca          60
gcggtctctc tcccattaga gacggccgga ttgcggccgc taaccggccg tctcacgtaa         120
tatgcaggtg ctcgagggca tcaaat                                              146

<210> SEQ ID NO 4
<211> LENGTH: 146
<212> TYPE: DNA
<213> ORGANISM: Artificial Sequence
<220> FEATURE:
<223> OTHER INFORMATION: Cassette

<400> SEQUENCE: 4
gaccccgtag gtgtccatgg cacctgcagc tcattagaga cggccggatt gcggccgcta          60
```

```
accggccgtc tcacgtagga gagagacctt aagcttgcag cagcggtctc tcgctcgtaa    120
tatgcaggtg ctcgagggca tcaaat                                        146
```

<210> SEQ ID NO 5
<211> LENGTH: 146
<212> TYPE: DNA
<213> ORGANISM: Artificial Sequence
<220> FEATURE:
<223> OTHER INFORMATION: Cassette

<400> SEQUENCE: 5

```
gaccccgtag gtgtccatgg cacctgcagc tcattagaga cggccggatt gcggccgcta    60
accggccgtc tcacgtaagc gagagacctt aagcttgcag cagcggtctc tctcccgtaa   120
tatgcaggtg ctcgagggca tcaaat                                        146
```

<210> SEQ ID NO 6
<211> LENGTH: 146
<212> TYPE: DNA
<213> ORGANISM: Artificial Sequence
<220> FEATURE:
<223> OTHER INFORMATION: Cassette

<400> SEQUENCE: 6

```
gaccccgtag gtgtccatgg cgtctcacat tggagagaga ccttaagctt gcagcagcgg    60
tctctcgctc attatatgca ggtggccgga ttgcggccgc taaccggcca cctgcagctc   120
gtaagagacg ctcgagggca tcaaat                                        146
```

<210> SEQ ID NO 7
<211> LENGTH: 146
<212> TYPE: DNA
<213> ORGANISM: Artificial Sequence
<220> FEATURE:
<223> OTHER INFORMATION: Cassette

<400> SEQUENCE: 7

```
gaccccgtag gtgtccatgg cgtctcacat tagcgagaga ccttaagctt gcagcagcgg    60
tctctctccc attatatgca ggtggccgga ttgcggccgc taaccggcca cctgcagctc   120
gtaagagacg ctcgagggca tcaaat                                        146
```

<210> SEQ ID NO 8
<211> LENGTH: 146
<212> TYPE: DNA
<213> ORGANISM: Artificial Sequence
<220> FEATURE:
<223> OTHER INFORMATION: Cassette

<400> SEQUENCE: 8

```
gaccccgtag gtgtccatgg cgtctcacat tatatgcagg tggccggatt gcggccgcta    60
accggccacc tgcagctcgt aggagagaga ccttaagctt gcagcagcgg tctctcgctc   120
gtaagagacg ctcgagggca tcaaat                                        146
```

<210> SEQ ID NO 9
<211> LENGTH: 146
<212> TYPE: DNA
<213> ORGANISM: Artificial Sequence
<220> FEATURE:
<223> OTHER INFORMATION: Cassette

<400> SEQUENCE: 9

```
gaccccgtag gtgtccatgg cgtctcacat tatatgcagg tggccggatt gcggccgcta    60
```

```
accggccacc tgcagctcgt aagcgagaga ccttaagctt gcagcagcgg tctctctccc    120
gtaagagacg ctcgagggca tcaaat                                         146

<210> SEQ ID NO 10
<211> LENGTH: 41
<212> TYPE: DNA
<213> ORGANISM: Artificial Sequence
<220> FEATURE:
<223> OTHER INFORMATION: Primer

<400> SEQUENCE: 10
cgctcacggt ctcaaccgga cgtcgatatc cggatgaagg c                         41

<210> SEQ ID NO 11
<211> LENGTH: 45
<212> TYPE: DNA
<213> ORGANISM: Artificial Sequence
<220> FEATURE:
<223> OTHER INFORMATION: Primer

<400> SEQUENCE: 11
tgaacgaggt ctcaattctt atttgccgac taccttggtg atctc                     45

<210> SEQ ID NO 12
<211> LENGTH: 55
<212> TYPE: DNA
<213> ORGANISM: Artificial Sequence
<220> FEATURE:
<223> OTHER INFORMATION: Primer

<400> SEQUENCE: 12
gatgagttgg tctcagaatt aattcatgag cggatacata tttgaatgta tttag          55

<210> SEQ ID NO 13
<211> LENGTH: 35
<212> TYPE: DNA
<213> ORGANISM: Artificial Sequence
<220> FEATURE:
<223> OTHER INFORMATION: Primer

<400> SEQUENCE: 13
gaggaacggt ctccacactg gcgaatggga cgcgc                                35

<210> SEQ ID NO 14
<211> LENGTH: 47
<212> TYPE: DNA
<213> ORGANISM: Artificial Sequence
<220> FEATURE:
<223> OTHER INFORMATION: Primer

<400> SEQUENCE: 14
ctttccggtc tcagtgtcca tggttattac caggcaaagc gccattc                   47

<210> SEQ ID NO 15
<211> LENGTH: 54
<212> TYPE: DNA
<213> ORGANISM: Artificial Sequence
<220> FEATURE:
<223> OTHER INFORMATION: Primer

<400> SEQUENCE: 15
gacaggtttg gtctcgtgcc ctcgagcagc tggcgcaacg caattaatgt gagt           54

<210> SEQ ID NO 16
```

```
<211> LENGTH: 39
<212> TYPE: DNA
<213> ORGANISM: Artificial Sequence
<220> FEATURE:
<223> OTHER INFORMATION: Primer

<400> SEQUENCE: 16
cacattaagg tctctggcat cactgcccgc tttccagtc                           39

<210> SEQ ID NO 17
<211> LENGTH: 50
<212> TYPE: DNA
<213> ORGANISM: Artificial Sequence
<220> FEATURE:
<223> OTHER INFORMATION: Primer

<400> SEQUENCE: 17
tgattaggtc tcgcggtctg tcagaccaag tttactcata tatactttag              50

<210> SEQ ID NO 18
<211> LENGTH: 50
<212> TYPE: DNA
<213> ORGANISM: Artificial Sequence
<220> FEATURE:
<223> OTHER INFORMATION: Primer

<400> SEQUENCE: 18
cagctttccc atggtctcgt gagacgttat taccaggcaa agcgccattc              50

<210> SEQ ID NO 19
<211> LENGTH: 46
<212> TYPE: DNA
<213> ORGANISM: Artificial Sequence
<220> FEATURE:
<223> OTHER INFORMATION: Primer

<400> SEQUENCE: 19
tcccgacctc gaggtctaga gacggcgcaa cgcaattaat gtgagt                  46

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
agaagatccg gtctccaccg ctacggggtc tgacgctcag                         40

<210> SEQ ID NO 21
<211> LENGTH: 38
<212> TYPE: DNA
<213> ORGANISM: Artificial Sequence
<220> FEATURE:
<223> OTHER INFORMATION: Primer

<400> SEQUENCE: 21
gattgcgggt ctcccaaacg aaatacgcga tcgctgtt                           38

<210> SEQ ID NO 22
<211> LENGTH: 37
<212> TYPE: DNA
<213> ORGANISM: Artificial Sequence
<220> FEATURE:
<223> OTHER INFORMATION: Primer

<400> SEQUENCE: 22
```

```
atcgcgggtc tcgtttggct caggcgcaat cacgaat                              37
```

<210> SEQ ID NO 23
<211> LENGTH: 35
<212> TYPE: DNA
<213> ORGANISM: Artificial Sequence
<220> FEATURE:
<223> OTHER INFORMATION: Primer

<400> SEQUENCE: 23

```
gaggaacggt ctccacactg gcgaatggga cgcgc                                35
```

<210> SEQ ID NO 24
<211> LENGTH: 47
<212> TYPE: DNA
<213> ORGANISM: Artificial Sequence
<220> FEATURE:
<223> OTHER INFORMATION: Primer

<400> SEQUENCE: 24

```
ctttccggtc tcagtgtcca tggttattac caggcaaagc gccattc                   47
```

<210> SEQ ID NO 25
<211> LENGTH: 46
<212> TYPE: DNA
<213> ORGANISM: Artificial Sequence
<220> FEATURE:
<223> OTHER INFORMATION: Primer

<400> SEQUENCE: 25

```
cccgacggtc tcgtgccctc gaggcgcaac gcaattaatg tgagtt                    46
```

<210> SEQ ID NO 26
<211> LENGTH: 39
<212> TYPE: DNA
<213> ORGANISM: Artificial Sequence
<220> FEATURE:
<223> OTHER INFORMATION: Primer

<400> SEQUENCE: 26

```
cacattaagg tctctggcat cactgcccgc tttccagtc                            39
```

<210> SEQ ID NO 27
<211> LENGTH: 50
<212> TYPE: DNA
<213> ORGANISM: Artificial Sequence
<220> FEATURE:
<223> OTHER INFORMATION: Primer

<400> SEQUENCE: 27

```
tgattaggtc tcgcggtctg tcagaccaag tttactcata tactttag                  50
```

<210> SEQ ID NO 28
<211> LENGTH: 53
<212> TYPE: DNA
<213> ORGANISM: Artificial Sequence
<220> FEATURE:
<223> OTHER INFORMATION: Primer

<400> SEQUENCE: 28

```
agccagcggt ctcacattgc ttgcaggtgt tattaccagg caaagcgcca ttc            53
```

<210> SEQ ID NO 29
<211> LENGTH: 52
<212> TYPE: DNA

```
<213> ORGANISM: Artificial Sequence
<220> FEATURE:
<223> OTHER INFORMATION: Primer

<400> SEQUENCE: 29
caggtttcgg tctcgtacgg cgggcaggtg gcgcaacgca attaatgtga gt          52

<210> SEQ ID NO 30
<211> LENGTH: 45
<212> TYPE: DNA
<213> ORGANISM: Artificial Sequence
<220> FEATURE:
<223> OTHER INFORMATION: Primer

<400> SEQUENCE: 30
ccacctggag agagaccaag ctttgatcgg cacgtaagag gttcc                  45

<210> SEQ ID NO 31
<211> LENGTH: 42
<212> TYPE: DNA
<213> ORGANISM: Artificial Sequence
<220> FEATURE:
<223> OTHER INFORMATION: Primer

<400> SEQUENCE: 31
cctttccggt ctcttttagc ttccttagct cctgaaaatc tc                     42

<210> SEQ ID NO 32
<211> LENGTH: 39
<212> TYPE: DNA
<213> ORGANISM: Artificial Sequence
<220> FEATURE:
<223> OTHER INFORMATION: Primer

<400> SEQUENCE: 32
agggaaaggt ctcataaaat gtcacatctc gcagaactg                         39

<210> SEQ ID NO 33
<211> LENGTH: 54
<212> TYPE: DNA
<213> ORGANISM: Artificial Sequence
<220> FEATURE:
<223> OTHER INFORMATION: Primer

<400> SEQUENCE: 33
tgcctggagc gagagaccaa gcttttatta tttaaactgt ttgaggaaac gcag        54

<210> SEQ ID NO 34
<211> LENGTH: 41
<212> TYPE: DNA
<213> ORGANISM: Artificial Sequence
<220> FEATURE:
<223> OTHER INFORMATION: Primer

<400> SEQUENCE: 34
cgctcacggt ctcaaccgga cgtcgatatc cggatgaagg c                      41

<210> SEQ ID NO 35
<211> LENGTH: 45
<212> TYPE: DNA
<213> ORGANISM: Artificial Sequence
<220> FEATURE:
<223> OTHER INFORMATION: Primer

<400> SEQUENCE: 35
tgaacgaggt ctcaattctt atttgccgac taccttggtg atctc                  45
```

<210> SEQ ID NO 36
<211> LENGTH: 55
<212> TYPE: DNA
<213> ORGANISM: Artificial Sequence
<220> FEATURE:
<223> OTHER INFORMATION: Primer

<400> SEQUENCE: 36
gatgagttgg tctcagaatt aattcatgag cggatacata tttgaatgta tttag    55

<210> SEQ ID NO 37
<211> LENGTH: 35
<212> TYPE: DNA
<213> ORGANISM: Artificial Sequence
<220> FEATURE:
<223> OTHER INFORMATION: Primer

<400> SEQUENCE: 37
gaggaacggt ctccacactg gcgaatggga cgcgc    35

<210> SEQ ID NO 38
<211> LENGTH: 58
<212> TYPE: DNA
<213> ORGANISM: Artificial Sequence
<220> FEATURE:
<223> OTHER INFORMATION: Primer

<400> SEQUENCE: 38
actccagcgg tctcagtgtc attgcttgca ggtgttatta ccaggcaaag cgccattc    58

<210> SEQ ID NO 39
<211> LENGTH: 55
<212> TYPE: DNA
<213> ORGANISM: Artificial Sequence
<220> FEATURE:
<223> OTHER INFORMATION: Primer

<400> SEQUENCE: 39
cgacaggggt ctcgtgccta cggcgggcag gtggcgcaac gcaattaatg tgagt    55

<210> SEQ ID NO 40
<211> LENGTH: 39
<212> TYPE: DNA
<213> ORGANISM: Artificial Sequence
<220> FEATURE:
<223> OTHER INFORMATION: Primer

<400> SEQUENCE: 40
cacattaagg tctctggcat cactgcccgc tttccagtc    39

<210> SEQ ID NO 41
<211> LENGTH: 50
<212> TYPE: DNA
<213> ORGANISM: Artificial Sequence
<220> FEATURE:
<223> OTHER INFORMATION: Primer

<400> SEQUENCE: 41
tgattaggtc tcgcggtctg tcagaccaag tttactcata tatactttag    50

<210> SEQ ID NO 42
<211> LENGTH: 22
<212> TYPE: DNA
<213> ORGANISM: Artificial Sequence
<220> FEATURE:

<223> OTHER INFORMATION: Primer

<400> SEQUENCE: 42
cgatgtacgt ctcactcggg ag                                    22

<210> SEQ ID NO 43
<211> LENGTH: 24
<212> TYPE: DNA
<213> ORGANISM: Artificial Sequence
<220> FEATURE:
<223> OTHER INFORMATION: Primer

<400> SEQUENCE: 43
gacctttcgt ctctgtctca catt                                  24

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
cgatgtacgt ctcactcgaa tg                                    22

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
gacctttcgt ctctgtctca aagc                                  24

<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
cgatgtacgt ctcactcggc tt                                    22

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
gacctttcgt ctctgtctca agcg                                  24

<210> SEQ ID NO 48
<211> LENGTH: 45
<212> TYPE: DNA
<213> ORGANISM: Artificial Sequence
<220> FEATURE:
<223> OTHER INFORMATION: Primer

<400> SEQUENCE: 48
cgatgtacgt ctcactcggg agattcacga cctgtgacta gtcaa           45

<210> SEQ ID NO 49
<211> LENGTH: 48
<212> TYPE: DNA
<213> ORGANISM: Artificial Sequence
<220> FEATURE:
<223> OTHER INFORMATION: Primer

<400> SEQUENCE: 49
gacctttcgt ctctgtctca cattgcgtcg aacttgatga agtttttct        48

<210> SEQ ID NO 50
<211> LENGTH: 41
<212> TYPE: DNA
<213> ORGANISM: Artificial Sequence
<220> FEATURE:
<223> OTHER INFORMATION: Primer

<400> SEQUENCE: 50
cgatgtacgt ctcactcgaa tgtcctacat ccttgcagaa g        41

<210> SEQ ID NO 51
<211> LENGTH: 36
<212> TYPE: DNA
<213> ORGANISM: Artificial Sequence
<220> FEATURE:
<223> OTHER INFORMATION: Primer

<400> SEQUENCE: 51
cttctacgtc tcgtactgtt ctaatcgtgc ttggtg        36

<210> SEQ ID NO 52
<211> LENGTH: 41
<212> TYPE: DNA
<213> ORGANISM: Artificial Sequence
<220> FEATURE:
<223> OTHER INFORMATION: Primer

<400> SEQUENCE: 52
gcacgacgtc tccagtacag gtgctagaag atgacgttga c        41

<210> SEQ ID NO 53
<211> LENGTH: 42
<212> TYPE: DNA
<213> ORGANISM: Artificial Sequence
<220> FEATURE:
<223> OTHER INFORMATION: Primer

<400> SEQUENCE: 53
aggcgccgtc tccaccaatc tctttcaatc ttgcttgttg ga        42

<210> SEQ ID NO 54
<211> LENGTH: 31
<212> TYPE: DNA
<213> ORGANISM: Artificial Sequence
<220> FEATURE:
<223> OTHER INFORMATION: Primer

<400> SEQUENCE: 54
gattgacgtc tcttggtgac ccccgcgcct t        31

<210> SEQ ID NO 55
<211> LENGTH: 39
<212> TYPE: DNA
<213> ORGANISM: Artificial Sequence
<220> FEATURE:
<223> OTHER INFORMATION: Primer

<400> SEQUENCE: 55
gtcgaccgtc tctttcccta gtatattgga agctccccg                          39

<210> SEQ ID NO 56
<211> LENGTH: 38
<212> TYPE: DNA
<213> ORGANISM: Artificial Sequence
<220> FEATURE:
<223> OTHER INFORMATION: Primer

<400> SEQUENCE: 56
tccaatcgtc tcgggaaacc ctaagtcgac ttagtgcg                           38

<210> SEQ ID NO 57
<211> LENGTH: 52
<212> TYPE: DNA
<213> ORGANISM: Artificial Sequence
<220> FEATURE:
<223> OTHER INFORMATION: Primer

<400> SEQUENCE: 57
gacctttcgt ctctgtctca aagcttaaac tcttcctttc tcattagtag gg           52

<210> SEQ ID NO 58
<211> LENGTH: 44
<212> TYPE: DNA
<213> ORGANISM: Artificial Sequence
<220> FEATURE:
<223> OTHER INFORMATION: Primer

<400> SEQUENCE: 58
cgatgtacgt ctcactcggc tttcaatcgt gctgcatttc tctt                    44

<210> SEQ ID NO 59
<211> LENGTH: 45
<212> TYPE: DNA
<213> ORGANISM: Artificial Sequence
<220> FEATURE:
<223> OTHER INFORMATION: Primer

<400> SEQUENCE: 59
gacctttcgt ctctgtctca agcgtcactc ccgagcaata ttgct                   45

<210> SEQ ID NO 60
<211> LENGTH: 44
<212> TYPE: DNA
<213> ORGANISM: Artificial Sequence
<220> FEATURE:
<223> OTHER INFORMATION: Primer

<400> SEQUENCE: 60
cgatgtacgt ctcactcggg aggttgttgg catgggagta ggat                    44

<210> SEQ ID NO 61
<211> LENGTH: 60
<212> TYPE: DNA
<213> ORGANISM: Artificial Sequence
<220> FEATURE:
<223> OTHER INFORMATION: Primer

<400> SEQUENCE: 61
gacctttcgt ctctgtctac attgtttctg aatcttaaag atacatgaaa agaataaagc   60

<210> SEQ ID NO 62
<211> LENGTH: 41

```
<212> TYPE: DNA
<213> ORGANISM: Artificial Sequence
<220> FEATURE:
<223> OTHER INFORMATION: Primer

<400> SEQUENCE: 62
cgatgtacgt ctcactcgaa tggaaaaggc cgagtttcaa g                 41

<210> SEQ ID NO 63
<211> LENGTH: 38
<212> TYPE: DNA
<213> ORGANISM: Artificial Sequence
<220> FEATURE:
<223> OTHER INFORMATION: Primer

<400> SEQUENCE: 63
tgacaacgtc tcgtccatcg aataaagcgt tgacttgc                     38

<210> SEQ ID NO 64
<211> LENGTH: 45
<212> TYPE: DNA
<213> ORGANISM: Artificial Sequence
<220> FEATURE:
<223> OTHER INFORMATION: Primer

<400> SEQUENCE: 64
acgcttcgtc tcatggactc actattgtca caatccatgg aaaag             45

<210> SEQ ID NO 65
<211> LENGTH: 56
<212> TYPE: DNA
<213> ORGANISM: Artificial Sequence
<220> FEATURE:
<223> OTHER INFORMATION: Primer

<400> SEQUENCE: 65
gacctttcgt ctctgtctca aagcttaaac ttgaagaaaa taaaacttca gggcac 56

<210> SEQ ID NO 66
<211> LENGTH: 47
<212> TYPE: DNA
<213> ORGANISM: Artificial Sequence
<220> FEATURE:
<223> OTHER INFORMATION: Primer

<400> SEQUENCE: 66
cgatgtacgt ctcactcggc ttaccattgg agcaattttt ggttttc           47

<210> SEQ ID NO 67
<211> LENGTH: 33
<212> TYPE: DNA
<213> ORGANISM: Artificial Sequence
<220> FEATURE:
<223> OTHER INFORMATION: Primer

<400> SEQUENCE: 67
gttcgccgtc tcgactcgat tgcttgtggg tct                          33

<210> SEQ ID NO 68
<211> LENGTH: 33
<212> TYPE: DNA
<213> ORGANISM: Artificial Sequence
<220> FEATURE:
<223> OTHER INFORMATION: Primer

<400> SEQUENCE: 68
```

```
acaagccgtc tccgagtcca gccagcgaac ttg                          33
```

<210> SEQ ID NO 69
<211> LENGTH: 53
<212> TYPE: DNA
<213> ORGANISM: Artificial Sequence
<220> FEATURE:
<223> OTHER INFORMATION: Primer

<400> SEQUENCE: 69

```
gacctttcgt ctctgtctca agcgttttgg cttacttcag tttaactgtt ttg    53
```

<210> SEQ ID NO 70
<211> LENGTH: 43
<212> TYPE: DNA
<213> ORGANISM: Artificial Sequence
<220> FEATURE:
<223> OTHER INFORMATION: Primer

<400> SEQUENCE: 70

```
cgatgtacgt ctcactcggg agaaggctgt gttggagaga atc               43
```

<210> SEQ ID NO 71
<211> LENGTH: 50
<212> TYPE: DNA
<213> ORGANISM: Artificial Sequence
<220> FEATURE:
<223> OTHER INFORMATION: Primer

<400> SEQUENCE: 71

```
gacctttcgt ctctgtctca cattgtttct aaggttgacg tgggaaaaag        50
```

<210> SEQ ID NO 72
<211> LENGTH: 43
<212> TYPE: DNA
<213> ORGANISM: Artificial Sequence
<220> FEATURE:
<223> OTHER INFORMATION: Primer

<400> SEQUENCE: 72

```
cgatgtacgt ctcactcgaa tggacggttt tgatgtttcc caa               43
```

<210> SEQ ID NO 73
<211> LENGTH: 53
<212> TYPE: DNA
<213> ORGANISM: Artificial Sequence
<220> FEATURE:
<223> OTHER INFORMATION: Primer

<400> SEQUENCE: 73

```
gacctttcgt ctctgtctca aagctcaatt tgcttttttc ggcccgctta tgc    53
```

<210> SEQ ID NO 74
<211> LENGTH: 42
<212> TYPE: DNA
<213> ORGANISM: Artificial Sequence
<220> FEATURE:
<223> OTHER INFORMATION: Primer

<400> SEQUENCE: 74

```
cgatgtacgt ctcactcggc tttcggcagt tgagggtgaa ac                42
```

<210> SEQ ID NO 75
<211> LENGTH: 50
<212> TYPE: DNA
<213> ORGANISM: Artificial Sequence
<220> FEATURE:
<223> OTHER INFORMATION: Primer

<400> SEQUENCE: 75
gacctttcgt ctctgtctca agcgggttaa caatgaggaa cgatgaacag        50

<210> SEQ ID NO 76
<211> LENGTH: 45
<212> TYPE: DNA
<213> ORGANISM: Artificial Sequence
<220> FEATURE:
<223> OTHER INFORMATION: Primer

<400> SEQUENCE: 76
cgatgtacgt ctcactcggg agacaacaaa aagatcagcc aatgg             45

<210> SEQ ID NO 77
<211> LENGTH: 46
<212> TYPE: DNA
<213> ORGANISM: Artificial Sequence
<220> FEATURE:
<223> OTHER INFORMATION: Primer

<400> SEQUENCE: 77
gacctttcgt ctctgtctca cattaaaatg ggacctacac cctgaa            46

<210> SEQ ID NO 78
<211> LENGTH: 35
<212> TYPE: DNA
<213> ORGANISM: Artificial Sequence
<220> FEATURE:
<223> OTHER INFORMATION: Primer

<400> SEQUENCE: 78
cgatgtacgt ctcactcgaa tgggcgtagc aggga                        35

<210> SEQ ID NO 79
<211> LENGTH: 31
<212> TYPE: DNA
<213> ORGANISM: Artificial Sequence
<220> FEATURE:
<223> OTHER INFORMATION: Primer

<400> SEQUENCE: 79
cattgacgtc tccacggcgc cagacaaggg a                            31

<210> SEQ ID NO 80
<211> LENGTH: 35
<212> TYPE: DNA
<213> ORGANISM: Artificial Sequence
<220> FEATURE:
<223> OTHER INFORMATION: Primer

<400> SEQUENCE: 80
cccttgcgtc tcgccgtgac ggagtcaatg ggttc                        35

<210> SEQ ID NO 81
<211> LENGTH: 46
<212> TYPE: DNA
<213> ORGANISM: Artificial Sequence
<220> FEATURE:
<223> OTHER INFORMATION: Primer

<400> SEQUENCE: 81
gacctttcgt ctctgtctca aagctcatgc cttcaggtca agcttc            46

<210> SEQ ID NO 82
<211> LENGTH: 47
<212> TYPE: DNA
<213> ORGANISM: Artificial Sequence
<220> FEATURE:
<223> OTHER INFORMATION: Primer

<400> SEQUENCE: 82
cgatgtacgt ctcactcggc ttttggcctt gtgaaatatg ggactac         47

<210> SEQ ID NO 83
<211> LENGTH: 49
<212> TYPE: DNA
<213> ORGANISM: Artificial Sequence
<220> FEATURE:
<223> OTHER INFORMATION: Primer

<400> SEQUENCE: 83
gacctttcgt ctctgtctca agcgatctct gtcatgtcgg atatcagat       49

<210> SEQ ID NO 84
<211> LENGTH: 51
<212> TYPE: DNA
<213> ORGANISM: Artificial Sequence
<220> FEATURE:
<223> OTHER INFORMATION: Primer

<400> SEQUENCE: 84
cgatgtacgt ctcactcggg agagggaaat ttggaaatag attacactcg a    51

<210> SEQ ID NO 85
<211> LENGTH: 60
<212> TYPE: DNA
<213> ORGANISM: Artificial Sequence
<220> FEATURE:
<223> OTHER INFORMATION: Primer

<400> SEQUENCE: 85
gacctttcgt ctctgtctca cattttcttt aggtagtttt agttaaatcg aggaaagaga   60

<210> SEQ ID NO 86
<211> LENGTH: 45
<212> TYPE: DNA
<213> ORGANISM: Artificial Sequence
<220> FEATURE:
<223> OTHER INFORMATION: Primer

<400> SEQUENCE: 86
cgatgtacgt ctcactcgaa tggatctatc cgatttccac atctc           45

<210> SEQ ID NO 87
<211> LENGTH: 38
<212> TYPE: DNA
<213> ORGANISM: Artificial Sequence
<220> FEATURE:
<223> OTHER INFORMATION: Primer

<400> SEQUENCE: 87
ggatagcgtc tcactctgtc tcaaacttga agtcatag                   38

<210> SEQ ID NO 88
<211> LENGTH: 40
<212> TYPE: DNA
<213> ORGANISM: Artificial Sequence
<220> FEATURE:
<223> OTHER INFORMATION: Primer

<400> SEQUENCE: 88
gctttacgtc tcaagagcac aaggaaagac cgaagaatct                          40

<210> SEQ ID NO 89
<211> LENGTH: 44
<212> TYPE: DNA
<213> ORGANISM: Artificial Sequence
<220> FEATURE:
<223> OTHER INFORMATION: Primer

<400> SEQUENCE: 89
gacctttcgt ctctgtctca aagcttacgc ctttgtagcc cgac                     44

<210> SEQ ID NO 90
<211> LENGTH: 42
<212> TYPE: DNA
<213> ORGANISM: Artificial Sequence
<220> FEATURE:
<223> OTHER INFORMATION: Primer

<400> SEQUENCE: 90
cgatgtacgt ctcactcggc ttatagggat acgttgccgg tc                       42

<210> SEQ ID NO 91
<211> LENGTH: 48
<212> TYPE: DNA
<213> ORGANISM: Artificial Sequence
<220> FEATURE:
<223> OTHER INFORMATION: Primer

<400> SEQUENCE: 91
gacctttcgt ctctgtctca agcggagcat ggattacaat tttgcgag                 48

<210> SEQ ID NO 92
<211> LENGTH: 48
<212> TYPE: DNA
<213> ORGANISM: Artificial Sequence
<220> FEATURE:
<223> OTHER INFORMATION: Primer

<400> SEQUENCE: 92
cgatgtacgt ctcactcggg agtctctagg atagatctgg cctttggt                 48

<210> SEQ ID NO 93
<211> LENGTH: 48
<212> TYPE: DNA
<213> ORGANISM: Artificial Sequence
<220> FEATURE:
<223> OTHER INFORMATION: Primer

<400> SEQUENCE: 93
gacctttcgt ctctgtctca cattcttgcg atagattcta acgaaggg                 48

<210> SEQ ID NO 94
<211> LENGTH: 44
<212> TYPE: DNA
<213> ORGANISM: Artificial Sequence
<220> FEATURE:
<223> OTHER INFORMATION: Primer

<400> SEQUENCE: 94
cgatgtacgt ctcactcgaa tggatttcgt gttatcagcc ttac                     44

<210> SEQ ID NO 95

```
<210> SEQ ID NO 95
<211> LENGTH: 34
<212> TYPE: DNA
<213> ORGANISM: Artificial Sequence
<220> FEATURE:
<223> OTHER INFORMATION: Primer

<400> SEQUENCE: 95
gcattgcgtc tcaagagcga tgaaaggagt gcag                              34

<210> SEQ ID NO 96
<211> LENGTH: 40
<212> TYPE: DNA
<213> ORGANISM: Artificial Sequence
<220> FEATURE:
<223> OTHER INFORMATION: Primer

<400> SEQUENCE: 96
gcacttcgtc tcactctcga aagttgcagg taattaactg                        40

<210> SEQ ID NO 97
<211> LENGTH: 37
<212> TYPE: DNA
<213> ORGANISM: Artificial Sequence
<220> FEATURE:
<223> OTHER INFORMATION: Primer

<400> SEQUENCE: 97
gcatgacgtc tcaacctgtc tcaaagcaag gcagctc                           37

<210> SEQ ID NO 98
<211> LENGTH: 33
<212> TYPE: DNA
<213> ORGANISM: Artificial Sequence
<220> FEATURE:
<223> OTHER INFORMATION: Primer

<400> SEQUENCE: 98
cgtcatcgtc tcaaggtgca agagttgtcg cac                               33

<210> SEQ ID NO 99
<211> LENGTH: 39
<212> TYPE: DNA
<213> ORGANISM: Artificial Sequence
<220> FEATURE:
<223> OTHER INFORMATION: Primer

<400> SEQUENCE: 99
gcatgacgtc tcaaggcctc gtcgctagct caaataaac                         39

<210> SEQ ID NO 100
<211> LENGTH: 35
<212> TYPE: DNA
<213> ORGANISM: Artificial Sequence
<220> FEATURE:
<223> OTHER INFORMATION: Primer

<400> SEQUENCE: 100
gcacttcgtc tcagcctgag tatgtcgagc ctctg                             35

<210> SEQ ID NO 101
<211> LENGTH: 46
<212> TYPE: DNA
<213> ORGANISM: Artificial Sequence
<220> FEATURE:
<223> OTHER INFORMATION: Primer

<400> SEQUENCE: 101
```

```
gacctttcgt ctctgtctca aagctcatgc cgagacagac tttctg       46
```

<210> SEQ ID NO 102
<211> LENGTH: 49
<212> TYPE: DNA
<213> ORGANISM: Artificial Sequence
<220> FEATURE:
<223> OTHER INFORMATION: Primer

<400> SEQUENCE: 102

```
cgatgtacgt ctcactcggc ttagggaaat ttggaaatag attacactc       49
```

<210> SEQ ID NO 103
<211> LENGTH: 48
<212> TYPE: DNA
<213> ORGANISM: Artificial Sequence
<220> FEATURE:
<223> OTHER INFORMATION: Primer

<400> SEQUENCE: 103

```
gacctttcgt ctctgtctca agcgtctagt ttcaaattcg ctgggttg       48
```

<210> SEQ ID NO 104
<211> LENGTH: 45
<212> TYPE: DNA
<213> ORGANISM: Artificial Sequence
<220> FEATURE:
<223> OTHER INFORMATION: Primer

<400> SEQUENCE: 104

```
cgatgtacgt ctcactcggg aggaattcat gccagttgtt cccag       45
```

<210> SEQ ID NO 105
<211> LENGTH: 31
<212> TYPE: DNA
<213> ORGANISM: Artificial Sequence
<220> FEATURE:
<223> OTHER INFORMATION: Primer

<400> SEQUENCE: 105

```
cgatgtacgt ctcagcttgg ccgactcgct g       31
```

<210> SEQ ID NO 106
<211> LENGTH: 36
<212> TYPE: DNA
<213> ORGANISM: Artificial Sequence
<220> FEATURE:
<223> OTHER INFORMATION: Primer

<400> SEQUENCE: 106

```
cacctttcgt ctccaagcag acgtgaagca ggacgg       36
```

<210> SEQ ID NO 107
<211> LENGTH: 33
<212> TYPE: DNA
<213> ORGANISM: Artificial Sequence
<220> FEATURE:
<223> OTHER INFORMATION: Primer

<400> SEQUENCE: 107

```
cgatgtcgtc tcgcagacca ttgcacaagc ctc       33
```

<210> SEQ ID NO 108
<211> LENGTH: 33
<212> TYPE: DNA

```
<213> ORGANISM: Artificial Sequence
<220> FEATURE:
<223> OTHER INFORMATION: Primer

<400> SEQUENCE: 108
gacctttcgt ctcgtctgcg catggatcgc tgc                                33

<210> SEQ ID NO 109
<211> LENGTH: 49
<212> TYPE: DNA
<213> ORGANISM: Artificial Sequence
<220> FEATURE:
<223> OTHER INFORMATION: Primer

<400> SEQUENCE: 109
gacctttcgt ctctgtctca catttcgatg cttgggtaga ataggtaag               49

<210> SEQ ID NO 110
<211> LENGTH: 53
<212> TYPE: DNA
<213> ORGANISM: Artificial Sequence
<220> FEATURE:
<223> OTHER INFORMATION: Primer

<400> SEQUENCE: 110
cgatgtacgt ctcactcggc ttgatccact taacgttact gaaatcatca aac          53

<210> SEQ ID NO 111
<211> LENGTH: 35
<212> TYPE: DNA
<213> ORGANISM: Artificial Sequence
<220> FEATURE:
<223> OTHER INFORMATION: Primer

<400> SEQUENCE: 111
gacctttcgt ctctctgctt gatctcgtct gccga                              35

<210> SEQ ID NO 112
<211> LENGTH: 39
<212> TYPE: DNA
<213> ORGANISM: Artificial Sequence
<220> FEATURE:
<223> OTHER INFORMATION: Primer

<400> SEQUENCE: 112
cgatgtacgt ctcagcagat caacggtcgt caacagacc                          39

<210> SEQ ID NO 113
<211> LENGTH: 56
<212> TYPE: DNA
<213> ORGANISM: Artificial Sequence
<220> FEATURE:
<223> OTHER INFORMATION: Primer

<400> SEQUENCE: 113
gacctttcgt ctctgtctca agcgtctaga aagaaggatt acctctaaac aagtgt       56

<210> SEQ ID NO 114
<211> LENGTH: 44
<212> TYPE: DNA
<213> ORGANISM: Artificial Sequence
<220> FEATURE:
<223> OTHER INFORMATION: Primer

<400> SEQUENCE: 114
cgatgtacgt ctcactcgaa tgattgaaca agatggattg cacg                    44
```

<210> SEQ ID NO 115
<211> LENGTH: 48
<212> TYPE: DNA
<213> ORGANISM: Artificial Sequence
<220> FEATURE:
<223> OTHER INFORMATION: Primer

<400> SEQUENCE: 115
gacctttcgt ctctgtctca aagcctcaga agaactcgtc aagaaggc                48

<210> SEQ ID NO 116
<211> LENGTH: 14
<212> TYPE: DNA
<213> ORGANISM: Artificial Sequence
<220> FEATURE:
<223> OTHER INFORMATION: Primer

<400> SEQUENCE: 116
ggtctcgtga gacg                14

<210> SEQ ID NO 117
<211> LENGTH: 12
<212> TYPE: DNA
<213> ORGANISM: Artificial Sequence
<220> FEATURE:
<223> OTHER INFORMATION: Primer

<400> SEQUENCE: 117
cgtctctaga cc                12

<210> SEQ ID NO 118
<211> LENGTH: 15
<212> TYPE: DNA
<213> ORGANISM: Artificial Sequence
<220> FEATURE:
<223> OTHER INFORMATION: Primer

<400> SEQUENCE: 118
cgtctcactc gggag                15

<210> SEQ ID NO 119
<211> LENGTH: 17
<212> TYPE: DNA
<213> ORGANISM: Artificial Sequence
<220> FEATURE:
<223> OTHER INFORMATION: Primer

<400> SEQUENCE: 119
aatgtgagac agagacg                17

<210> SEQ ID NO 120
<211> LENGTH: 11
<212> TYPE: DNA
<213> ORGANISM: Artificial Sequence
<220> FEATURE:
<223> OTHER INFORMATION: Primer

<400> SEQUENCE: 120
ggtctcggga g                11

<210> SEQ ID NO 121
<211> LENGTH: 11
<212> TYPE: DNA
<213> ORGANISM: Artificial Sequence
<220> FEATURE:

<223> OTHER INFORMATION: Primer

<400> SEQUENCE: 121
aatgtgagac c                                                                                        11

<210> SEQ ID NO 122
<211> LENGTH: 1202
<212> TYPE: DNA
<213> ORGANISM: Artificial Sequence
<220> FEATURE:
<223> OTHER INFORMATION: Plasmids

<400> SEQUENCE: 122
catggcacct gcagctcatt ggagagagac caagctttga tcggcacgta agaggttcca        60
actttcacca taatgaaata agatcactac cgggcgtatt ttttgagtta tcgagatttt       120
caggagctaa ggaagctaaa atgtcacatc tcgcagaact ggttgccagt gcgaaggcgg       180
ccattagcca ggcgtcagat gttgccgcgt tagataatgt gcgcgtcgaa tatttgggta       240
aaaaagggca cttaacgctt cagatgacga ccctgcgtga gctgccgcca gaagagcgtc       300
cggcagctgg tgcggttatc aacgaagcga aagagcaggt tcagcaggcg ctgaatgcgc       360
gtaaagcgga actggaaagc gctgcactga atgcgcgtct ggcggcggaa acgattgatg       420
tctctctgcc aggtcgtcgc attgaaaacg gcggtctgca tccggttacc cgtaccatcg       480
accgtatcga aagtttcttc ggtgagcttg ctttaccgt ggcaaccggg ccggaaatcg        540
aagacgatta tcataacttc gatgctctga acattcctgg tcaccacccg gcgcgcgctg       600
accacgacac tttctggttt gacactaccc gcctgctgcg tacccagacc tctggcgtac       660
agatccgcac catgaaagcc cagcagccac cgattcgtat catcgcgcct ggccgtgttt       720
atcgtaacga ctacgaccag actcacacgc cgatgttcca tcagatggaa ggtctgattg       780
ttgataccaa catcagcttt accaacctga aaggcacgct gcacgacttc ctgcgtaact       840
tctttgagga agatttgcag attcgcttcc gtccttccta cttcccgttt gctgaacctt       900
ctgcagaagt ggacgtcatg ggtaaaaacg gtaaatggct ggaagtgctg ggctgcggga       960
tggtgcatcc gaacgtgttg cgtaacgttg gcatcgaccc ggaagtttac tctggtttcg      1020
ggttcgggat ggggatggag cgtctgacta tgttgcgtta cggcgtcacc gacctgcgtt      1080
cattcttcga aaacgatctg cgtttcctca aacagtttaa ataataaaag cttggtctct      1140
cgctcattag agacggccgg attgcggccg ctaaccggcc gtctcacgta atatgcaggt      1200
gc                                                                    1202

<210> SEQ ID NO 123
<211> LENGTH: 1202
<212> TYPE: DNA
<213> ORGANISM: Artificial Sequence
<220> FEATURE:
<223> OTHER INFORMATION: Plasmids

<400> SEQUENCE: 123
catggcacct gcagctcatt agagacggcc ggattgcggc cgctaaccgg ccgtctcacg        60
taagcgagag accaagcttt tattatttaa actgtttgag gaaacgcaga tcgttttcga       120
agaatgaacg caggtcggtg acgccgtaac gcaacatagt cagacgctcc atccccatcc       180
cgaacccgaa accagagtaa acttccgggt cgatgccaac gttacgcaac acgttcggat       240
gcaccatccc gcagcccagc acttccagcc atttaccgtt tttacccatg acgtccactt       300
ctgcagaagg ttcagcaaac gggaagtagg aaggacgaa gcgaatctgc aaatcttcct       360

```
caaagaagtt acgcaggaag tcgtgcagcg tgcctttcag gttggtaaag ctgatgttgg      420
tatcaacaat cagaccttcc atctgatgga acatcggcgt gtgagtctgg tcgtagtcgt      480
tacgataaac acggccaggc gcgatgatac gaatcggtgg ctgctgggct tcatggtgc       540 ggatctgtac gccagaggtc tgggtacgca gcaggcggga gtgtcaaac cagaaagtgt       600 cgtggtcagc gcgcgccggg tggtgaccag gaatgttcag agcatcgaag ttatgataat      660
cgtcttcgat ttccggcccg gttgccacgg taaagccaag ctcaccgaag aaactttcga      720
tacggtcgat ggtacgggta accggatgca gaccgccgtt ttcaatgcga cgacctggca      780
gagagacatc aatcgtttcc gccgccagac gcgcattcag tgcagcgctt tccagttccg      840
ctttacgcgc attcagcgcc tgctgaacct gctctttcgc ttcgttgata accgcaccag      900
ctgccggacg ctcttctggc ggcagctcac gcagggtcgt catctgaagg gttaagtgcc      960
cttttttacc caaatattcg acgcgcacat tatctaacgc ggcaacatct gacgcctggc     1020
taatggccgc cttcgcactg gcaaccagtt ctgcgagatg tgacatttta gcttccttag     1080
ctcctgaaaa tctcgataac tcaaaaaata cgcccggtag tgatcttatt tcattatggt     1140
gaaagttgga acctcttacg tgccgatcaa agcttggtct ctctcccgta atatgcaggt     1200
gc                                                                    1202
```

<210> SEQ ID NO 124
<211> LENGTH: 1202
<212> TYPE: DNA
<213> ORGANISM: Artificial Sequence
<220> FEATURE:
<223> OTHER INFORMATION: Plasmids

<400> SEQUENCE: 124

```
catggcacct gcagctcatt agcgagagac caagctttta ttatttaaac tgtttgagga       60
aacgcagatc gttttcgaag aatgaacgca ggtcggtgac gccgtaacgc aacatagtca      120
gacgctccat ccccatcccg aacccgaaac cagagtaaac ttccgggtcg atgccaacgt      180
tacgcaacac gttcggatgc accatcccgc agcccagcac ttccagccat ttaccgtttt      240
tacccatgac gtccacttct gcagaaggtt cagcaaacgg gaagtaggaa ggacggaagc      300
gaatctgcaa atcttcctca agaagttac gcaggaagtc gtgcagcgtg cctttcaggt       360
tggtaaagct gatgttggta tcaacaatca gaccttccat ctgatggaac atcggcgtgt      420
gagtctggtc gtagtcgtta cgataaacac ggccaggcgc gatgatacga atcggtggct      480
gctgggcttt catggtgcgg atctgtacgc cagaggtctg ggtacgcagc aggcgggtag      540
tgtcaaacca gaaagtgtcg tggtcagcgc gcgccgggtg gtgaccagga atgttcagag      600
catcgaagtt atgataatcg tcttcgattt ccggcccggt tgccacggta aagccaagct      660
caccgaagaa actttcgata cggtcgatgg tacgggtaac cggatgcaga ccgccgtttt      720
caatgcgacg acctggcaga gagacatcaa tcgtttccgc cgccagacgc gcattcagtg      780
cagcgctttc cagttccgct ttacgcgcat tcagcgcctg ctgaacctgc tctttcgctt      840
cgttgataac cgcaccagct gccggacgct cttctggcgg cagctcacgc agggtcgtca      900
tctgaagggt taagtgccct tttttaccca aatattcgac gcgcacatta tctaacgcgg      960
caacatctga cgcctggcta atggccgcct tcgcactggc aaccagttct gcgagatgtg     1020
acattttagc ttccttagct cctgaaaatc tcgataactc aaaaaatacg cccggtagtg     1080
atcttatttc attatggtga aagttggaac ctcttacgtg ccgatcaaag cttggtctct     1140
```

| | |
|---|---|
| ctcccattag agacggccgg attgcggccg ctaaccggcc gtctcacgta atatgcaggt | 1200 |
| gc | 1202 |

<210> SEQ ID NO 125
<211> LENGTH: 1202
<212> TYPE: DNA
<213> ORGANISM: Artificial Sequence
<220> FEATURE:
<223> OTHER INFORMATION: Plasmids

<400> SEQUENCE: 125

| | |
|---|---|
| catggcacct gcagctcatt agagacggcc ggattgcggc cgctaaccgg ccgtctcacg | 60 |
| taggagagag accaagcttt gatcggcacg taagaggttc aactttcac cataatgaaa | 120 |
| taagatcact accgggcgta ttttttgagt tatcgagatt ttcaggagct aaggaagcta | 180 |
| aaatgtcaca tctcgcagaa ctggttgcca gtgcgaaggc ggccattagc caggcgtcag | 240 |
| atgttgccgc gttagataat gtgcgcgtcg aatatttggg taaaaaggg cacttaaccc | 300 |
| ttcagatgac gaccctgcgt gagctgccgc agaagagcg tccggcagct ggtgcggtta | 360 |
| tcaacgaagc gaaagagcag gttcagcagg cgctgaatgc gcgtaaagcg gaactggaaa | 420 |
| gcgctgcact gaatgcgcgt ctggcggcgg aaacgattga tgtctctctg ccaggtcgtc | 480 |
| gcattgaaaa cggcggtctg catccggtta cccgtaccat cgaccgtatc gaaagtttct | 540 |
| tcggtgagct tggctttacc gtggcaaccg ggccggaaat cgaagacgat tatcataact | 600 |
| tcgatgctct gaacattcct ggtcaccacc ggcgcgcgc tgaccacgac actttctggt | 660 |
| ttgacactac ccgcctgctg cgtacccaga cctctggcgt acagatccgc accatgaaag | 720 |
| cccagcagcc accgattcgt atcatcgcgc ctggccgtgt ttatcgtaac gactacgacc | 780 |
| agactcacac gccgatgttc catcagatgg aaggtctgat tgttgatacc aacatcagct | 840 |
| ttaccaacct gaaaggcacg ctgcacgact tcctgcgtaa cttctttgag gaagatttgc | 900 |
| agattcgctt ccgtccttcc tacttcccgt ttgctgaacc ttctgcagaa gtggacgtca | 960 |
| tgggtaaaaa cggtaaatgg ctggaagtgc tgggctgcgg gatggtgcat ccgaacgtgt | 1020 |
| tgcgtaacgt tggcatcgac ccggaagttt actctggttt cgggttcggg atggggatgg | 1080 |
| agcgtctgac tatgttgcgt tacggcgtca ccgacctgcg ttcattcttc gaaaacgatc | 1140 |
| tgcgtttcct caaacagttt aaataataaa agcttggtct ctcgctcgta atatgcaggt | 1200 |
| gc | 1202 |

<210> SEQ ID NO 126
<211> LENGTH: 1495
<212> TYPE: DNA
<213> ORGANISM: Artificial Sequence
<220> FEATURE:
<223> OTHER INFORMATION: Plasmids

<400> SEQUENCE: 126

| | |
|---|---|
| catggcgtct cacattggag agagaccaag ctttgatcgg cacgtaagag gttccaactt | 60 |
| tcaccataat gaaataagat cactaccggg cgtattttt gagttatcga gattttcagg | 120 |
| agctaaggaa gctaaaatgt cacatctcgc agaactggtt gccagtgcga aggcggccat | 180 |
| tagccaggcg tcagatgttg ccgcgttaga taatgtgcgc gtcgaatatt tgggtaaaaa | 240 |
| agggcactta acccttcaga tgacgaccct gcgtgagctg ccgccagaag agcgtccggc | 300 |
| agctggtgcg gttatcaacg aagcgaaaga gcaggttcag caggcgctga atgcgcgtaa | 360 |
| agcggaactg gaaagcgctg cactgaatgc gcgtctggcg gcggaaacga ttgatgtctc | 420 |

```
tctgccaggt cgtcgcattg aaaacggcgg tctgcatccg gttacccgta ccatcgaccg    480
tatcgaaagt ttcttcggtg agcttggctt taccgtggca accgggccgg aaatcgaaga    540
cgattatcat aacttcgatg ctctgaacat tcctggtcac cacccggcgc gcgctgacca    600
cgacactttc tggtttgaca ctacccgcct gctgcgtacc cagacctctg cgtacagat    660 ccgcaccatg aaagcccagc agccaccgat tcgtatcatc gcgcctggcc gtgtttatcg    720
taacgactac gaccagactc acacgccgat gttccatcag atggaaggtc tgattgttga    780
taccaacatc agctttacca acctgaaagg cacgctgcac gacttcctgc gtaacttctt    840
tgaggaagat ttgcagattc gcttccgtcc ttcctacttc ccgtttgctg aaccttctgc    900
agaagtggac gtcatgggta aaaacggtaa atggctggaa gtgctgggct gcgggatggt    960
gcatccgaac gtgttgcgta acgttggcat cgacccggaa gtttactctg gtttcgggtt   1020
cgggatgggg atggagcgtc tgactatgtt gcgttacggc gtcaccgacc tgcgttcatt   1080
cttcgaaaac gatctgcgtt tcctcaaaca gtttaaataa taaaagcttg gtctctcgct   1140
cattgcttgc aggtgttatt accaggcaaa gcgccattcg ccattcaggc tgcgcaactg   1200
ttgggaaggg cgatcggtgc gggcctcttc gctattacgc cagctggcga aggggggatg   1260
tgctgcaagg cgattaagtt gggtaacgcc agggttttcc cagtcacgac gttgtaaaac   1320
gacggccagt gaatccgtaa tcatggtcat agctgtttcc tgtgtgaaat tgttatccgc   1380
tcacaattcc acacaacata cgagccggaa gcataaagtg taaagcctgg ggtgcctaat   1440
gagtgagcta actcacatta attgcgttgc gccacctgcc cgccgtaaga gacgc         1495

<210> SEQ ID NO 127
<211> LENGTH: 1495
<212> TYPE: DNA
<213> ORGANISM: Artificial Sequence
<220> FEATURE:
<223> OTHER INFORMATION: Plasmids

<400> SEQUENCE: 127
catggcgtct cacattgctt gcaggtgtta ttaccaggca aagcgccatt cgccattcag     60
gctgcgcaac tgttgggaag ggcgatcggt gcgggcctct tcgctattac gccagctggc    120
gaaaggggga tgtgctgcaa ggcgattaag ttgggtaacg ccagggtttt cccagtcacg    180
acgttgtaaa acgacggcca gtgaatccgt aatcatggtc atagctgttt cctgtgtgaa    240
attgttatcc gctcacaatt ccacacaaca tacgagccgg aagcataaag tgtaaagcct    300
ggggtgccta atgagtgagc taactcacat taattgcgtt gcgccacctg cccgccgtaa    360
gcgagagacc aagcttttat tatttaaact gtttgaggaa acgcagatcg ttttcgaaga    420
atgaacgcag gtcggtgacg ccgtaacgca acatagtcag acgctccatc ccatcccga    480 acccgaaacc agagtaaact tccgggtcga tgccaacgtt acgcaacacg ttcggatgca    540
ccatcccgca gccagcact tccagccatt taccgttttt acccatgacg tccacttctg    600
cagaaggttc agcaaacggg aagtaggaag gacggaagcg aatctgcaaa tcttcctcaa    660
agaagttacg caggaagtcg tgcagcgtgc ctttcaggtt ggtaaagctg atgttggtat    720
caacaatcag accttccatc tgatggaaca tcggcgtgtg agtctggtcg tagtcgttac    780
gataaacacg gccaggcgcg atgatacgaa tcggtggctg ctgggctttc atggtgcgga    840
tctgtacgcc agaggtctgg gtacgcagca ggcgggtagt gtcaaccag aaagtgtcgt    900 ggtcagcgcg cgccgggtgg tgaccaggaa tgttcagagc atcgaagtta tgataatcgt    960
```

| | | |
|---|---|---|
| cttcgatttc cggcccggtt gccacggtaa agccaagctc accgaagaaa ctttcgatac | 1020 | |
| ggtcgatggt acgggtaacc ggatgcagac cgccgttttc aatgcgacga cctggcagag | 1080 | |
| agacatcaat cgtttccgcc gccagacgcg cattcagtgc agcgctttcc agttccgctt | 1140 | |
| tacgcgcatt cagcgcctgc tgaacctgct ctttcgcttc gttgataacc gcaccagctg | 1200 | |
| ccggacgctc ttctggcggc agctcacgca gggtcgtcat ctgaagggtt aagtgccctt | 1260 | |
| ttttacccaa atattcgacg cgcacattat ctaacgcggc aacatctgac gcctggctaa | 1320 | |
| tggccgcctt cgcactggca accagttctg cgagatgtga cattttagct tccttagctc | 1380 | |
| ctgaaaatct cgataactca aaaaatacgc ccggtagtga tcttatttca ttatggtgaa | 1440 | |
| agttggaacc tcttacgtgc cgatcaaagc ttggtctctc tcccgtaaga gacgc | 1495 | |

<210> SEQ ID NO 128
<211> LENGTH: 1495
<212> TYPE: DNA
<213> ORGANISM: Artificial Sequence
<220> FEATURE:
<223> OTHER INFORMATION: Plasmids

<400> SEQUENCE: 128

| | | |
|---|---|---|
| catggcgtct cacattagcg agagaccaag ctttttattat ttaaactgtt tgaggaaacg | 60 | |
| cagatcgttt tcgaagaatg aacgcaggtc ggtgacgccg taacgcaaca tagtcagacg | 120 | |
| ctccatcccc atcccgaacc cgaaaccaga gtaaacttcc gggtcgatgc caacgttacg | 180 | |
| caacacgttc ggatgcacca tcccgcagcc cagcacttcc agccatttac cgttttttacc | 240 | |
| catgacgtcc acttctgcag aaggttcagc aaacgggaag taggaaggac ggaagcgaat | 300 | |
| ctgcaaatct tcctcaaaga agttacgcag gaagtcgtgc agcgtgcctt tcaggttggt | 360 | |
| aaagctgatg ttggtatcaa caatcagacc ttccatctga tggaacatcg gcgtgtgagt | 420 | |
| ctggtcgtag tcgttacgat aaacacggcc aggcgcgatg atacgaatcg gtggctgctg | 480 | |
| ggctttcatg gtgcggatct gtacgccaga ggtctgggta cgcagcaggc gggtagtgtc | 540 | |
| aaaccagaaa gtgtcgtggt cagcgcgcgc cgggtggtga ccaggaatgt tcagagcatc | 600 | |
| gaagttatga taatcgtctt cgatttccgg cccggttgcc acggtaaagc caagctcacc | 660 | |
| gaagaaactt tcgatacggt cgatggtacg ggtaaccgga tgcagaccgc cgttttcaat | 720 | |
| gcgacgacct ggcagagaga catcaatcgt ttccgccgcc agacgcgcat tcagtgcagc | 780 | |
| gctttccagt tccgctttac gcgcattcag cgcctgctga acctgctctt tcgcttcgtt | 840 | |
| gataaccgca ccagctgccg gacgctcttc tggcggcagc tcacgcaggg tcgtcatctg | 900 | |
| aagggttaag tgcccttttt tacccaaata ttcgacgcgc acattatcta acgcggcaac | 960 | |
| atctgacgcc tggctaatgg ccgccttcgc actggcaacc agttctgcga gatgtgacat | 1020 | |
| tttagcttcc ttagctcctg aaaatctcga taactcaaaa aatacgcccg gtagtgatct | 1080 | |
| tatttcatta tggtgaaagt tggaacctct tacgtgccga tcaaagcttg gtctctctcc | 1140 | |
| cattgcttgc aggtgttatt accaggcaaa gcgccattcg ccattcaggc tgcgcaactg | 1200 | |
| ttgggaaggg cgatcggtgc gggcctcttc gctattacgc cagctggcga aggggggatg | 1260 | |
| tgctgcaagg cgattaagtt gggtaacgcc agggttttcc cagtcacgac gttgtaaaac | 1320 | |
| gacggccagt gaatccgtaa tcatggtcat agctgtttcc tgtgtgaaat tgttatccgc | 1380 | |
| tcacaattcc acacaacata cgagccggaa gcataaagtg taaagcctgg ggtgcctaat | 1440 | |
| gagtgagcta actcacatta attgcgttgc gccacctgcc cgccgtaaga gacgc | 1495 | |

<210> SEQ ID NO 129
<211> LENGTH: 1495
<212> TYPE: DNA
<213> ORGANISM: Artificial Sequence
<220> FEATURE:
<223> OTHER INFORMATION: Plasmids

<400> SEQUENCE: 129

```
catggcgtct cacattgctt gcaggtgtta ttaccaggca aagcgccatt cgccattcag        60
gctgcgcaac tgttgggaag ggcgatcggt gcgggcctct tcgctattac gccagctggc       120
gaaaggggga tgtgctgcaa ggcgattaag ttgggtaacg ccagggtttt cccagtcacg       180
acgttgtaaa acgacggcca gtgaatccgt aatcatggtc atagctgttt cctgtgtgaa       240
attgttatcc gctcacaatt ccacacaaca tacgagccgg aagcataaag tgtaaagcct       300
ggggtgccta atgagtgagc taactcacat taattgcgtt gcgccacctg cccgccgtag       360
gagagagacc aagctttgat cggcacgtaa gaggttccaa ctttcaccat aatgaaataa       420
gatcactacc gggcgtattt tttgagttat cgagattttc aggagctaag gaagctaaaa       480
tgtcacatct cgcagaactg gttgccagtg cgaaggcggc cattagccag gcgtcagatg       540
ttgccgcgtt agataatgtg cgcgtcgaat atttgggtaa aaaagggcac ttaacccttc       600
agatgacgac cctgcgtgag ctgccgccag aagagcgtcc ggcagctggt gcggttatca       660
acgaagcgaa agagcaggtt cagcaggcgc tgaatgcgcg taaagcggaa ctggaaagcg       720
ctgcactgaa tgcgcgtctg gcggcggaaa cgattgatgt ctctctgcca ggtcgtcgca       780
ttgaaaacgg cggtctgcat ccggttaccc gtaccatcga ccgtatcgaa agtttcttcg       840
gtgagcttgg ctttaccgtg gcaaccgggc cggaaatcga agacgattat cataacttcg       900
atgctctgaa cattcctggt caccacccgg cgcgcgctga ccacgacact ttctggtttg       960
acactacccg cctgctgcgt acccagacct ctggcgtaca gatccgcacc atgaaagccc      1020
agcagccacc gattcgtatc atcgcgcctg gccgtgttta tcgtaacgac tacgaccaga      1080
ctcacacgcc gatgttccat cagatggaag gtctgattgt tgataccaac atcagcttta      1140
ccaacctgaa aggcacgctg cacgacttcc tgcgtaactt ctttgaggaa gatttgcaga      1200
ttcgcttccg tccttcctac ttcccgtttg ctgaaccttc tgcagaagtg gacgtcatgg      1260
gtaaaaacgg taaatggctg gaagtgctgg gctgcgggat ggtgcatccg aacgtgttgc      1320
gtaacgttgg catcgacccg gaagtttact ctggtttcgg gttcgggatg gggatggagc      1380
gtctgactat gttgcgttac ggcgtcaccg acctgcgttc attcttcgaa aacgatctgc      1440
gtttcctcaa acagtttaaa taataaaagc ttggtctctc gctcgtaaga gacgc           1495
```